(12) United States Patent
Salipur et al.

(10) Patent No.: US 9,737,493 B2
(45) Date of Patent: Aug. 22, 2017

(54) COMPOSITIONS AND METHODS FOR MODULATING DNMT1 INHIBITOR ACTIVITY

(71) Applicant: University of Louisville Research Foundation, Inc., Louisville, KY (US)

(72) Inventors: Francesca R. Salipur, Louisville, KY (US); Paula J. Bates, Louisville, KY (US); Elsa Merit Reyes-Reyes, Prospect, KY (US); Bo Xu, Louisville, KY (US); Gerald B. Hammond, Shelbyville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 14/426,399

(22) PCT Filed: Sep. 6, 2013

(86) PCT No.: PCT/US2013/058566
§ 371 (c)(1),
(2) Date: Mar. 6, 2015

(87) PCT Pub. No.: WO2014/039860
PCT Pub. Date: Mar. 13, 2014

(65) Prior Publication Data
US 2015/0238439 A1 Aug. 27, 2015

Related U.S. Application Data

(60) Provisional application No. 61/698,403, filed on Sep. 7, 2012, provisional application No. 61/786,705, filed on Mar. 15, 2013.

(51) Int. Cl.
| | | |
|---|---|---|
| A61K 31/45 | (2006.01) | |
| A61K 31/198 | (2006.01) | |
| A61K 31/045 | (2006.01) | |
| A61K 45/06 | (2006.01) | |
| A61K 31/22 | (2006.01) | |
| A61K 38/06 | (2006.01) | |

(52) U.S. Cl.
CPC .......... *A61K 31/045* (2013.01); *A61K 31/198* (2013.01); *A61K 31/22* (2013.01); *A61K 38/063* (2013.01); *A61K 45/06* (2013.01)

(58) Field of Classification Search
CPC ............................. A61K 31/45; A61K 31/198
See application file for complete search history.

(56) References Cited

U.S. PATENT DOCUMENTS

| | | |
|---|---|---|
| 4,018,802 A | 4/1977 | Cragoe, Jr. et al. |
| 4,559,157 A | 12/1985 | Smith et al. |
| 4,608,392 A | 8/1986 | Jacquet et al. |
| 4,820,508 A | 4/1989 | Wortzman |
| 4,938,949 A | 7/1990 | Borch et al. |
| 4,992,478 A | 2/1991 | Geria |
| 5,223,409 A | 6/1993 | Ladner et al. |
| 5,849,500 A | 12/1998 | Breitling et al. |
| 6,387,901 B1 | 5/2002 | Chupak |
| 8,207,381 B2 | 6/2012 | Hammond et al. |
| 8,703,829 B2 | 4/2014 | Hammond et al. |
| 2008/0188570 A1* | 8/2008 | Hammond ............ C07C 17/266 514/739 |
| 2011/0229883 A1 | 9/2011 | Spur et al. |

FOREIGN PATENT DOCUMENTS

| | | |
|---|---|---|
| AU | 2008213666 B2 | 8/2008 |
| CA | 1064961 A1 | 10/1979 |
| DE | 10029709 A1 | 1/2002 |
| EP | 2111385 B1 | 11/2014 |
| JP | 51125020 A | 11/1976 |
| WO | 90/02809 A1 | 3/1990 |
| WO | 91/17271 A1 | 11/1991 |
| WO | 92/01047 A1 | 1/1992 |
| WO | 92/09690 A1 | 6/1992 |
| WO | 92/15679 A1 | 9/1992 |
| WO | 92/18619 A1 | 10/1992 |
| WO | 92/20791 A1 | 11/1992 |
| WO | 93/01288 A1 | 1/1993 |
| WO | 01/96262 A1 | 12/2001 |
| WO | 2006/078752 A2 | 7/2006 |
| WO | 2007/096576 A1 | 8/2007 |
| WO | 2008/098077 A2 | 8/2008 |
| WO | 2011/115513 A2 | 9/2011 |
| WO | 2012/019284 A1 | 2/2012 |

(Continued)

OTHER PUBLICATIONS

AU App. No. 2008213666, Examiner's First Report dated Jan. 30, 2012, 3 pages.
AU App. No. 2008213666, Patent Examination Report No. 2 dated Mar. 26, 2013, 6 pages.
CA App. No. 2,677,353, Office Action dated Apr. 16, 2014, 3 pages.
CA App. No. 2,677,353, Office Action dated Apr. 29, 2015, 3 pages.
CA App. No. 2,677,353, Office Action dated Jan. 20, 2016, 3 pages.
CA App. No. 2,677,353, Office Action dated Apr. 11, 2016, 3 pages.
EP App. No. 08729198.5, Communication Article 94(3) EPC dated Apr. 18, 2012, 4 pages.

(Continued)

*Primary Examiner* — James D Anderson
(74) *Attorney, Agent, or Firm* — Arrigo, Lee & Guttman LLP; Harry J. Guttman

(57) ABSTRACT

Some aspects of the invention include attenuating DNMT1 inhibitor activity in an animal comprising administering an antioxidant. Other aspects of the invention include methods comprising administering a composition comprising a DNMT1 inhibitor and an antioxidant. In some instances in the methods, the animal is undergoing a treatment for cancer. Additional aspects of the invention include compositions comprising a DNMT1 inhibitor and an antioxidant.

19 Claims, 27 Drawing Sheets

(56) References Cited

FOREIGN PATENT DOCUMENTS

| | | |
|---|---|---|
| WO | 2012/122219 A2 | 9/2012 |
| WO | 2014/039860 A2 | 3/2014 |

OTHER PUBLICATIONS

EP App. No. 08729198.5, Communication Article 94(3) EPC dated Apr. 19, 2013, 3 pages.
EP App. No. 12184131.6, Extended European Search Report dated Feb. 8, 2013, 5 pages.
EP App. No. 12184131.6, Communication Article 94(3) EPC dated Nov. 11, 2013, 3 pages.
JP App. No. 2009-549221, Office Action, dated Apr. 16, 2013, 5 pages. (English language translation).
JP App. No. 2009-549221, Office Action, dated May 7, 2014, 3 pages. (English language translation).
PCT/US2008/053214, International Search Report and Written Opinion, mailed Oct. 22, 2008, 18 pages.
PCT/US2013/058566, International Search Report and Written Opinion, mailed Jan. 15, 2014, 8 pages.
U.S. Appl. No. 12/027,154, Advisory Action dated Oct. 1, 2010, 3 pages.
U.S. Appl. No. 12/027,154, Final Office action dated May 24, 2010, 10 pages.
U.S. Appl. No. 12/027,154, Non-Final Office action dated Nov. 13, 2009, 8 pages.
U.S. Appl. No. 12/027,154, Notice of Allowance with Examiner's Amendment dated Feb. 28, 2012, 17 pages.
U.S. Appl. No. 12/027,154, Restriction Requirement dated Aug. 11, 2009, 10 pages.
U.S. Appl. No. 13/478,789, Final Office Action dated Jul. 31, 2013, 19 pages.
U.S. Appl. No. 13/478,789, Interview Summary dated Oct. 30, 2013, 4 pages.
U.S. Appl. No. 13/478,789, non-Final Office Action dated Feb. 5, 2013, 21 pages.
U.S. Appl. No. 13/478,789, Notice of Allowance dated Nov. 25, 2013, 23 pages.
U.S. Appl. No. 13/478,789, Restriction Requirement dated Oct. 26, 2012, 8 pages.
Aarti et al., "Phosphorylation of eIF2 alpha in Sf9 cells: a stress, survival and suicidal signal" Apoptosis (2010) vol. 15, pp. 679-692.
Abdel-Samad et al., "MiniSOX9, a dominant-negative variant in colon cancer cells" Oncogene (2011) vol. 30, No. 22, pp. 2493-2503.
Acevedo et al., "Inducible FGFR-1 activation leads to irreversible prostate adenocarcinoma and an epithelial-to-mesenchymal transition" Cancer Cell (2007) vol. 12, pp. 559-571.
Adams et al., "Discovery of Small-Molecule Enhancers of Reactive Oxygen Species That are Nontoxic or Cause Genotype-Selective Cell Death" ACS Chemical Biology (2013) vol. 8, pp. 923-929.
Aitken et al., "Synthesis of Linear Alkynes from Other Alkynes" Science of Synthesis (2008) vol. 43, pp. 555-630.
Hay et al., "Bacteriophage cloning and *Escherichia coli* expression of a human IgM Fab" Hum. Antibod. Hybridomas (1992) vol. 3, pp. 81-85.
Higdon et al., "Cell Signaling by Reactive Lipid Species: New Concepts and Molecular Mechanisms" Biochem J (2012) vol. 442, pp. 453-464.
Hong et al., "An Efficient Synthesis of Difluoropropargyl Bromides" Synthesis (2006) vol. 5, pp. 803-806.
Hsiang et al., "Camptothecin induces protein-linked DNA breaks via mammalian DNA topoisomerase I" Journal of Biological Chemistry (1985) vol. 260, pp. 14873-14878.
Hu et al., "Mitochondrial Manganese-Superoxide Dismutase Expression in Ovarian Cancer: Role in Cell Proliferation and Response to Oxidative Stress." Journal of Biological Chemistry (2005) vol. 280, No. 47, pp. 39485-39492.

Huse et al., "Generation of a large combinatorial library of the immunoglobulin repertoire in phage lambda" Science (1989) vol. 246, No. 4935, pp. 1275-1281.
Indran et al., "Recent advances in apoptosis, mitochondria and drug resistance in cancer cells" Biochimica et Biophysica Acta (BBA)—Bioenergetics (2011) vol. 1807, No. 6, pp. 735-745.
Issa et al., "Targeting DNA methylation" Clin Cancer Res. (2009) vol. 15, No. 12, pp. 3938-3946.
Itoh et al., "Keap-1 represses nuclear activation of antioxidant response elements by Nrf2 through binding to the amino-terminal Neh2 domain" Genes and Development (1999) vol. 13, pp. 76-86.
Jeon et al., "Inhibition of Bovine Plasma Amine Oxidase by 1,4-Diamino-2-butenes and -2-butynes" Bioorganic & Medicinal Chem. (2003) vol. 11, pp. 4631-4641.
Jose et al., "Novel histone deacetylase inhibitors: cyclic tetrapeptide with trifluoromethyl and pentafluoroethyl ketones" Bioorganic & Medicinal Chemistry Letters (2004) vol. 14, pp. 5343-5346.
Kekec et al., "Antioxidant enzyme levels in cases with gastrointesinal cancer" European Journal of Internal Medicine (2009) vol. 20, pp. 403-406.
Khleif et al., "AACR-FDA-NCI Cancer Biomarkers Collaborative. AACR-FDA-NCI Cancer Biomarkers Collaborative consensus report: advancing the use of biomarkers in cancer drug development" Clin Cancer Res. (2010) vol. 16, No. 13, pp. 3299-3318.
Kim et al., "BLT2 promotes the invasion and metastasis of aggressive bladder cancer cells through a reactive oxygen species-linked pathway" Free Radical Biology and Medicine (2010) vol. 49, pp. 1072-1081.
Kobayashi et al., "Oxidative Stress Sensor Keap1 Functions as an Adaptor for Cul3-Based E3 Ligase to Regulate Proteasomal Degradation of Nrf2" Molecular and Cellular Biology (2004) vol. 24, No. 16, pp. 7130-7139.
Kobayashi et al., "Oxidative and Electrophilic Stresses Activate Nrf2 through Inhibition of Ubiquitination Activity of Keap1" Molecular and Cellular Biology (2006) vol. 26, No. 1, pp. 221-229.
Kohler et al., "Continuous cultures of fused cells secreting antibody of predefined specificity" Nature (1975) vol. 256, pp. 495-497.
Kozbor et al., "The production of monoclonal antibodies from human lymphocytes" Immunol. Today (1983) vol. 4, No. 3, pp. 72-79.
Kwok et al., "Total Synthesis of 7,7-, 10,10-, and 13,13-Difluoroarachidonic Acids" J. Am. Chem. Soc. (1987) vol. 109, pp. 3684-3692.
Lan et al., "An Efficient Preparation of TIPS-Halofluoropropyane and its Application to the Diastereoselective synthesis of Propargylic Fluorohydrins" J. Org. Chem. (2000) vol. 65, No. 13, pp. 4217-4221.
Landriscina et al., "Adaptation to Oxidative Stress, Chemoresistance, and Cell Survival" Antioxidants and Redox Signaling (2009) vol. 11, No. 11, pp. 2701-2716.
Le Coq, "Synthese et proprietes :de l'aldehyde trichlorocrotonique" Annales De Chimie (Paris, France) (1968a) vol. 3, No. 6, pp. 517-528.
Le Coq, "Synthesis and properties of 3,4-epoxy-1, 1-dichloro-1-butene and trichlorotetrolaldehyde" Annales De Chimie (Paris, France) (1968b) vol. 3, No. 6, pp. 529-541.
Lee "GRP78 Induction in Cancer: Therapeutic and Prognostic Implications" Cancer Research (2007) vol. 67, No. 8, pp. 3496-3499.
Lee et al., "Inhibition of DNA methylation by caffeic acid and chlorogenic acid, two common catechol-containing coffee polyphenols" Carcinogenesis (2006) vol. 27, No. 2, pp. 269-277.
Linardou et al., "Assessment of somatic k-RAS mutations as a mechanism associated with resistance to EGFR-targeted agents: a systematic review and meta-analysis of studies in advanced non-small-cell lung cancer and metastatic colorectal cancer" Lancet Oncol. (2008) vol. 9, pp. 962-972.
Lis et al., "Synthesis of Aminoprostanoids A and J" Zhurnal Organnicheskoi Khimii (1992) vol. 28, No. 9, pp. 1854-1861.
Lis et al., "Synthesis of Aminoprostanoids A and J" Institute of Bioorganic Chemistry, Belorussian Academy of Sciences, Minsk—

(56) References Cited

OTHER PUBLICATIONS an English-language translation published 1993 of an original article printed in the Zhurnal Organnicheskoi Khimii (1992) vol. 28, No. 9, pp. 1854-1861. (6 pages).
Lu et al., "Targeting Thioredoxin Reductase is a Basis for Cancer Therapy by Arsenic Trioxide" PNAS (2007) vol. 104, No. 30, pp. 12288-12293.
Magda et al., "Motexafin Gadolinium: a novel redox active drug for cancer therapy" Seminars in Cancer Biology (2006) vol. 16, pp. 466-476.
Malhotra et al., "Endoplasmic Reticulum Stress and Oxidative Stress: A vicious cycle or double-edged sword?" Antioxidants & Redox Signaling (2007) vol. 9, No. 12, pp. 2277-2293.
Marson et al., "Structure-activity relationships of aryloxyalkanoic acid hydroxyamides as potent inhibitors of histone deacetylase" Bioorganic & Medicinal Chemistry Letters (2007) vol. 17, pp. 136-141.
McCabe et al., "Cancer DNA methylation: molecular mechanisms and clinical implications" Clin Cancer Res. (2009) vol. 15, No. 12, pp. 3927-3937.
McCarry et al., "A Facile Synthesis of Muscimol" Tetrahedron Letters (1981) vol. 22, No. 51, pp. 5153-5156.
Mi et al., "A cautionary note on using N-acetylcysteine as an antagonist to assess isothiocyanate-induced reactive oxygen species-mediated apoptosis" Analytical Biochemistry (2010) vol. 405, pp. 269-271.
Mitsuishi et al., "The Keap1-Nrf2 system in cancers: Stress response and anabolic metabolism" Frontiers in Oncology (2012) vol. 2, Article 200. (13 pages).
Moinova "Up-Regulation of the Human γ-Glutamylcysteine Synthetase Regulatory Subunit Gene Involves Binding of Nrf-2 to an Electrophile Responsive Element" Biochemical and Biophysical Research Communications (1999) vol. 261, pp. 661-668.
Morgan, "Tetrazolium (MTT) Assay for Cellular Viability and Activity" Methods in Molecular Biology (1998) vol. 79, pp. 179-183.
Needleman et al., "A General Method Application to the Search for Similarities in the Amino Acid Sequence of Two Proteins" J. Mol. Biol. (1970) vol. 48, pp. 443-453.
Nishikawa "Reactive oxygen species in tumor metastasis" Cancer Letters (2008) vol. 266, pp. 53-59.
Okada et al., "Stereoselective construction of functionalized (Z)-fluoroalkenes directed to depsipeptide isosteres" Tetrahedron Letters (2002) vol. 43, pp. 5845-5847.
Pelicano et al., "ROS Stress in cancer cells and therapeutic implications" Drug Resistance Updates (2004) vol. 7, pp. 97-110.
Piekarz et al., "Epigenetic modifiers: basic understanding and clinical development" Clin. Cancer Res. (2009) vol. 15, pp. 3918-3926.
Powis et al., "Thioredoxin signaling as a target for cancer therapy" Current Opinion in Pharmacology (2007) vol. 7, pp. 392-397.
Qi et al., "Siah2-dependent concerted activity of HIF and FoxA2 regulates formation of neuroendocrine phenotype and neuroendocrine prostate tumors" Cancer Cell (2010) vol. 18, No. 1, pp. 23-38.
Qiao et al., "Thiostrepton is an inducer of oxidative and proteotoxic stress that impairs viability of human melanoma cells but not primary melanocytes" Biochemical Pharmacology (2012) vol. 83, pp. 1229-1240.
Raj et al., "Selective killing of cancer cells by a small molecule targeting the stress response to ROS" Nature (2011) vol. 475, pp. 231-234.
Ramanathan et al., "Resistance to Paclitaxel Is Proportional to Cellular Total Antioxidant Capacity" Cancer Research (2005) vol. 65, pp. 8455-8460.
Rico et al., "Reactivity of the Perhalogenoalkanes CF2BrX (X=Cl, Br) with Nucleophiles. Part 4. Condensation with Carbanions" Journal of the Chemical Society, Perkin Transactions I, Organic and Bio-organic Chemistry (1982) vol. 4, pp. 1063-1065.
Robinson et al., "Selective fluorescent imaging of superoxide in vivo using ethidiumbased Probes" Proceedings of the National Academy of Sciences (2006) vol. 103, No. 41, pp. 15038-15043.
Rodriquez et al. "Total Synthesis, NMR Solution Structure, and Binding Model of the Potent Histone Deacetylase Inhibitor FR235222" Angew. Chem. Int. Ed. (2006) vol. 45, pp. 423-427.
Rogakou et al., "DNA double-stranded breaks induce histone H2AX phosphorylation on serine 139" Journal of Biological Chemistry (1998) vol. 273, pp. 5858-5868.
Rozen et al., "Bromochlorodifluoromethane" e-EROS Encyclopedia of Reagents for Organic Synthesis (2001). (4 pages).
Rushworth et al., "The high Nrf2 expression in human acute myeloid leukemia is driven by NF-kB and underlies its chemoresistance" Blood (2012) vol. 120, No. 26, pp. 5188-5198.
Santagata et al., "Using the Heat-Shock Response to Discover Anticancer Compounds that Target Protein Homeostasis" ACS Chemical Biology (2012) vol. 7, No. 2, pp. 340-349.
Saydam et al., "Determination of glutathione, glutathione reductase, glutathione peroxidase and glutathione S-transferase levels in human lung cancer tissues" Cancer Letters (1997) vol. 119, pp. 13-19.
Schaeffer et al., "Androgen-induced programs for prostate epithelial growth and invasion arise in embryogenesis and are reactivated in cancer" Oncogene (2008) vol. 27, pp. 7180-7191.
Schopfer et al., "Formation and Signaling Actions of Electrophilic Lipids" Chemical Reviews (2011) vol. 111, No. 10, pp. 5997-6021.
Schumacker "Reactive Oxygen species in cancer cells: Live by the sword, die by the Sword" Cancer Cell (2006) vol. 10, pp. 175-176.
Shimojo et al., "Attenuation of reactive oxygen species by antioxidants suppresses hypoxia-induced epithelial-mesenchymal transition and metastasis of pancreatic cancer cells" Clin Exp Metastasis (2012) vol. 30, pp. 143-154.
Shinji et al., "Design, synthesis, and evaluation of cyclic amide/imide-bearing hydroxamic acid derivatives as class-selective histone deacetylase (HDAC) inhibitors" Bioorganic & Medicinal Chemistry (2006) vol. 14, pp. 7625-7651.
Shoemaker, "The NCI60 human tumour cell line anticancer drug screen" Nat Rev Cancer. (2006) vol. 6, pp. 813-823.
Sigalotti et al., "Epigenetic modulation of solid tumors as a novel approach for cancer immunotherapy" Semin. Oncol. (2005) vol. 32, pp. 473-478.
Singh et al., "Dysfunctional KEAP1-NRF2 Interaction in Non-Small-Cell Lung Cancer" PLoS Med (2006) vol. 3, No. 10, p. e420. (12 pages).
Sporn et al., "Nrf-2 and cancer: the good, the bad and the importance of context" Nature Reviews Cancer (2012) vol. 12, pp. 564-571.
Szatrowski et al., "Production of large amounts of hydrogen peroxide by human tumour cells" Cancer Research (1991) vol. 51, pp. 794-798.
Taguchi et al., "Molecular mechanisms of the Keap1-Nrf2 pathway in stress response and cancer evolution" Genes to Cells (2011) vol. 16, No. 2, pp. 123-140.
Tew, et al., "Redox platforms in cancer drug discovery and development" Current Opinion in Chemical Biology (2011) vol. 15, pp. 156-161.
Thayer, "Fabulous Fluorine" Chem. Eng. News (2006) vol. 84, No. 23, pp. 15-24.
Thomsen et al., "Sox9 is required for prostate development" Dev. Biol. (2008a) vol. 316, pp. 302-311.
Thomsen et al., "The role of Sox9 in prostate development" Differentiation (2008b) vol. 76, pp. 728-735.
Thomsen et al., "SOX9 elevation in the prostate promotes proliferation and cooperates with PTEN loss to drive tumor formation" Cancer Res. (2010) vol. 70, No. 3, pp. 979-987, plus Correction, 2 pages.
Tochhawng et al., "Redox regulation of cancer cell migration and invasion" Mitochondrion (2013) vol. 13, pp. 246-253.
Trachootham et al., "Selective killing of oncogenically transformed cells through a ROS-mediated mechanism by beta-pheylethyl isothiocyanate" Cancer Cell (2006) vol. 10, pp. 241-252.
Trachootham et al., "Redox Regulation of Cell Survival" Antioxidants and Redox Signaling (2008) vol. 10, No. 8, pp. 1343-1374.

(56) References Cited

OTHER PUBLICATIONS

Trachootham et al., "Targeting cancer cells by ROS-mediated mechanisms: a radical therapeutic approach?" Nat Rev / Drug Discov (2009) vol. 8, pp. 579-591.
Vakifahmetoglu et al., "Death through a tragedy: mitotic catastrophe" Cell Death Differentiation (2008) vol. 15, pp. 1153-1162.
Vizniowski et al., "Propargyl Chlorides as Sources for Cabal Stabilized gamma-Carbonyl Cations" Journal of Org. Chemistry (1995), vol. 60, pp. 7496-7502.
Wahnon et al., "Mechanism-based Inhibition of an Essential Bacterial Adenine DNA Methyltransferase: Rationally Designed Antibiotics" J. Am. Chem. Soc. (2001) vol. 123, pp. 976-977.
Walker et al., "Do molecularly targeted agents in oncology have reduced attrition rates?" Nat Rev Drug Discov. (2009) vol. 8, No. 1, pp. 15-16.
Yang et al., "SOX9 is expressed in normal prostate basal cells and regulates androgen receptor expression in prostate cancer cells" Cancer Res. (2007) vol. 67, No. 2, pp. 528-536.
Wang et al., "SOX9 is expressed in human fetal prostate epithelium and enhances prostate cancer invasion" Cancer Res. (2008) vol. 68, pp. 1625-1630.
Wild et al., "Regulation of γ-glutamylcysteine synthetase subunit gene expression: insights into transcriptional control of antioxidant defenses" Free Radical Research (2000) vol. 32, No. 4, pp. 281-301.
Wondrak "Redox-Directed Cancer Therapeutics: Molecular Mechanisms and Opportunities" Antioxidants and Redox Signaling (2009) vol. 11, No. 12, pp. 3013-3069.
Workman et al., "Minimally Invasive Pharmacokinetic and Pharmacodynamic Technologies in Hypothesis-Testing clinical Trials of Innovative Therapies" J Natl Cancer Inst. (2006) vol. 98, No. 9, pp. 580-598.
Wu "The signaling mechanism of ROS in tumor progression" Cancer Metastasis Rev (2006) vol. 25, pp. 695-705.
Xu et al., "Difluoroallenyl Bromide as a Wide-Ranging Difluoromethylene Cation Equivalent: SN2 Substitution of Difluoropropargyl Bromide through Sequential SE2' and SN2' Reactions" Angewandte Chemie International Edition (2005) vol. 44, pp. 7404-7407.
Xu et al., "A new convenient synthesis of propargylic fluorohydrins and 2,5-diunsubstituted furans form fluoropropargyl chloride" J. Org. Chem. (2006a) vol. 71, pp. 3518-3521.
Xu et al., "An Efficient Synthesis of Diflluoropropargyl Bromides" Synthesis (2006b) vol. 5, pp. 803-806.
Yanai et al., "Indium(III) triflate catalyzed tandem azidation/1,3-dipolar cycloaddition reaction of omega,omega-dialkoxyalkyne derivatives with trimethylsilyl azide" Tetrahedron Letters (2005) vol. 46, pp. 8639-8643.
Yang et al., "Targeting DNA methylation for epigenetic therapy" Trends Pharmacol. Sci. (2010) vol. 31, No. 11, pp. 536-546.
Yang et al., "Selective targeting of breast cancer cells through ROS-mediated mechanisms potentiates the lethality of paclitaxel by a novel diterpene, gelomulide K" Free Radical Biology & Medicine (2011) vol. 51, pp. 641-657.
Yoo et al., "Epigenetic therapy of cancer: past, present and future" Nat Rev Drug Discov. (2006) vol. 5, pp. 37-50.
Young et al., "Activation of Antioxidant Pathways in Ras-Mediated Oncogenic Transformation of Human Surface Ovarian Epithelial Cells Revealed by Functional Proteomics and Mass Spectrometry" Cancer Research (2004) vol. 64, pp. 4577-4584.
Alexandre et al., "Bypasses of the antimycin a block of mitochondrial electron transport in relation to ubisemiquinone function" Biochimica et Biophysica Acta (BBA)—Bioenergetics (1984) vol. 767, No. 1, pp. 120-129.
Boveris "Mitochondrial Production of Superoxide Radical and Hydrogen Peroxide" at pp. 67-82 in Advances in Experimental Medicine and Biology, vol. 78 Tissue Hypoxia and Ischemia, Editors Reivich et al. (1977) Plenum Press, New York and London.
Byun et al., "Conformational preferences and pKa value of selenocysteine residue" Biopolymers (2011) vol. 95, No. 5, pp. 345-353.
Oberley et al., "Antioxidant Enzyme Levels in Cancer" Histology and Histopathology (1997) vol. 12, pp. 525-535.
Parkinson et al., "Runaway ROS as a Selective Anticancer Strategy" ChemMedChem (2011) vol. 6, pp. 1957-1959.
Plummer et al., "Chemical Depletion of Glutathione in vivo" Methods in Enzymology (1981) vol. 77, pp. 50-59.
Semlitsch et al., "Differential influence of the lipid peroxidation product 4-hydroxynonenal on the growth of human lymphatic leukaemia cells and human periopherial blood lymphocytes" Anticancer Research (2002) vol. 22, No. 3, pp. 1689-1697.
Alexandre et al., "Improvement of the therapeutic index of anticancer drugs by the superoxide dismutase mimic mangafodipir" Journal of the National Cancer Institute (2006) vol. 98, No. 4, pp. 236-244.
Altschul et al., "Gapped Blast and PSI-Blast: a new generation of protein database search programs" Nucleic Acids Research (1997) vol. 25, pp. 3389-3402.
American Cancer Society. Cancer Facts and Figures 2010. (68 pages).
Andre et al., "Oxalipalatin, Fluorouracil, and Leucovorin as Adjuvant Treatment for Colon Cancer" New England Journal of Medicine (2004) vol. 350, pp. 2343-2351.
Andrianasolo et al., "DNA methyl transferase inhibiting halogenated monoterpenes from the Madagascar red marine alga Portieria homemannii" J Nat Prod. (2006) vol. 69, No. 4, pp. 576-579.
Annunziata et al., "PARP inhibitors in BRCA1/BRCA2 germline mutation carriers with ovarian and breast cancer" Biol Rep. (2010) vol. 2, article 10. (4 pages).
Bahlis et al., "Feasibility and Correlates of Arsenic Trioxide Combined with Ascorbic Acid-mediated Depletion of Intracellular Glutathione for the Treatment of Relapsed/Refractory Multiple Myeloma" Clinical Cancer Research (2002) vol. 8, No. 12, pp. 3658-3668.
Baniwal et al., "Runx2 transcriptome of prostate cancer cells: insights into invasiveness and bone metastasis" Mol. Cancer (2010) vol. 9, article 258. (18 pages).
Battioni et al., "3-Lithiopropargyl halides as alkynylating reagents" Bullentin De Las Societe Chimique de France (1969) No. 3, pp. 911-914. (English language abstract attached).
Benaim et al., "Reactions of acetylene chlorohydrin with complex anions of molybdenum and manganese; formation of eta.3-bonded .alpha.-methylenelactones" Journal of Organometallic Chemistry (1979) vol. 165, No. 2, pp. C28-C32.
Bessard et al. "Ring Opening of gem-Dihalocyclopropanes: Novel Types of 1, 4 Elimination Reactions" Tetrahedron (1990) vol. 46, No. 15, pp. 5230-5236.
Bijur et al., "Antimutagenic and promutagenic activity of ascorbic acid during oxidative stress" Environ. Mol. Mutagen (1997) vol. 30, pp. 339-345.
Bonkhoff et al., "From pathogenesis to prevention of castration resistant prostate cancer" Prostate (2010) vol. 70, No. 1, pp. 100-112.
Brillon et al., "Synthesis of 11-and 12-membered rings by direct cyclization method" Canadian Journal of Chemistry (1987) vol. 65, No. 43, pp. 43-55.
Buck et al., "Alkylation of 1-alkynes in THF" Tehedron Letters (2001) vol. 42, pp. 5825-5827.
Budman et al., "Identification of potentially useful combinations of epidermal growth factor receptor tyrosine kinase antagonists with conventional cytotoxic agents using median effect analysis" Anticancer Drugs (2006) vol. 17, No. 8, pp. 921-928.
Burton et al., "A Facile General route to Perfluoroalkyl Allenes" Tetrahedron Letters (1990) vol. 31, No. 26, pp. 3699-3702.
Butler et al., "Histone deacetylase inhibitors as therapeutics for polyglutamine disorders" Nature Reviews: Neuroscience (2006) vol. 7, pp. 784-796.
Byun et al., "Conformational Preferences of Helix Foldamers of γ-Peptides Based on 2-(Aminomethyl) cyclohexanecarboxylic Acid" Biopolymers (2013) vol. 101, No. 1, pp. 87-95.
Cai et al., "Small molecule inhibitors of mammalian thioredoxin reductase" Free Radical Biology and Medicine (2012) vol. 52, pp. 257-265.

(56) References Cited

OTHER PUBLICATIONS

Chakravarty et al., "Prognostic significance of cytoplasmic SOX9 in invasive ductal carcinoma and metastatic breast cancer" Exp. Biol. Med. (2011) vol. 236, pp. 145-155.

Cole et al., "The EBV-Hybridoma Technique and Its Application to Human Lung Cancer" from UCLA Symposia on Molecular and Cellular Biology New Series, vol. 27, Section II—Human-Human Hybridomas, [Roche-UCLA Symposium on "Monoclonal Antibodies and Cancer Therapy"] (Copyright 1985) Alan R. Liss, Inc., New York, NY, pp. 77-96.

Cox, George W., "Assay for Macrophage-Mediated Anti-Tumor Cytotoxicity" from Current Protocols in Immunology, Supplement 84 (1994) Edited by Coligan et al. (Copyright 1994) John Wiley & Sons, Inc., Hoboken, NJ, Units 14.7.1-14.7.10.

DeJeans et al., "Overexpression of GRP94 in breast cancer cells resistant to oxidative stress promotes high levels of cancer cell proliferation and migration: Implications for tumor recurrence" Free Radical Biology and Medicine (2012) vol. 52, pp. 993-1002.

Deng et al., "Studies on Highly Steroselective Addition—Elimination Reactions of 3-(Methoycarbonyl)-1,2-allen-4-ols with MX. An Efficient Synthesis of 3-(Methoxycarbonyl)-2-halo-1, 3(Z)-dienes" Journal of Organometallic Chemistry (2007) vol. 72, pp. 5901-5904.

Deponte "Glutathione catalysis and the reaction mechanisms of glutathione-dependent enzymes" Biochimica et Biophysica Acta—Cellular functions of glutathione (BBA) (2013) vol. 1830, pp. 3217-3266.

Dickhout et al., "Integrated Stress Response Modulates Cellular Redox State via Induction of Cystathionine gamma-lyase: Crosstalk between integrated stress response and thiol metabolism" Journal of Biological Chemistry (2012) vol. 287, No. 10, pp. 7603-7614.

Donnelly et al., "The elF2α kinases: their structures and functions" Cellular and Molecular Life Sciences (2013) vol. 70, pp. 3493-3511.

Dudley et al., "Calcification of multipotent prostate tumor endothelium" Cancer Cell (2008) vol. 14, No. 3, pp. 201-211.

Ellman "Tissue sulfhydryl groups" Archives of Biochemistry and Biophysics (1959) vol. 82, No. 1, pp. 70-77.

Evano, "Product subclass 9: alk-2-ynoic acids" Science of Synthesis (2006) vol. 20a, pp. 507-531.

Feixas et al., "Synthesis of (Z)-10, 10-Difluoro-13-Hexadecen-11-YNYL Acetate, New Difluoro Analogue of the Sex Pheromone of the Processionary Moth" Bioorganic & Medicinal Chemistry Letters (1992) vol. 2, No. 5, pp. 467-470.

Forkink et al., "Detection and manipulation of mitochondrial reactive oxygen species in mammalian cells" Biochimica et Biophysica Acta (BBA)—Bioenergetics (2010) vol. 1797, pp. 1034-1044.

Fuchs et al., "Targeting Recombinant Antibodies to the Surface of *Escherichia coli*: Fusion to a Peptidoglycan Associated Lipoprotein" BioTechnology (1991) vol. 9, pp. 1369-1372.

Fukai et al., "Superoxide dismutases: role in redox signaling, vascular function, and diseases" Antioxid & Redox Signal (2011) vol. 15, No. 6, pp. 1583-1606.

Fuller et al., "Isolation and structure/activity features of halomon-related antitumor monoterpenes from the red alga Portieria hornemannii" J Med Chem. (1994) vol. 37, pp. 4407-4411.

Garcia-Dominguez et al., "Total synthesis of the proposed structures of the DNA methyl transferase inhibitors peyssonenynes, and structural revision of peyssonenyne B" Org. Biomol. Chem. (2011) vol. 9, pp. 6979-6987.

Gillmann et al., "Convenient Synthesis of Methyl 2-Bromo-and 2-Iodo-2, 3-Butadiennoates" Synthetic communications (1994) vol. 24, No. 15, pp. 2133-2138.

Girvan et al., "AGRO100 inhibits activation of nuclear factor-kB (NF-kB) by forming a complex with NF-kB essential modulator (NEMO) and nucleolin" Molecular Cancer Therapeutics (2006) vol. 5, No. 7. pp. 1790-1799.

Goffin et al., "DNA methyltransferase inhibitors-state of the art" Annals of Oncology (2002) vol. 13, pp. 1699-1716.

Griffin et al., "Potent and specific inhibition of glutathione synthesis by buthionine sulfoximine (S-n-butyl homocysteine sulfoximine)" Journal of Biological Chemistry (1979) vol. 254, pp. 7558-7560.

Griffiths et al., "Human anti-self antibodies with high specificity from phage display libraries" EMBO J. (1993) vol. 12, No. 2, pp. 725-734.

Gushchin et al., "Iodine-127 NQR spectra in a series of iodo derivatives of aliphatic compounds" Izvestiya Akademii Nauk SSSR (1983) vol. 8, pp. 1920-1922. (published English Translation of original article in Russian language).

Hallock et al., "Antitumor activity and stereochemistry of acetylenic alcohols from the sponge Cribrochalina vasculum" Journal of Natural Products (1995) vol. 58, No. 12, pp. 1801-1807.

Hammond, "Nucleophilic and electrophilic substitutions of difluoropropargyl bromides" Journal of Fluorine Chemistry (2006) vol. 127, pp. 476-488.

Hamper "Regioselective Synthesis of 1-Methyl-3Hydroxy-5-perfluoroalkylpyrazoles by the Addition of Methylhydrazine to Perfluoroalkylacetylenic Esters" Journal of Fluorine Chemistry (1990) vol. 48, pp. 123-131.

Hassane et al., "Discovery of agents that eradicate leukemia stem cells using an in silico screen of public gene expression data" Blood (2008) vol. 111, No. 12, pp. 5654-5662.

\* cited by examiner

| U937 | Veh | BSO+DEM | XB05 | XB05 + GSH |
|---|---|---|---|---|
| EXPT #1 AVG RLU | 407999 | 47185 | 108239 | 388280 |
| EXPT #2 AVG RLU | 360364 | 70732 | 88172 | 355595 |
| EXPT #3 AVG RLU | 597954 | 43849 | 95374 | 584881 |
| AVG | 455439 | 53922 | 97262 | 442918 |
| STD DEV | 125698 | 14653 | 10165 | 124024 |
| STD Error | 72572 | 8459 | 5869 | 71605 |
| Normalized to Veh | 100 | 11.84 | 21.35 | 97.25 |
| Norm STD Error | 15.93 | 1.86 | 1.28 | 15.72 |
| | | | | |
| % Change | | -88.16 | -78.64 | -2.75 |

B)

| A549 | Veh | BSO+DEM | XB05 | XB05 + GSH |
|---|---|---|---|---|
| EXPT #1 AVG RLU | 2910499 | 39160 | 3694680 | 3119574 |
| EXPT #2 AVG RLU | 3678726 | 138840 | 4962395 | 3461568 |
| EXPT #3 AVG RLU | 3779358 | 153587 | 5100802 | 4175586 |
| AVG | 3456194 | 110529 | 4585959 | 3585576 |
| STD DEV | 475256 | 62245 | 774966 | 538817 |
| STD Error | 274389 | 35937 | 447427 | 311086 |
| Normalized to Vehicle | 100 | 3.19 | 132.68 | 103.74 |
| Norm STD Error | 7.93 | 1.04 | 12.95 | 9.00 |
| | | | | |
| % Change | | -96.80 | 32.68 | 3.74 |

C)

| Hs27 | Veh | BSO+DEM | XB05 | XB05 + GSH |
|---|---|---|---|---|
| EXPT #1 AVG RLU | 2101840 | 51364.667 | 4380455 | 2200190 |
| EXPT #2 AVG RLU | 2068076 | 68414.333 | 4270995 | 2047438 |
| EXPT #3 AVG RLU | 2048981 | 60900 | 4347948 | 2216811 |
| AVG | 2072966 | 60226 | 4333133 | 2154813 |
| STD DEV | 26766 | 8544 | 56213 | 93359 |
| STD Error | 15453 | 4933 | 32455 | 53901 |
| Normalized to Vehicle | 100 | 2.90 | 209.03 | 103.94 |
| Norm STD Error | 0.74 | 0.24 | 1.56 | 2.60 |
| | | | | |
| % Change | | -97.04 | 109.03 | 3.94 |

Figure 15
A)
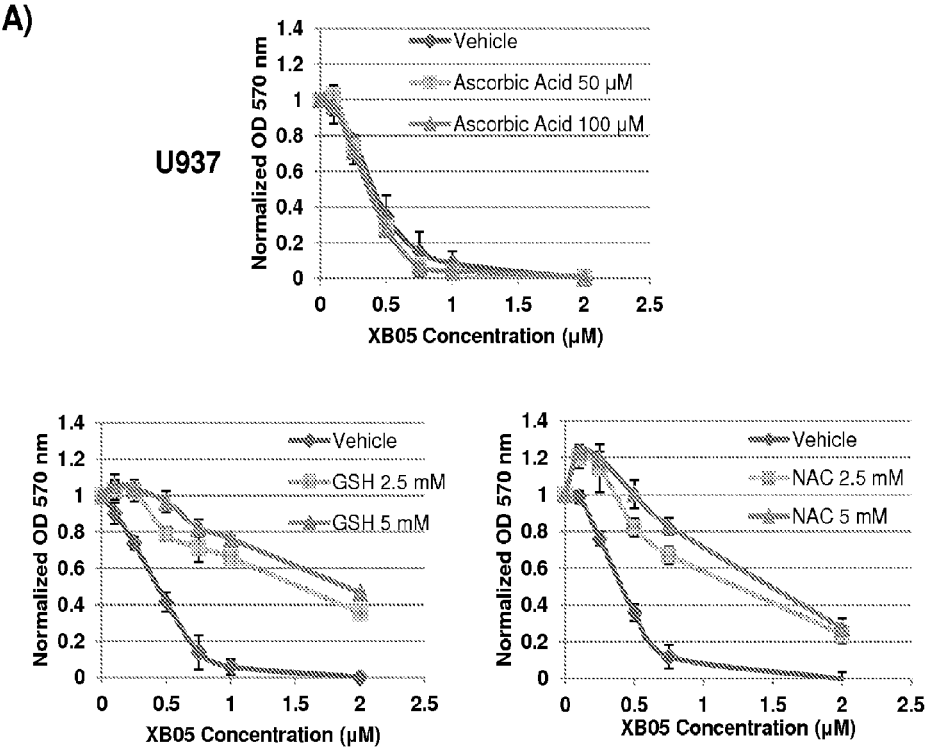
B)
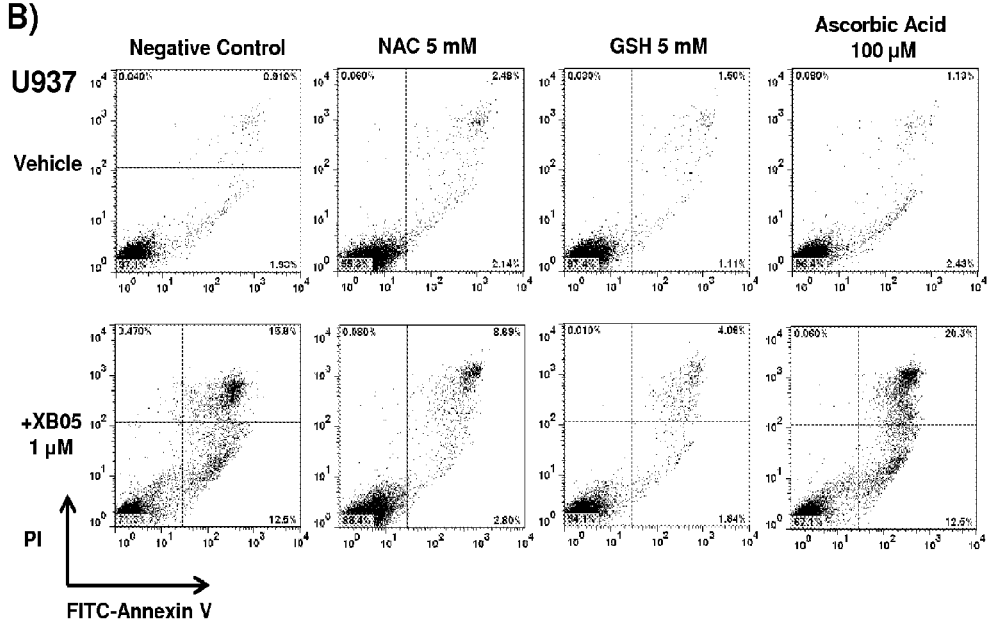

Figure 18

E    Reactivity of XB05 with amino acids and reduced glutathione monitored by $^{19}$F and $^{1}$H NMR

| Compounds | 1 hr | 24 hrs | 72 hrs |
|---|---|---|---|
| Cysteine | No reaction | Ca. 10% conversion of XB05 | Ca. 15% conversion of XB05 |
| Lysine | No reaction | No reaction | No reaction |
| Histidine | No reaction | No reaction | No reaction |
| Arginine | No reaction | No reaction | No reaction |
| Reduced Glutathione | No reaction | Ca. 20% conversion of XB05 | Ca. 50% conversion of XB05 |

F

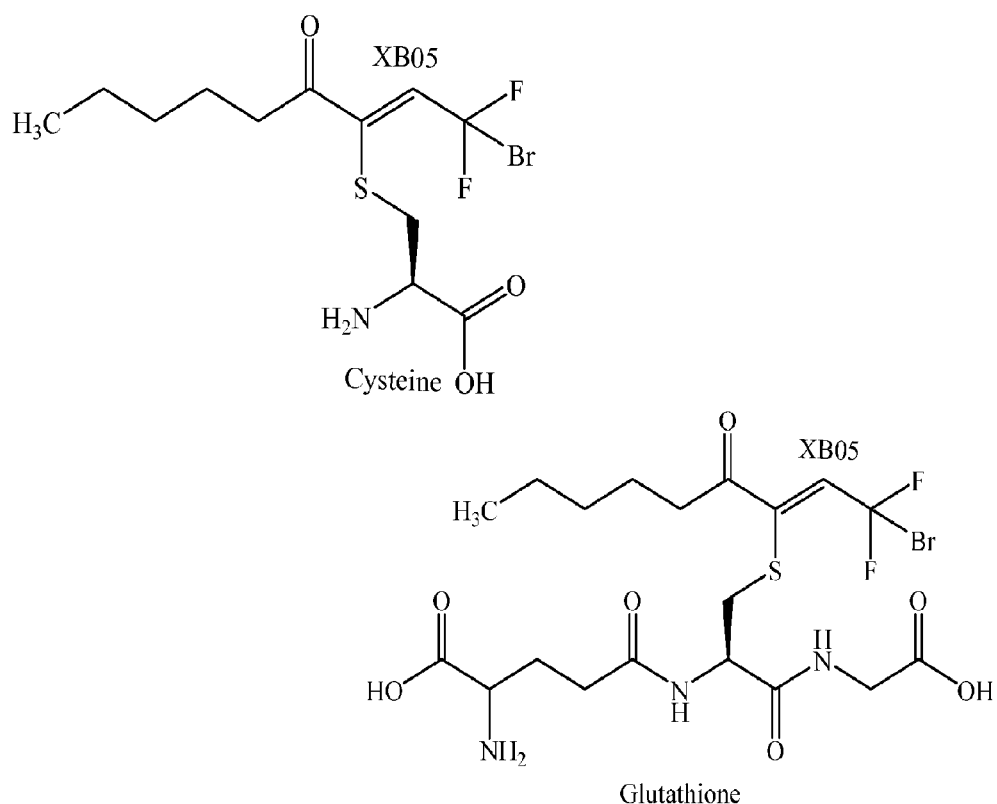

COMPOSITIONS AND METHODS FOR MODULATING DNMT1 INHIBITOR ACTIVITY

CROSS-REFERENCE TO RELATED APPLICATIONS

This application is a National Stage Entry of International Application No. PCT/US2013/058566 filed Sep. 6, 2013, which is herein incorporated by reference in its entirety, which claims the benefit of (a) U.S. Provisional Application No. 61/698,403, filed Sep. 7, 2012, which is herein incorporated by reference in its entirety and (b) U.S. Provisional Application No. 61/786,705, filed Mar. 15, 2013, which is herein incorporated by reference in its entirety.

BACKGROUND

Diseases continue to plague animals, such as humans. For example, cancer is a prevalent disease and can be found in many different, albeit sometimes related forms. Treatment of diseases, such as cancer, can sometimes include administration of toxic or lethal doses of drugs; in some instances, additional treatment (e.g., administration of other drugs) can attenuate the disease treatment (e.g., by attenuating the toxicity or lethality of the originally administered disease-treating drug). Accordingly, some embodiments of the invention include methods for treating diseases (such as cancer) including methods to attenuate the disease treatment. Other embodiments of the invention include compositions for treating diseases (such as cancer) including compositions to attenuate disease treatment. Additional embodiments of the invention are also discussed herein.

SUMMARY

Some embodiments of the invention include methods for attenuating the activity of a DNA (cytosine-5)-methyltransferase 1 (DNMT1) inhibitor, where the method comprises administering, to an animal who had previously been administered a DNMT1 inhibitor, a composition comprising an antioxidant. In other embodiments, the invention includes methods for attenuating the activity of a DNA (cytosine-5)-methyltransferase 1 (DNMT1) inhibitor, comprising administering to an animal a composition comprising a DNMT1 inhibitor and an antioxidant. In some instances, the animal is undergoing treatment for cancer In certain embodiments, the antioxidant is a thiol-based antioxidant, such as N-acetytl cysteine or glutathione. In certain embodiments, the DNMT1 inhibitor is a compound of Formula (I), a compound of Formula (II), XB05a, XB05b, or XB05.

Some embodiments of the invention include compositions comprising a DNMT1 inhibitor (e.g., a compound from Formula (I), a compound of Formula (II), XB05a, XB05b, or XB05) and an antioxidant (e.g., thiol-based antioxidant, such as N-acetytl cysteine or glutathione). Still other embodiments of the invention include methods for treating an animal comprising administering to the animal a composition comprising a DNMT1 inhibitor and an antioxidant.

Other embodiments of the invention are discussed herein.

BRIEF DESCRIPTION OF THE DRAWINGS

The following drawings form part of the present specification and are included to further demonstrate certain aspects of the present invention. The invention may be better understood by reference to one or more of these drawings in combination with the description of specific embodiments presented herein.

FIG. 9: GSH-Glo Assay Raw RLU Values. The GSH-Glo™ assay was conducted as described in Methods. Tables A-C contain average RLU values (averaged from triplicate wells) for 3 independent experiments in each cell line. Data is plotted as % change in GSH levels in FIG. 8

FIG. 15: Thiol-based Antioxidants Inhibit the Antiproliferative and Cytotoxic Effects of XB05 in U937 cells. (A) MTT proliferation assays for U937 cells treated with XB05 in combination with antioxidants ascorbic acid (AA), reduced glutathione (GSH) and N-acetyl cysteine (NAC) as indicated for 72 h. (B) Flow cytometric analysis of Annexin/PI staining for U937 cells treated with vehicle or XB05+/−antioxidants as indicated for 72 h. Data shown are representative of three independent experiments.

DETAILED DESCRIPTION

Figure 1:
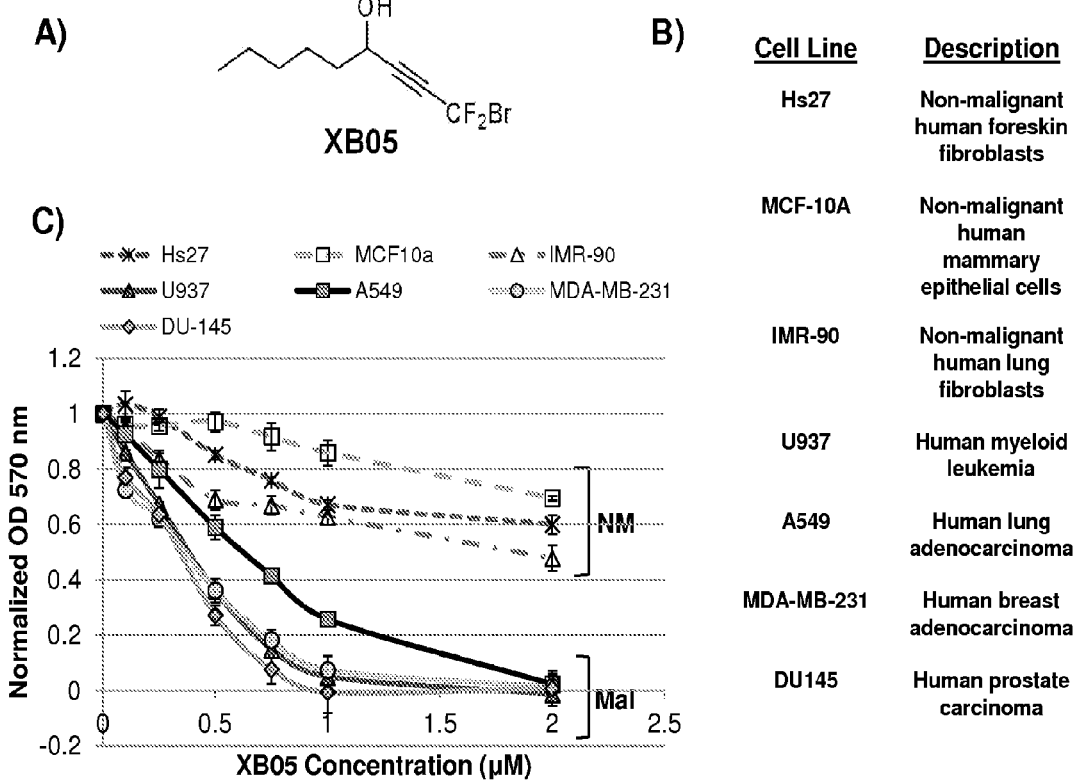
FIG. 1: XB05 has Cancer-selective Antiproliferative Activity. (A) The chemical structure of XB05. (B) Human non-malignant (NM) and malignant (Mal) cell lines in which XB05 antiproliferative activity was tested. (C) Cells were treated with the indicated concentrations of XB05 for 72 h and proliferation was assessed using MTT assays. Results were normalized to untreated controls for each cell line. Data points represent the mean+/−standard error of the mean (SEM) for three independent experiments. Statistical comparisons between non-malignant and malignant cell lines with the same tissue of origin were conducted. Statistically significant differences were observed between A549 and IMR-90 at 0.75, 1 and 2 µM XB05 (p≤0.05) and between MDA-MB-231 and MCF-10A at all XB05 concentrations tested (p≤0.01).

Some embodiments of the invention include methods comprising attenuating the activity of a DNA (cytosine-5)-methyltransferase 1 (DNMT1) inhibitor including, but not limited to, the step of administering a composition comprising an antioxidant to an animal who had previously been administered a DNMT1 inhibitor. Certain embodiments of the invention include methods comprising administering a composition comprising a DNMT1 inhibitor and an antioxidant, and does not require that a DNMT1 inhibitor be administered to the animal prior to administering the composition. Other embodiments include compositions comprising a DNMT1 inhibitor and an antioxidant.

In some embodiments, the animal is a human (e.g., a human patient) or livestock. In some instances the animal can be a mammal or a primate. In some examples, the animal is a pig, a cow, a horse, a dog, a cat, or a human. In some embodiments, the animal is a male. In some embodiments, the animal is a female. In some embodiments, the animal is a child, a teenager, or an adult (e.g., at least 18, 20, 25, 30, 35, 40, 45, 50, 55, 60, 65, 70, 75, 80, 85, 90, or 95 years old).

In some embodiments, the antioxidant can be one or more of glutathione, N-acetyl cysteine, dihydrolipoate, cysteamine, or ascorbic acid. The antioxidant can be a thiol-based antioxidant, such as but not limited to glutathione, cysteine, N-acetyl cysteine, dihydrolipoate, D-ribose-L-cysteine, cysteamine, erdosteine, thiols of erdosteine, methionine, or thiols of methionine. The antioxidant can be as non-thiol-based antioxidant, such as but not limited to ascorbic acid, vitamin A, or a vitamin E. In certain embodiments, the antioxidant does not include non-thiol-based antioxidants, such as ascorbic acid, vitamin A, or a vitamin E.

The term "attenuating" (and its variations) used with DNMT1 inhibitor activity is meant to include any effect that acts as an inhibitor of DNMT1 inhibitor activity or acts to otherwise reduce DNMT1 inhibitor activity. DNMT1 inhibitor activity can include any activity influenced directly or indirectly by a DNMT1 inhibitor, including but not limited to cytotoxicity, ability to proliferate, cellular oxidative stress, reactivity with a cellular thiol, or DNA damage. The attenuation of DNMT1 inhibitor activity can result in an increase in DNMT1 activity, can result in the modulation (e.g., increase or decrease) of other enzyme activity (by any direct or indirect mechanism), can result in the modulation (e.g., increase or decrease) of cellular activity (by any direct or indirect mechanism), or a combination thereof. Attenuation is not intended to require complete cessation of DNMT1 activity. Such attenuation can be by at least about 50%, at least about 75%, at least about 90%, and at least about 95% of the activity in the absence of the attenuation effect, e.g., in the absence of the antioxidant. The term can refer to an observable or measurable attenuation in DNMT1 inhibitor activity. In certain embodiments of treatment scenarios, the attenuation can be sufficient to produce a therapeutic and/or prophylactic benefit in the condition or disease (e.g., cancer) being treated. The phrase "does not attenuate" and its grammatical conjugations do not require a complete lack of effect on the DNMT1 inhibitor activity. For example, it can refer to situations where there is less than about 20%, less than about 10%, and less than about 5% of attenuation in DNMT1 inhibitor activity in the presence of the antioxidant.

DNMT1 Inhibitors

By the term "DNA (cytosine-5)-methyltransferase 1 (DNMT1) inhibitor" is meant a molecule that decreases (e.g., a significant, observable, or detectable decrease) the activity of DNMT1 (e.g., decreases the activity of DNMT1 in an animal cell, e.g., a mammalian cancer cell). Non-limiting examples of DNMT1 inhibitors are described herein (e.g., XB05). Additional, non-limiting examples of DNMT1 inhibitors are described in Yang et al., *Trends Pharmacol.*

Sci. 31:536-546, 2010 (e.g., 5-azacytidine, 5-aza-2'-deoxycytidine, 5,6-dihydro-5-azacytidine, zebularine, 5-fluoro-2'-deoxycytidine, NPEOC-DAC, S110, hydralazine, RG108, procainamide, and SGI-1027). Additional examples of DNMT1 inhibitors are known in the art. Non-limiting examples of methods for determining the activity DNMT1 are described herein. Additional methods for determining the activity of DNMT1 are known in the art.

Non-limiting examples of DNMT1 inhibitors are described in U.S. Patent Application Publication No. 2008/0188570, which is incorporated by reference in its entirety. In some embodiments, a DNMT1 inhibitor can be a DNMT1 inhibitor of Formula (I)

(I)

wherein:

$R_1$ can be carboxy, $(C_1-C_{20})$alkoxycarbonyl, $(C_2-C_{20})$alkenyloxycarbonyl, $(C_2-C_{20})$alkynyloxycarbonyl, $(C_1-C_{20})$alkyl, $(C_2-C_{20})$alkenyl, or $(C_2-C_{20})$alkynyl, which $(C_1-C_{20})$alkyl, $(C_2-C_{20})$alkenyl, or $(C_2-C_{20})$alkynyl, can be substituted with one or more groups independently selected from halo, hydroxy, mercapto, $(C_1-C_{20})$alkoxy, $(C_2-C_{20})$alkenyloxy, $(C_2-C_{20})$alkynyloxy, aryloxy, heteroaryloxy, $(C_3-C_{20})$cycloalkyloxy, heterocyclyloxy, $(C_1-C_{20})$alkylthio, $(C_2-C_{20})$alkenylthio, $(C_2-C_{20})$alkynylthio, carboxy, $(C_1-C_{20})$alkoxycarbonyl, $(C_2-C_{20})$ alkenyloxycarbonyl, $(C_2-C_{20})$alkynyloxycarbonyl, aryl, heteroaryl, cycloalkyl, heterocyclyl, $NR_aR_b$, $(C_2-C_{20})$alkynoyloxy, and arylcarbonyloxy;

$R_2$ can be $CF_2Br$, $CFHBr$, $CF_2Cl$, $CFHCl$, $CFBr_2$, $CFCl_2$, $CBr_3$, $C(R_c)(R_d)Br$, $C(R_c)(R_d)Cl$, $CF(R_e)Br$, $CF_2I$, $CFHI$, $C(R_c)(R_d)I$, $CF(R_e)I$, or $CCl_3$;

each $R_a$ and $R_b$ can be independently H, $(C_1-C_{20})$alkyl, $(C_1-C_{20})$alkanoyl, $(C_2-C_{20})$ alkenylcarbonyl, $(C_2-C_{20})$alkynylcarbonyl, $(C_1-C_{20})$alkoxy, $(C_2-C_{20})$alkenyloxy, $(C_2-C_{20})$alkynyloxy, or aryl-$(C_1-C_{20})$alkoxycarbonyl;

each $R_c$ and $R_d$ can be independently H, $(C_1-C_{20})$alkyl, $(C_1-C_{20})$alkanoyl, $(C_2-C_{20})$alkenylcarbonyl, $(C_2-C_{20})$alkynylcarbonyl, $(C_1-C_{20})$alkoxy, $(C_2-C_{20})$alkenyloxy, or $(C_2-C_{20})$alkynyloxy; and $R_e$ can be $(C_1-C_{20})$alkyl, $(C_1-C_{20})$alkanoyl, $(C_2-C_{20})$alkenylcarbonyl, $(C_2-C_{20})$alkynylcarbonyl, $(C_1-C_{20})$alkoxy, $(C_2-C_{20})$alkenyloxy, or $(C_2-C_{20})$alkynyloxy; and, where each aryl, heteroaryl, heterocyclyl, aryloxy, heteroaryloxy, arylcarbonyloxy or heteroarylcarbonyloxy of $R_1$ can be optionally substituted with one or more groups independently selected from halo, hydroxy, nitro, cyano, trifluoromethyl, trifluoromethoxy, mercapto, carboxy, $(C_1-C_{20})$alkyl, $(C_2-C_{20})$alkenyl, $(C_2-C_{20})$alkynyl, $(C_1-C_{20})$alkoxy, $(C_2-C_{20})$alkenyloxy, $(C_2-C_{20})$alkynyloxy, $(C_1-C_{20})$alkylthio, $(C_2-C_{20})$alkenylthio, $(C_2-C_{20})$alkynylthio, $(C_1-C_{20})$alkoxycarbonyl, $(C_2-C_{20})$alkenyloxycarbonyl, $(C_2-C_{20})$alkynyloxycarbonyl, aryl, heteroaryl, aryl$(C_1-C_{20})$alkyl, heteroaryl$(C_1-C_{20})$alkyl, aryl$(C_2-C_{20})$alkenyl, aryl$(C_2-C_{20})$alkynyl, heteroaryl$(C_2-C_{20})$alkenyl, heteroaryl$(C_2-C_{20})$alkynyl, $(C_1-C_{20})$alkanoyloxy, $(C_2-C_{20})$alkenoyloxy, and $(C_2-C_{20})$alkynoyloxy.

Certain embodiments include a salt of Formula (I).

In some embodiments of Formula (I), $R_1$ can be carboxy, $(C_1-C_{20})$alkoxycarbonyl, $(C_2-C_{20})$alkenyloxycarbonyl, $(C_2-C_{20})$alkynyloxycarbonyl, $(C_1-C_{20})$alkyl, $(C_2-C_{20})$alkenyl, or $(C_2-C_{20})$alkynyl, which $(C_1-C_{20})$alkyl, $(C_2-C_{20})$alkenyl, or $(C_2-C_{20})$alkynyl, can be substituted with one or more groups independently selected from halo, hydroxy, mercapto, $(C_1-C_{20})$alkoxy, $(C_2-C_{20})$alkenyloxy, $(C_2-C_{20})$alkynyloxy, $(C_1-C_{20})$alkylthio, $(C_2-C_{20})$alkenylthio, $(C_2-C_{20})$alkynylthio, carboxy, $(C_1-C_{20})$alkoxycarbonyl, $(C_2-C_{20})$alkenyloxycarbonyl, $(C_2-C_{20})$alkynyloxycarbonyl, aryl, heteroaryl, and $NR_aR_b$;

$R_2$ can be $CF_2Br$, $CFHBr$, $CF_2Cl$, $CFHCl$, $CFBr_2$, $CFCl_2$, $CBr_3$, $C(R_c)(R_d)Br$, $C(R_c)(R_d)Cl$, $CF(R_e)Br$, or $CCl_3$, where each $R_a$ and $R_b$ can be independently H, $(C_1-C_{20})$alkyl, $(C_1-C_{20})$alkanoyl, $(C_2-C_{20})$alkenylcarbonyl, $(C_2-C_{20})$alkynylcarbonyl, $(C_1-C_{20})$alkoxy, $(C_2-C_{20})$alkenyloxy, or $(C_2-C_{20})$alkynyloxy;

each $R_c$ and $R_d$ can be independently H, $(C_1-C_{20})$alkyl, $(C_1-C_{20})$alkanoyl, $(C_2-C_{20})$alkenylcarbonyl, $(C_2-C_{20})$alkynylcarbonyl, $(C_1-C_{20})$alkoxy, $(C_2-C_{20})$alkenyloxy, or $(C_2-C_{20})$alkynyloxy; and $R_e$ can be $(C_1-C_{20})$alkyl, $(C_1-C_{20})$alkanoyl, $(C_2-C_{20})$alkenylcarbonyl, $(C_2-C_{20})$alkynylcarbonyl, $(C_1-C_{20})$alkoxy, $(C_2-C_{20})$alkenyloxy, or $(C_2-C_{20})$alkynyloxy; and, where each aryl or heteroaryl of $R_1$ can be optionally substituted with one or more groups independently selected from halo, hydroxy, nitro, cyano, trifluoromethyl, trifluoromethoxy, mercapto, carboxy, $(C_1-C_{20})$alkyl, $(C_2-C_{20})$alkenyl, $(C_2-C_{20})$alkynyl, $(C_1-C_{20})$alkoxy, $(C_2-C_{20})$alkenyloxy, $(C_2-C_{20})$alkenyloxy, $(C_1-C_{20})$alkylthio, $(C_2-C_{20})$alkenylthio, $(C_2-C_{20})$alkynylthio, $(C_1-C_{20})$alkoxycarbonyl, $(C_2-C_{20})$alkenyloxycarbonyl, $(C_2-C_{20})$alkynyloxycarbonyl, aryl, heteroaryl, aryl$(C_1-C_{20})$alkyl, heteroaryl$(C_1-C_{20})$alkyl, aryl$(C_2-C_{20})$alkenyl, aryl$(C_2-C_{20})$alkynyl, heteroaryl$(C_2-C_{20})$alkenyl, heteroaryl$(C_2-C_{20})$alkynyl, $(C_1-C_{20})$alkanoyloxy, $(C_2-C_{20})$alkenoyloxy, and $(C_2-C_{20})$alkynoyloxy.

In still other embodiments, the DNMT1 inhibitor is not 4-bromo-4,4-difluorobut-2-ynoic acid, 1-bromo-1,1-difluoro-non-2-yn-4-ol, or 6-bromo-6,6-difluoro-2-methylhex-4-yn-3-ol.

In some instances of Formula (I), $R_1$ can be a $(C_1-C_{20})$alkyl, $(C_2-C_{20})$alkenyl, or $(C_2-C_{20})$alkynyl, which $(C_1-C_{20})$alkyl, $(C_2-C_{20})$alkenyl, or $(C_2-C_{20})$alkynyl can be substituted with hydroxy, mercapto, carboxy, or $NR_aR_b$.

In other instances of Formula (I), $R_1$ can be a $(C_1-C_{20})$alkyl, $(C_2-C_{20})$alkenyl, or $(C_2-C_{20})$alkynyl, which $(C_1-C_{20})$alkyl, $(C_2-C_{20})$alkenyl, or $(C_2-C_{20})$alkynyl can be substituted with hydroxy.

In yet other instances of Formula (I), $R_1$ can be a $(C_1-C_{20})$alkyl, $(C_2-C_{20})$alkenyl, or $(C_2-C_{20})$alkynyl, which $(C_1-C_{20})$alkyl, $(C_2-C_{20})$alkenyl, or $(C_2-C_{20})$alkynyl can be substituted on the carbon adjacent to the triple bond in Formula (I) with hydroxy.

In some embodiments of Formula (I), $R_1$ can be a $(C_5-C_{10})$alkyl, $(C_2-C_{10})$alkenyl, or $(C_2-C_{10})$alkynyl that can be substituted with hydroxy, mercapto, carboxy or $NR_aR_b$; or $R_1$ can be a $(C_5-C_{10})$alkyl, $(C_2-C_{10})$alkenyl, or $(C_2-C_{10})$alkynyl that can be substituted with hydroxyl; or $R_1$ can be a $(C_5-C_{10})$alkyl, $(C_2-C_{10})$alkenyl, or $(C_2-C_{10})$alkynyl that can be substituted on the carbon adjacent to the triple bond in Formula (I) with hydroxy; or $R_1$ can be a $(C_5-C_{10})$alkyl that can be substituted with hydroxy, mercapto, carboxy or $NR_aR_b$; or $R_1$ can be a $(C_5-C_{10})$alkyl that can be substituted with hydroxy; or $R_1$ can be a $(C_5-C_{10})$alkyl that can be substituted on the carbon adjacent to the triple bond in Formula (I) with hydroxy.

In other embodiments of Formula (I), $R_1$ can be $(C_1-C_{20})$alkyl, $(C_2-C_{20})$alkenyl, or $(C_2-C_{20})$alkynyl, which $(C_1-C_{20})$alkyl, $(C_2-C_{20})$alkenyl, or $(C_2-C_{20})$alkynyl can be substituted with $(C_1-C_{20})$alkanoyloxy; $R_1$ can be a $(C_5-C_{10})$alkyl that can be substituted on the carbon adjacent to the triple bond in Formula (I) with $(C_1-C_{20})$alkanoyloxy; $R_1$ can be 1-hydroxyhexane, 1-hydroxy-2,2-dimethylpropane, 1-acetoxyhexane or cis-1-hydroxy-3-hexane; or $R_1$ can be a $(C_5\text{-}C_{10})$alkyl that can be substituted on the carbon adjacent to the triple bond in Formula (I) with acetoxy.

In certain embodiments of Formula (I), $R_2$ can be $CF_2Br$, $CFHBr$, $CF_2Cl$, or $CFHCl$.

In certain aspects of the invention, the DNMT1 inhibitor of Formula (I) can be a compound of Formula (II):

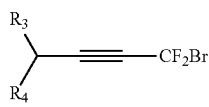

or a salt thereof, where $R_3$ can be hydroxy, mercapto, chloro, bromo, methylthio, ethylthio, methoxy, ethoxy, acetylamino, $(C_1\text{-}C_{10})$alkanoyloxy, arylcarbonyloxy, aryloxy; and $R_4$ can be $(C_4\text{-}C_{10})$alkyl, $(C_2\text{-}C_{10})$alkenyl, or $(C_2\text{-}C_{10})$alkynyl, which $(C_4\text{-}C_{10})$alkyl, $(C_2\text{-}C_{10})$alkenyl, or $(C_2\text{-}C_{10})$alkynyl can be optionally substituted with one or more groups independently selected from halo, hydroxy, mercapto, $(C_1\text{-}C_{10})$alkoxy, $(C_1\text{-}C_{10})$alkylthio, carboxy, $(C_1\text{-}C_{10})$alkoxycarbonyl, aryl, heteroaryl, and $NR_aR_b$.

In other embodiments of Formula (II), $R_3$ can be hydroxy, mercapto, chloro, bromo, methylthio, ethylthio, methoxy, ethoxy, or acetylamino; and $R_4$ can be $(C_4\text{-}C_{10})$alkyl, $(C_2\text{-}C_{10})$alkenyl, or $(C_2\text{-}C_{10})$alkynyl, which $(C_4\text{-}C_{10})$alkyl, $(C_2\text{-}C_{10})$alkenyl, or $(C_2\text{-}C_{10})$alkynyl can be optionally substituted with one or more groups independently selected from halo, hydroxy, mercapto, $(C_1\text{-}C_{10})$alkoxy, $(C_1\text{-}C_{10})$alkylthio, carboxy, $(C_1\text{-}C_{10})$alkoxycarbonyl, aryl, heteroaryl, and $NR_aR_b$.

In yet other embodiments of Formula (II), $R_4$ can be $(C_4\text{-}C_{10})$alkyl that can be optionally substituted with one or more groups independently selected from halo, hydroxy, mercapto, $(C_1\text{-}C_{10})$alkoxy, $(C_1\text{-}C_{10})$alkylthio, carboxy, $(C_1\text{-}C_{10})$alkoxycarbonyl, aryl, heteroaryl, and $NR_aR_b$.

In some embodiments of Formula (II), $R_4$ can be $(C_4\text{-}C_{10})$alkyl that can optionally be substituted with one or more groups independently selected from halo, hydroxy, mercapto, carboxy, $(C_1\text{-}C_{10})$alkoxycarbonyl, and $NR_aR_b$; or $R_4$ can be $(C_4\text{-}C_{10})$alkyl; or $R_4$ can be $(C_4\text{-}C_6)$alkyl.

In some embodiments, the DNMT1 inhibitor can be XB05a, XB05b, XB05, 1-bromo-1,1-difluoro-4-hydroxy-5,5-dimethyl-2-hexyne, or a salt thereof.

In still other embodiments, the DNMT1 inhibitor can be

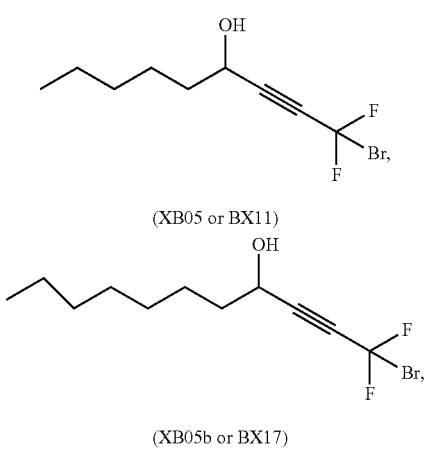

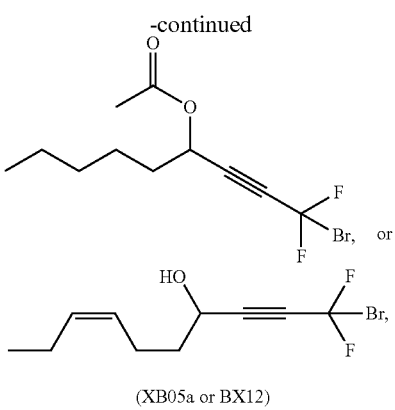

or a salt thereof.

In some embodiments, the DNMT1 inhibitor is 5-azacytidine (Vidaza™) or decitabine (Dacogen™). In some embodiments, the DNMT1 inhibitor is XB05 (BX11), XB05a (BX12), or XB05b (BX17). Additional non-limiting examples of DNMT1 inhibitors are known in the art. Additional, non-limiting examples of DNMT1 inhibitors are described in Yang et al., *Trends Pharmacol. Sci.* (2010) Vol. 31, pp. 536-546 (e.g., 5-azacytidine, 5-aza-2'-deoxycytidine, 5,6-dihydro-5-azacytidine, zebularine, 5-fluoro-2'-deoxycytidine, NPEOC-DAC, S110, hydralazine, RG108, procainamide, and SGI-1027). One or more DNMT1 inhibitors can be administered to the animal in a DNMT1 inhibitor treatment in any combination.

In certain embodiments, the DNMT1 inhibitor (such as XB05 and other DNMT1 inhibitors of Formula I) is more selective in DNA methylation as compared to the DNMT1 inhibitor 5-aza which appears to cause global DNA methylation. In certain embodiments, the DNMT1 inhibitor induces selective demthylation of silenced tumor-suppressor genes.

In some instances, the DNMT1 inhibitor causes an increase in DNA damage and an increase in intracellular reactive oxygen species (ROS). In some embodiments, the DNMT1 inhibitor inhibits stress (e.g., cells oxidative, electrophilic, or proteotoxic stress) defense mechanisms and can cause selective toxicity in cancer cells; in certain instances "anti-stress" responses are also inhibited (e.g., simultaneously). In still other instances, the DNMT1 inhibitor induces stress (e.g., oxidative) and also inhibits glutathione synthesis.

In some embodiments, the DNMT1 inhibitor has antiproliferative activity in the sub-micromolar range for one or more malignant cell lines.

In other instances, the DNMT1 inhibitor can react (e.g., selectively) with thiols. In other embodiments, DNMT1 inhibitors can form covalent adducts with cellular thiols; cellular thiols include all molecules of a cell (e.g., amino acids, metabolites, lipids, proteins) that have a sulfur that could become a thiol (e.g., R-SH). Similarly, cellular selenols include all molecules of a cell (e.g., amino acids, metabolites, lipids, proteins) that have a selenium that could become a selenol (e.g., R-SeH). In certain embodiments, DNMT1 inhibitors can covalently modify cell molecules, such as amino acid residues (e.g., cysteine or selenocysteine) within cellular proteins and/or antioxidants. For example, the DNMT1 inhibitor may interfere with and/or interact with one or more proteins (e.g., those involved in cellular homeostatsis and stress response, or e.g., but not limited to thioredoxin, thioredoxin reductase, hsp90, hsp70, 26S proteasome, adenine nucleotide transporter, ATP synthase, NF-κB, or Keap1) via, for example, covalent modification of cysteine or selenocysteine residues. In certain embodiments, DNMT1 inhibitors form covalent adducts with cellular thiols or cellular selenols on cysteine, GSH, selenocysteine, selenocysteine residues (e.g., reactive selenocysteine residues or highly reactive selenocysteine residues) and/or cysteine residues (e.g., reactive cysteine residues or highly reactive cysteine residues). In some instances, the DNMT1 inhibitor can result in the depletion of glutathione. In yet other instances, the DNMT1 inhibitor can interact directly with GSH, which then may modulate (e.g., reduce) cellular response to stress. In other instances, the DNMT1 inhibitor has a low reactivity with thiol-based molecules (e.g., cellular thiols or antioxidants).

In other embodiments, the effect of DNMT1 inhibitors on cells (e.g., anti-proliferation and DNA damage) can be a result of the reactivity of the DNMT1 inhibitor with cellular thiols.

Treatment after DNMT1 Inhibitor Administration

Some embodiments of the invention include methods comprising attenuating the activity of a DNA (cytosine-5)-methyltransferase 1 (DNMT1) inhibitor including, but not limited to the step of administering a composition comprising an antioxidant to an animal who had previously been administered a DNMT1 inhibitor.

In certain embodiments, the animal is undergoing a treatment for a disease. For example, the animal can be undergoing a treatment for cancer, including but not limited to chemotherapy. In certain instances, the animal can be suffering from a negative (e.g., toxic) effect from the DNMT1 inhibitor, and treatment with a composition comprising an antioxidant can result in a decrease in that negative effect (e.g., by rescuing the animal from toxics effects of the DNMT1 inhibitor).

In some embodiments, an increase in oxidative stress caused DNA damage and cell death as a result of a DNMT1 inhibitor (e.g., the compounds of Formula (I) such as XB05) administration is blocked by an antioxidant, a scavenger of ROS, or a combination thereof.

In some instances, the DNMT1 inhibitor reacts with cellular thiols and, in particular, with thiol groups present on cysteine residues. Although not being limited by any particular theory or mechanism of action, anti-proliferative and/or cell-death inducing properties of these DNMT1 inhibitors can be caused at least in part by their reactivity with such cellular thiols, including thiol groups on one or more cysteine residues. Certain instances of the invention can result from antioxidant compounds, including, in particular, thiol-based antioxidants, that can inhibit the DNMT1 inhibitors' reactivity with cellular thiols and thereby attenuating (e.g., by reducing or inhibiting) their anti-proliferative and/or cell-death inducing activities. Hence, certain embodiments of the invention include methods for attenuating (e.g., reducing or inhibiting) or otherwise modulating the activity of a DNMT1 inhibitor by administering an antioxidant (e.g., N-acetyl cysteine (NAC), glutathione (GSH), or another thiol-based antioxidant). Such methods can be useful, since they may inhibit or reduce toxic side effects of a DNMT1 inhibitor during its use in a chemotherapeutic or other therapeutic regimen. In addition, such methods are useful for inhibiting or reducing toxic effects of DNMT1 inhibitors, such as in the event of an overdose.

In certain embodiments, the antioxidant concentration is about 0.01 μM, about 0.05 μM, about 0.1 μM, about 0.25 μM, about 0.5 μM, about 0.75 μM, about 1 μM, about 5 μM, about 10 μM, about 50 μM, about 100 μM, about 200 μM, about 500 μM, about 1 mM, about 2 mM, about 2.5 mM, about 3 mM, about 4 mM, about 5 mM, about 6 mM, about 7 mM, about 8 mM, about 9 mM, about 10 mM, about 20 mM, about 40 mM, about 50 mM, about 100 mM, about 200 mM, or about 500 mM. In other embodiments, the antioxidant concentration is about 0.05 to about 15 mg/kg body weight, about 0.2 to about 10 mg/kg body weight, about 0.5 to about 7 mg/kg body weight, about 0.01 mg/kg, about 0.02 mg/kg, about 0.05 mg/kg, about 0.1 mg/kg, about 0.2 mg/kg, about 0.5 mg/kg, about 1 mg/kg, about 3 mg/kg, about 5 mg/kg, about 5.5 mg/kg, about 6 mg/kg, about 6.5 mg/kg, about 7 mg/kg, about 7.5 mg/kg, about 8 mg/kg, about 10 mg/kg, about 12 mg/kg, about 15 mg/kg about 20 mg/kg, about 30 mg/kg, about 40 mg/kg, about 50 mg/kg, about 80 mg/kg, about 100 mg/kg, or about 150 mg/kg body weight.

Antioxidant administration can include the administration of one or more antioxidants to an animal (e.g., mammal such as a human). In some embodiments, the animal is a human (e.g. a human having a cancer, such as any of the cancers described herein).

In some embodiments, the one or more antioxidants can be administered by oral, intravenous, intaarterial, intramuscular, intraperitoneal, or subcutaneous administration. In some embodiments, the one or more antioxidants is administered locally (e.g., into a cancerous cell mass or in a tissue proximal to a cancerous cell mass). In some embodiments where two or more antioxidants are administered to the animal, they are administered as separate compositions (e.g., via the same or a different route of administration (e.g., any of the routes of administration described herein or known in the art)). In some embodiments where two or more antioxidants are administered to the animal, the two or more antioxidants are administered in the same composition.

In some embodiments, the antioxidants are formulated for oral, intravenous, intramuscular, intraperitoneal, or subcutaneous administration using methods known in the art (see, e.g., the methods described in U.S. Patent Application Publication No. 2008/0188570, herein incorporated by reference).

In some embodiments, the animal is administered a dose of one or more antioxidants at least once every two months (e.g., at least once every month, at least once every two weeks, at least once a week, at least twice a week, at least three times a week, at least once a day, at least twice a day, or at least three times a day). In some embodiments, the one or more antioxidants are administered by a medical professional (e.g., local administration, such as injection, to a mass of cancer cells in the animal) or are self-administered by the animal having a cancer.

The periodic administration of one or more antioxidants can take place over a period of time (e.g., at least one week, at least two weeks, at least one month, at least two months, at least six months, and at least one year).

DNMT1 Inhibitor Treatment Administered Prior to Antioxidant

DNMT1 inhibitor treatment administered prior to the antioxidant administration can include the administration of one or more DNMT1 inhibitors to an animal (e.g., mammal such as a human). In some embodiments, the animal is a human (e.g. a human having a cancer, such as any of the cancers described herein).

In some embodiments, the one or more DNMT1 inhibitors can be administered by oral, intravenous, intaarterial, intramuscular, intraperitoneal, or subcutaneous administration. In some embodiments, the one or more DNMT1 inhibitors is administered locally (e.g., into a cancerous cell mass or in a tissue proximal to a cancerous cell mass). In some embodiments where two or more DNMT1 inhibitors are administered to the animal, they are administered as separate compositions (e.g., via the same or a different route of administration (e.g., any of the routes of administration described herein or known in the art). In some embodiments where two or more DNMT1 inhibitors are administered to the animal, the two or more DNMT1 inhibitors are administered in the same composition.

In some embodiments, the DNMT1 inhibitors are formulated for oral, intravenous, intramuscular, intraperitoneal, or subcutaneous administration using methods known in the art (see, e.g., the methods described in U.S. Patent Application Publication No. 2008/0188570, herein incorporated by reference). In some embodiments, when the DNMT1 inhibitor is administered prior to the antioxidant, the amount of a DNMT1 inhibitor administered to the animal (or the amount of each DNMT1 inhibitor when more than one DNMT1 inhibitor is administered to the animal) in a single dose is, e.g., between 1 mg to 800 mg, 1 mg to 700 mg, 1 mg to 600 mg, 1 mg to 500 mg, 10 mg to 400 mg, 10 mg to 300 mg, 10 mg to 200 mg, 10 mg to 100 mg, 10 mg to 50 mg, 1 mg to 50 mg, 1 mg to 100 mg, 100 mg to 200 mg, 200 mg to 300 mg, 300 mg to 400 mg, 400 mg to 500 mg, 500 mg to 600 mg, and 600 mg to 800 mg. In yet other embodiments, when the DNMT1 inhibitor is administered prior to the antioxidant, the DNMT1 inhibitor concentration is about 0.01 µM, about 0.05 µM, about 0.1 µM, about 0.25 µM, about 0.5 µM, about 0.75 µM, about 1 µM, about 5 µM, about 10 µM, about 50 µM, about 100 µM, about 200 µM, about 500 µM, about 1 mM, about 2 mM, about 2.5 mM, about 3 mM, about 4 mM, about 5 mM, about 6 mM, about 7 mM, about 8 mM, about 9 mM, about 10 mM, about 20 mM, about 40 mM, about 50 mM, about 100, mM, about 200 mM, or about 500 mM. In yet other embodiments, when the DNMT1 inhibitor is administered prior to the antioxidant, the DNMT1 inhibitor concentration is about 0.05 to about 15 mg/kg body weight, about 0.2 to about 10 mg/kg body weight, about 0.01 mg/kg, about 0.02 mg/kg, about 0.05 mg/kg, about 0.1 mg/kg, about 0.2 mg/kg, about 0.5 to about 7 mg/kg body weight, about 0.5 mg/kg, about 1 mg/kg, about 3 mg/kg, about 5 mg/kg, about 5.5 mg/kg, about 6 mg/kg, about 6.5 mg/kg, about 7 mg/kg, about 7.5 mg/kg, about 8 mg/kg, about 10 mg/kg, about 12 mg/kg, about 15 mg/kg, about 20 mg/kg, about 30 mg/kg, about 40 mg/kg, about 50 mg/kg, about 80 mg/kg, about 100 mg/kg, or about 150 mg/kg body weight.

In certain embodiments, when the DNMT1 inhibitor is administered prior to the antioxidant, the DNMT1 inhibitor concentration is or could be toxic or lethal to the animal.

In some embodiments, the animal is administered a dose of one or more DNMT1 inhibitors at least once every two months (e.g., at least once every month, at least once every two weeks, at least once a week, at least twice a week, at least three times a week, at least once a day, at least twice a day, or at least three times a day). In some embodiments, the one or more DNMT1 inhibitors are administered by a medical professional (e.g., local administration, e.g., injection, to a mass of cancer cells in the animal) or are self-administered by the animal having a cancer.

The periodic administration of one or more DNMT1 inhibitors can take place over a period of time (e.g., at least one week, at least two weeks, at least one month, at least two months, at least six months, and at least one year).

In some embodiments, the animal is non-responsive to a prior cancer treatment. In some embodiments, the animal is further administered one or more additional therapeutic agents (e.g., an analgesic and/or a chemotherapeutic). In some embodiments, the animal is previously administered a cancer treatment, and such prior cancer treatment is terminated prior to administering the DNMT1 inhibitor to the animal.

In some embodiments, the DNMT1 inhibitor treatment is any DNMT1 inhibitor treatment described herein (e.g., any of the individual DNMT1 inhibitors described herein, any of the routes of administration, any of the formulations of a DNMT1 inhibitor, any of the frequencies or doses of administration, and/or any of the total time periods of treatment described herein). In some embodiments, the DNMT1 inhibitor is any DNMT1 inhibitor known in the art.

Cancers

Some embodiments of the invention include methods for attenuating DNMT1 inhibitor activity when an animal has cancer or is being treated for cancer. The cancer can be of any type. For example, the animal can have chondrosarcoma cancer, lung cancer, malignant peripheral nerve sheath tumor, prostate cancer, malignant melanoma, a sarcoma, breast cancer, colon cancer, gastric cancer, or pancreatic cancer. In some embodiments, the animal has already been diagnosed as having a cancer. In some embodiments, the animal can present with one or more (e.g., two or more, or three or more) symptoms of a cancer (e.g., persistent fatigue, unintentional weight loss, pain, bowel changes, chronic cough, lump or thickening that can be felt under the skin, yellowing, darkening, or redness of the skin, difficulty swallowing, hoarseness, and persistent indigestion). In some non-limiting embodiments, the animal has prostate cancer, lung adenocarcinoma, colon cancer, gastric carcinoma, basal cell carcinoma, malignant peripheral nerve sheath tumors, breast cancer, malignant melanoma, or a sarcoma.

The animal can be diagnosed or identified as having a cancer by the observation or detection of one or more symptoms of cancer in a animal (e.g., one or more of the symptoms described herein or other symptoms of cancer known in the art). In some embodiments, the animal is diagnosed or identified as having a cancer through the use of imaging (e.g., X-ray, ultrasound, computed tomograph, and magnetic resonance imaging).

In some embodiments, the cancer is basal cell carcinoma, thyroid cancer, squamous cell carcinoma, neuroblastoma, ovarian cancer, melanoma, renal cell carcinoma, hepatocellular carcinoma, breast cancer, colon cancer, lung cancer, pancreatic cancer, prostate cancers, chronic lymphocytic leukemia (CLL), acute lymphoblastic leukemia, rhabdomyosarcoma, Glioblastoma multiforme, meningioma, bladder cancer, gastric cancer, Glioma, oral cancer, nasopharyngeal carcinoma, kidney cancer, rectal cancer, stomach cancer, uterine cancer, or a leukemia. In some embodiments, the cancer is chondrosarcoma cancer, lung cancer, malignant peripheral nerve sheath tumor, prostate cancer, malignant melanoma, a sarcoma, breast cancer, colon cancer, gastric cancer, pancreatic cancer, brain cancer, basal cell carcinoma, liver cancer, leukemia, or myelodysplastic syndrome.

In certain instances, the cancer treatment can include treatment of angiogenesis and/or metastasis in a tumor, including, but not limited to, basal cell carcinoma, thyroid cancer, squamous cell carcinoma, neuroblastoma, ovarian, melanoma, renal cell carcinoma, hepatocellular carcinoma, breast, colon, lung, pancreatic, and prostate cancers. In some embodiments, the cancer treatment results in the reduction of tumor size, the reduction in the number of tumors, or both.

Compositions Comprising a DNMT1 Inhibitor and an Antioxidant, and Treatments Using Those Compositions Certain embodiments of the invention include methods comprising administering a composition comprising a DNMT1 inhibitor and an antioxidant, and do not require that a DNMT1 inhibitor be administered to the animal prior to administering the composition. Other embodiments include compositions comprising a DNMT1 inhibitor and an antioxidant. The DNMT1 inhibitor can be any DNMT1 inhibitor described herein. The antioxidant can be any antioxidant described herein.

Other embodiments include methods for treating at least one cell (e.g., a cell from livestock, pig, cow, horse, dog, cat, primate, human, a human patient, or a mammal), where the method comprises administering to at least one cell a composition comprising a DNMT1 inhibitor (e.g., Formula (I)) and an antioxidant. Sometimes, the cell is part of a multicellulular organism or is part of an organ or an organ system. In other instances, the cell is selected from the group consisting of Lewis lung carcinoma cells, B16F10 melanoma cells, TC-1 cervical carcinoma cells, Hs27 cells, MCF7 cells, MDA-MB-231 cells, A549 cells, U937 cells, DU145, IMR-90, MCF-10a, THP-1 cells, 300.19 cells, CHO cells, mouse cells, and African green monkey cells. The cell can also be a transfected cell. The cell can be an animal cell (e.g., a mammalian cell or human cell).

In some instances, an administration of a DNMT1 inhibitor occurred prior to the treatment with the composition. In other instances, an administration of a DNMT1 inhibitor did not occur prior to the treatment with the composition. Some embodiments include methods for treating a patient who is receiving a DNMT1 therapy (e.g., as part of a chemotherapeutic treatment) and the antioxidant is administered in order to decrease or inhibit anti-proliferative and/or cell-death inducing activity of the DNMT1 inhibitor.

In certain embodiments, the antioxidant concentration in the composition (for the method or for the composition) is about 0.01 µM, about 0.05 µM, about 0.1 µM, about 0.25 µM, about 0.5 µM, about 0.75 µM, about 1 µM, about 5 µM, about 10 µM, about 50 µM, about 100 µM, about 200 µM, about 500 µM, about 1 mM, about 2 mM, about 2.5 mM, about 3 mM, about 4 mM, about 5 mM, about 6 mM, about 7 mM, about 8 mM, about 9 mM, about 10 mM, about 20 mM, about 40 mM, about 50 mM, about 100, mM, about 200 mM, or about 500 mM. In other embodiments, the antioxidant concentration (for the method or for the composition) is about 0.05 to about 15 mg/kg body weight, about 0.2 to about 10 mg/kg body weight, about 0.5 to about 7 mg/kg body weight, about 0.01 mg/kg, about 0.02 mg/kg, about 0.05 mg/kg, about 0.1 mg/kg, about 0.2 mg/kg, about 0.5 mg/kg, about 1 mg/kg, about 3 mg/kg, about 5 mg/kg, about 5.5 mg/kg, about 6 mg/kg, about 6.5 mg/kg, about 7 mg/kg, about 7.5 mg/kg, about 8 mg/kg, about 10 mg/kg, about 12 mg/kg, about 15 mg/kg about 20 mg/kg, about 30 mg/kg, about 40 mg/kg, about 50 mg/kg, about 80 mg/kg, about 100 mg/kg, or about 150 mg/kg body weight.

In yet other embodiments, the DNMT1 inhibitor concentration (for the method or for the composition) is about 0.01 µM, about 0.05 µM, about 0.1 µM, about 0.25 µM, about 0.5 µM, about 0.75 µM, about 1 µM, about 5 µM, about 10 µM, about 50 µM, about 100 µM, about 200 µM, about 500 µM, about 1 mM, about 2 mM, about 2.5 mM, about 3 mM, about 4 mM, about 5 mM, about 6 mM, about 7 mM, about 8 mM, about 9 mM, about 10 mM, about 20 mM, about 40 mM, about 50 mM, about 100, mM, about 200 mM, or about 500 mM. In yet other embodiments, the DNMT1 inhibitor concentration (for the method or for the composition) is about 0.05 to about 15 mg/kg body weight, about 0.2 to about 10 mg/kg body weight, about 0.01 mg/kg, about 0.02 mg/kg, about 0.05 mg/kg, about 0.1 mg/kg, about 0.2 mg/kg, about 0.5 to about 7 mg/kg body weight, about 0.5 mg/kg, about 1 mg/kg, about 3 mg/kg, about 5 mg/kg, about 5.5 mg/kg, about 6 mg/kg, about 6.5 mg/kg, about 7 mg/kg, about 7.5 mg/kg, about 8 mg/kg, about 10 mg/kg, about 12 mg/kg, about 15 mg/kg about 20 mg/kg, about 30 mg/kg, about 40 mg/kg, about 50 mg/kg, about 80 mg/kg, about 100 mg/kg, or about 150 mg/kg body weight.

Embodiments of the invention include administering the composition to an animal (e.g., a mammal or human) that has cancer (e.g., any of the cancers described herein, or diagnosed or identified as described herein). In certain embodiments, the administration is effective to treat cancer; for example, the amount of the DNMT1 inhibitor, antioxidant, or both are in amount(s) effective to treat cancer.

In some embodiments, the composition can be administered by oral, intravenous, intaarterial, intramuscular, intraperitoneal, or subcutaneous administration. In some embodiments, the composition is administered locally (e.g., into a cancerous cell mass or in a tissue proximal to a cancerous cell mass). In some embodiments where two or more compositions are administered to the animal, they are administered as separate compositions (e.g., via the same or a different route of administration (e.g., any of the routes of administration described herein or known in the art)). In some embodiments where two or more compositions are administered to the animal, the two or more compositions are administered from the same composition.

In some embodiments, the compositions are formulated for oral, intravenous, intramuscular, intraperitoneal, or subcutaneous administration using methods known in the art (see, e.g., the methods described in U.S. Patent Application Publication No. 2008/0188570, herein incorporated by reference in its entirety).

In some embodiments, the animal is administered a dose of one or more compositions at least once every two months (e.g., at least once every month, at least once every two weeks, at least once a week, at least twice a week, at least three times a week, at least once a day, at least twice a day, or at least three times a day). In some embodiments, the one or more compositions are administered by a medical professional (e.g., local administration, such as injection to a mass of cancer cells in the animal) or are self-administered by the animal having a cancer.

The periodic administration of one or more compositions can take place over a period of time (e.g., at least one week, at least two weeks, at least one month, at least two months, at least six months, and at least one year).

In some embodiments, the animal is non-responsive to a prior cancer treatment. In some embodiments, the animal is further administered one or more additional therapeutic agents (e.g., an analgesic and/or a chemotherapeutic). In some embodiments, the animal is previously administered a cancer treatment, and such prior cancer treatment is terminated prior to administering the composition to the animal.

EXAMPLE SET A

Materials and Methods

Materials. XB05 was prepared according to previously described methods, such as those described in U.S. Pat. No. 8,207,381 (which is herein incorporated by reference in its entirety). S-(+)-camptothecin, Z-VAD-fmk, L-buthionine-sulfoximine, antimycin A, diethyl maleate, maleimide, reduced L-glutathione, N-acetyl cysteine, L-cysteine, and L-ascorbic acid were purchased from Sigma-Aldrich (St. Louis, Mo.). Antibodies against cleaved caspase-3 (#9661), γ-H2AX (#9718), phosphorylated (Ser 51) eIF2α (#9721), eIF2α (#9722), and BiP (#3177) were purchased from Cell Signaling Technology, Inc. (Danvers, Mass.). Thapsigargin, anti-rabbit and anti-mouse antibodies linked to horseradish peroxidase, and antibodies against PARP-1 (sc-8007), Nrf2 (sc-365949), Ku-70 (sc-5309) and GAPDH (sc-47724) were purchased from Santa Cruz Biotech (Santa Cruz, Calif.).

Cell Culture and Treatments. Cell lines were either recently purchased from the American Type Culture Collection (ATCC) or verified by short tandem repeat (STR) analysis (IDEXX Laboratories, Westbrook, Me.). Cells were grown in the appropriate medium supplemented with 10% fetal bovine serum (FBS, Hyclone Laboratories, Logan, Utah), 62.5 µg/mL penicillin and 100 µg/mL streptomycin (Life Technologies, Grand Island, N.Y.) in a humidified incubator at 37° C. with 5% $CO_2$. The media were as follows: Dulbecco's Modified Eagle's Medium (DMEM) for A549, MDA-MB-231, DU145, and Hs27 cells; RPMI 1640 for U937 cells; Eagle's Minimal Essential Medium (EMEM) supplemented with Eagle's Balanced Salt Solution (EBSS), 2 mM L-glutamine, 1 mM sodium pyruvate, 1500 mg/L sodium bicarbonate and non-essential amino acids (Lonza, Walkersville, Md.) for IMR-90 cells; Mammary Epithelial Growth Medium (MEGM®) supplemented with all of the components of the MEGM SingleQuots® kit, except for GA-1000 (Lonza) for MCF-10A cells. Cells were treated by direct addition of XB05 solutions into the culture medium to give the final concentrations indicated in the figures. Unless otherwise stated, cells were at approximately 40% confluence at the start of treatment. XB05 solutions were freshly prepared from stock solutions of 2 mM in 100% DMSO by dilution with cell culture medium. Final DMSO concentrations were 0.05% in both vehicle control and XB05-treated cells. As a positive control for apoptosis, cells were treated with camptothecin (6 µg/mL) for the times indicated in the figure legends. As a positive control for DNA damage, cells were irradiated with 800 µJ in a UV Stratalinker 2400 (Stratagene, St. Clara, Calif.), and then allowed to grow in culture for an additional 2 h.

Cell Proliferation Assays. The antiproliferative activity of XB05 was tested using a previously published 3-(4,5-dimethylthiazol-2-yl)-2,5-diphenyltetrazolium bromide (MTT) assay protocol (Girvan et al., "AGRO100 inhibits activation of nuclear factor-kappaB (NF-kappaB) by forming a complex with NF-kappaB essential modulator (NEMO) and nucleolin" Molecular Cancer Therapeutics (2006) Vol. 5, No. 7, pp. 1790-1799). Briefly, cells were seeded in quadruplicate wells in 96-well plates and allowed to adhere overnight. To account for intrinsic differences in growth rates, cells were plated at the following densities so as to achieve comparable MTT absorbance values (between 1 and 2) in untreated samples after 72 h: A549, DU145, and MDA-MB-231, 1000 cells/well; Hs27 and U937, 1500 cells/well; IMR-90 and MCF-10A, 5000 cells/well. Plates were incubated with XB05 for 72 h, during which the cell culture medium was not changed. Cell viability was determined and the background corresponding to medium alone (no cells) was subtracted. Data were analyzed as described in the Brief Description of the Drawings.

Trypan Blue Exclusion Assay and Microscopy: Cells were treated as indicated in the figures. After 72 h, cells were trypsinized (in the case of adherent cells), stained with trypan blue solution (0.4%) (BioRad, Hercules Calif.) and cell number and percent viability determined on a TC10 automated cell counter (BioRad) using triplicate measurements for each sample. Phase contrast microscopy images were obtained on an EVOSfl digital inverted microscope (Advanced Microscopy Group, Bothell, Wash.).

Flow Cytometric Assays. Analyses were performed using a FACScalibur flow cytometer (BD Biosciences, Mountain View, Calif.) and FlowJo software (Tree Star, Inc., Ashland, Oreg.). Cells were treated as indicated in the figures and in the Brief Description of the Drawings. Cells were harvested by using TrypLE Cell Dissociation Reagent (Life Technologies). For cell death analyses, cells (adherent and detached cells) were stained with annexin-V-FITC and propidium iodide (PI) using the Apoptosis Detection Kit (BD Biosciences, San Jose, Calif.), according to the manufacturer's instructions. For cell-cycle distribution, cells were fixed, and stained with PI using the Cycle Test Plus kit (Becton Dickinson, Franklin Lakes, N.J.). For detection of γ-H2AX, cells were washed with PBS and fixed in 4% paraformaldehyde in PBS for 10 min at 37° C. Cells were then permeabilized in 90% methanol for 30 min on ice, blocked in 2% BSA (w/v in PBS) for 1 h, and incubated with γ-H2AX antibody or rabbit IgG isotype control (Santa Cruz, sc-2027) (0.3 µg/mL in 1% BSA) for 1 h. After washing, cells were incubated with goat anti-rabbit IgG antibody conjugated to Alexa Fluor-488® (Life Technologies) for 1 h at room temperature. For reactive oxygen species (ROS) detection, cells ($1 \times 10^6$ cells/mL) were stained with 25 µM 6-carboxy-2',7'-dichlorodihydrofluorescein diacetate (Carboxy-$H_2$DCFDA, Life Technologies) in PBS for 30 min at 37° C. After washing with PBS, cells were re-suspended in PBS containing 1 µg/mL PI to allow exclusion of non-viable cells. For detection of mitochondrial superoxide, cells were harvested, washed with PBS and stained with 5 µM MitoSOX™ Red (Life Technologies) in warm PBS for 10 min at 37° C. Cells were then washed twice with PBS, re-suspended at a density of $1 \times 10^6$ cells/mL in PBS and analyzed by flow cytometry.

Clonogenic Assays. Cells were plated at low density (300 cells/well) in 6-well tissue culture plates, and allowed to adhere overnight. Where indicated, the medium was then replaced with fresh medium containing antioxidants or vehicle (sterile ultrapure $H_2O$). XB05 or vehicle control (DMSO) was then added directly to the medium at the concentrations indicated. After 10 days, cells were fixed with 4% paraformaldehyde in PBS and stained with Accustain Crystal Violet Solution (Sigma Aldrich) washed and air-dried. Colonies were counted using the cell counter feature in the Image J software, available from the National Institute of Health (<<rsbweb.nih.gov/ij/download.html>>).

Cell Extracts. After treatment as indicated in figure legends, cells were washed twice with ice-cold PBS. Nuclear cells extracts were isolated using the NE-PER Nuclear and Cytoplasmic Extraction Kit (Thermo Scientific, Rockford, Ill.), per the manufacturer's protocol. For total cell extract, cells were lysed in RIPA buffer (Thermo Scientific) containing protease inhibitor cocktail III and phosphatase inhibitor cocktail (Calbiochem, Billerica, Mass.) for 5 min at 4° C., and then cleared by centrifugation at 16,000 g for 10 min at 4° C. All protein concentrations were determined using the DC Protein Assay™ kit (BioRad, Hercules, Calif.).

Western Blotting. Equal amounts of protein per sample (typically, 50 µg) were resolved by SDS-Tris polyacrylamide gel electrophoresis and then electrotransferred onto polyvinylidine fluoride membranes (Millipore, Bedford, Mass.) in Tris-glycine buffer containing 20% methanol. Membranes were blocked with 5% milk or 5% BSA (for phospho-protein detection) in TBS/0.01% Tween. Proteins were detected using the following primary antibody concentrations: PARP-1 (1:1000), cleaved caspase-3 (1:1000), γ-H2AX (Ser139) (1:000), phospho-eIF2α (Ser51) (1:1000), eIF2α (1:1000), Bip (1:1000), Nrf2 (1:1000), Ku-70

(1:1000) and GAPDH (1:1000). In some cases, membranes were stripped using Restore Plus western blot stripping buffer (Thermo Scientific) and then reprobed as described in the Brief Description of the Drawings. Where indicated, band intensities were quantified using the UN-SCAN-IT Gel digitizing software (Silk Scientific, Orem Utah) and normalized to vehicle control.

Comet Assays. Cells were washed once with ice cold PBS, harvested as described and re-suspended at $1 \times 10^5$ cells/mL in PBS. As a positive control, cells were incubated with 100 µM tert-butyl hydrogen peroxide (TBHP) for 30 mins (U937, A549) or 1 h (Hs27) at 4° C. prior to harvesting. Comet assays were performed using the CometAssay Kit (Trevigen, Gaithersburg, Md.) according to the manufacturer's instructions. Cells were visualized and digital images captured on an EVOSfl Digital Fluorescent Microscope equipped with a fluorescein light cube.

Reduced Glutathione Content Analyses. After treatment as indicated in the figures and in the Brief Description of the Drawings, cells were harvested as described, counted and dispensed at a density of 10,000 cells/well in triplicate on a 96-well white, opaque bioluminescence plate (Corning). Cellular content of reduced glutathione (GSH) was analyzed using the GSH-Glo® Glutathione Assay Kit (Promega) according to the manufacturer's instructions. The chemiluminescent signal was quantified on a Biotek Synergy HT plate-reader (Biotek, Winooski, Vt.) using an integration time of 1 s/well.

Dithiobis-2-nitrobenzoic Acid (DTNB) Assay for Free Sulfhydryls. For each experiment, a 20× working solution of DTNB (2 mM DTNB, 50 mM sodium acetate in 100 mM Tris-HCl, pH 8.0) and 2× solutions of cysteine and GSH (0.5 mM in 100 mM Tris-HCl, pH 8.0) were freshly prepared. 10 mM stock solutions of XB05, diethyl maleate and maleimide were prepared in 100% DMSO, and subsequently serially diluted to 2× working solutions in 100 mM Tris-HCl, pH 8.0. 100 µl each of thiol compounds (final concentration 0.25 mM) and thiol-reactive compounds (final concentrations 0.05-5 mM) or vehicle control (DMSO) were added in duplicate to a 96-well plate and allowed to incubate at 37° C. for 30 minutes. 20 µl of 20×DTNB working solution was then added to each well (final concentration 100 µM), and allowed to incubate at room temperature for an additional 5 minutes. Absorbance was read on a Biotek HT Synergy Plate reader (Winooski, Vt.) at 412 nm.

Statistical Analyses. Where indicated, statistical comparisons were conducted using Student's t-test. Statistical significance was set at $p \leq 0.05$.

Results and Discussion

Figure 2:
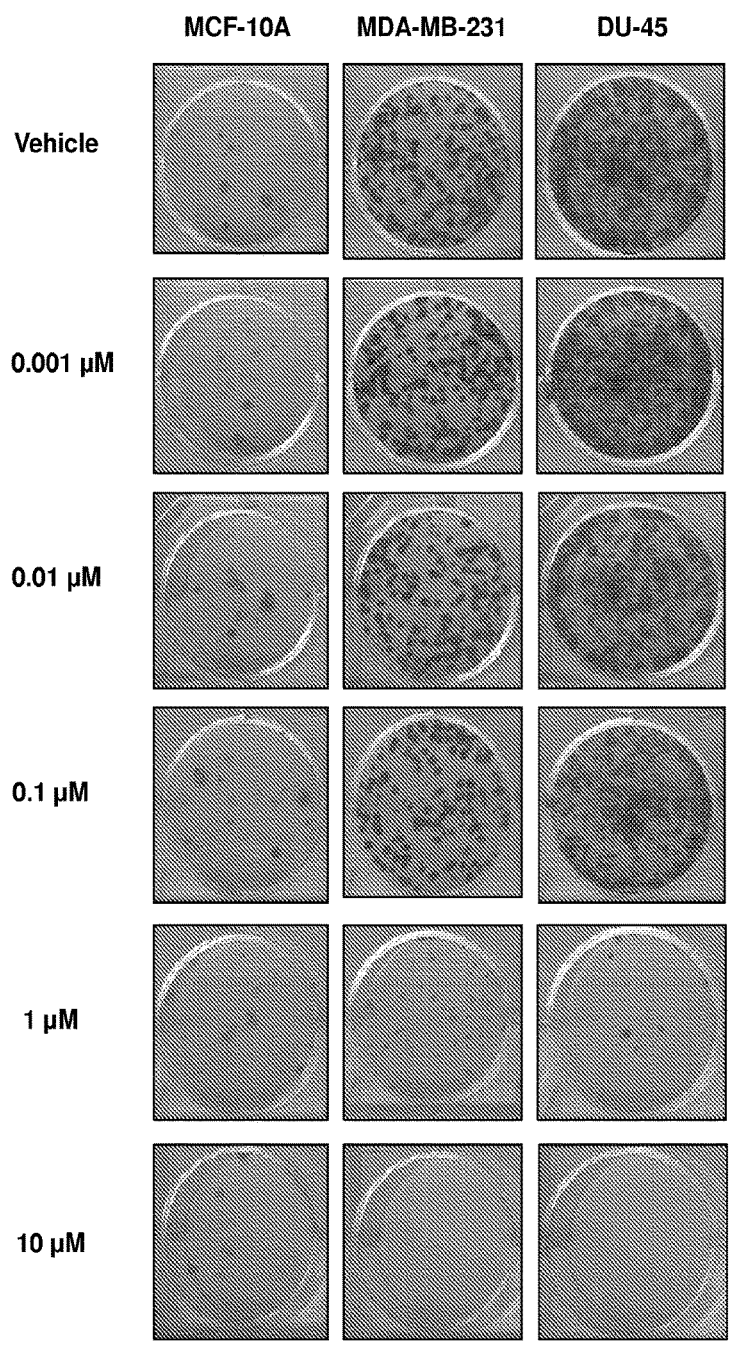
FIG. 2: Clonogenic Cell Survival Assays in Malignant and Non-malignant Cells MCF-10A (non-malignant) and malignant cell lines, MDA-MB-231 and DU145, were seeded at a density of 300 cells/well and treated with XB05 for 10 days at the concentrations indicated. The colonies were fixed and stained as described in the Methods.

XB05 has Cancer-Selective Antiproliferative Activity. XB05 was tested to determine its antiproliferative activity in a variety of human cell lines that are derived from malignant tissues or from non-malignant (immortalized but not transformed) cells and listed in FIG. 1B. As described in Materials and Methods, cells were treated with varying concentrations of XB05 for 72 h and evaluated using the MTT cell proliferation assay. The resulting values were normalized to the proliferation of untreated cells for each cell type, which revealed that XB05 has potent antiproliferative activity against most of the malignant cell lines tested (e.g. $GI_{50} < 500$ nM for DU145, U937, and MDA-MB-231 cells), but has a smaller inhibitory effect on the proliferation of non-malignant cells (FIG. 1C). Clonogenic cell survival assays were also conducted for some cell lines and are shown in FIG. 2. Based on the data shown in FIG. 1C, we chose three cell lines that had high, intermediate, or low sensitivity to XB05 for additional studies, with the goal of elucidating their differential responses to XB05. The selected cell lines were: U937 myeloid leukemia cells (high sensitivity to XB05), A549 non-small cell lung cancer cells (moderate sensitivity), and Hs27 non-malignant skin fibroblasts (low sensitivity).

Figure 3:
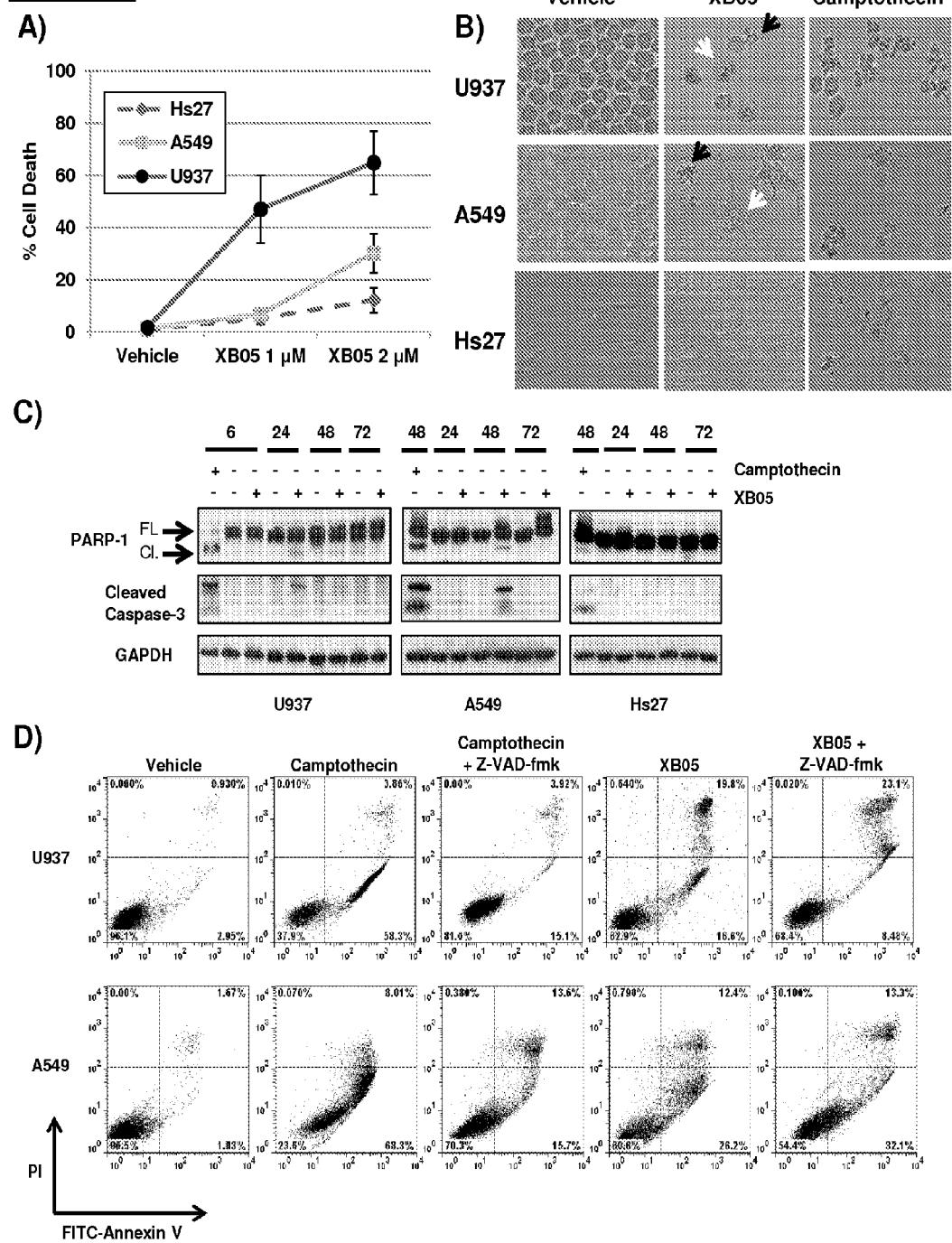
FIG. 3: XB05 Induces Apoptotic and Nonapoptotic Cell Death in Malignant Cell Lines. (A) Trypan blue exclusion assay for three human cell lines following treatment with XB05 for 72 h at the concentrations indicated. Data points represent the mean+/−SEM for three independent experiments. (B) Representative phase contrast microscopy images of cells treated with vehicle (72 h), XB05 (72 h with 1 µM for U937 and Hs27, or 2 µM for A549), or 6 µg/mL camptothecin (U937 for 6 h, A549 and Hs27 for 48 h). Cells undergoing apoptotic (black arrows) or non-apoptotic (white arrows) cell death are indicated. (C) Whole cell extracts from cells treated with vehicle, camptothecin, or XB05, as described in part B were western blotted for biochemical markers of apoptosis and GAPDH (loading control). Apoptosis is indicated by cleavage of full-length PARP-1 (116 kDa) to an 89 kDa fragment, and by appearance of bands (17 kDa, 19 kDa) recognized by an antibody specific to cleaved (activated) forms of caspase-3. (D) Flow cytometric analysis of annexin V-FITC/propidium Iodide (PI) staining for malignant cells treated with vehicle, camptothecin or XB05 as described in part B, in the presence or absence of the pan-caspase inhibitor Z-VAD-fmk (100 µM).
Figure 4:
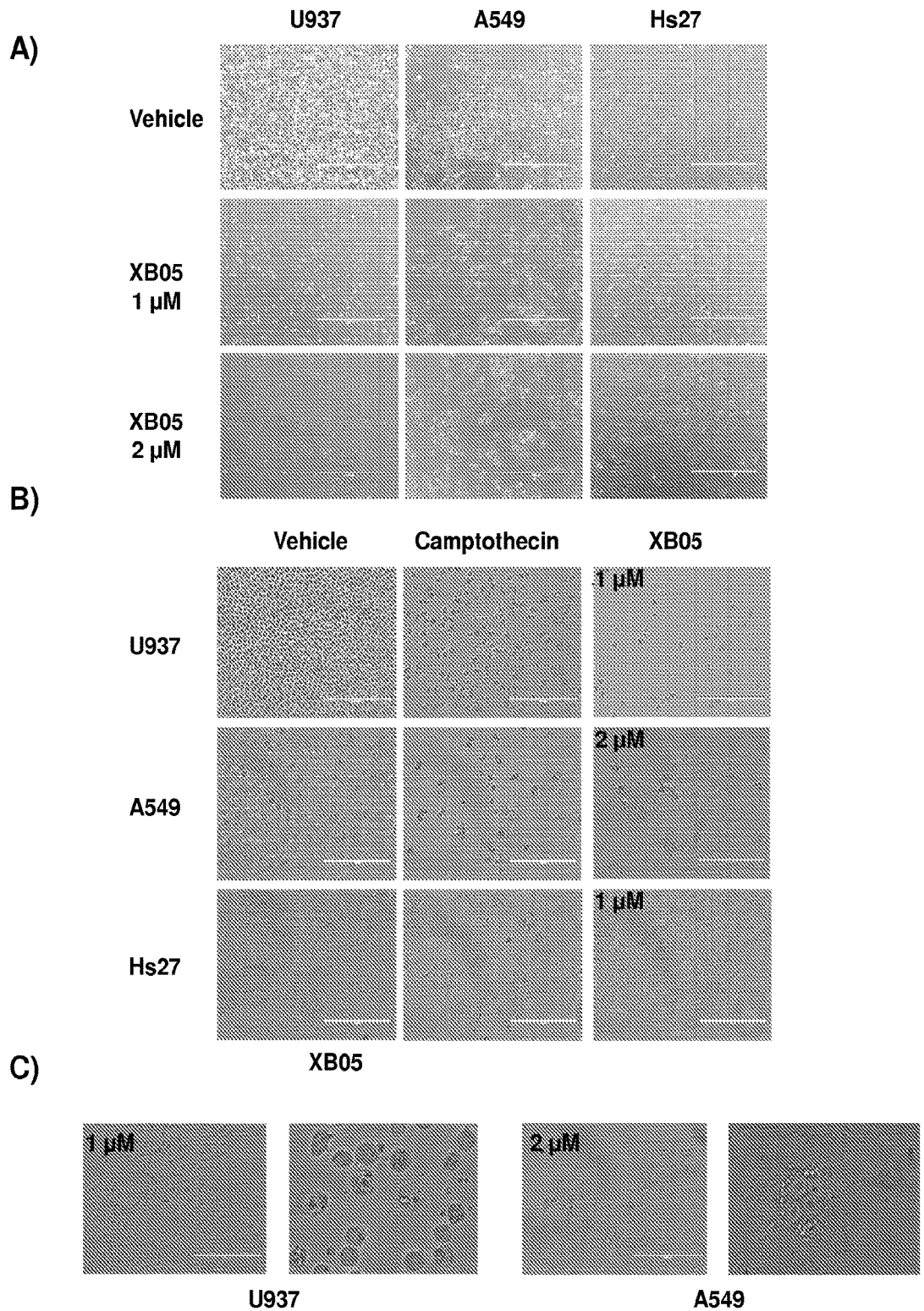
FIG. 4: Microscopic Examination of Cell Morphology in Malignant and Non-malignant Cells (A) Representative phase contrast microscopy images of malignant (U937, A549) and non-malignant (Hs27) cell lines treated for 72 h with XB05 at the concentrations indicated or with vehicle as control. Scale bar, 1000 µm. (B) Representative phase-contrast images of indicated cell lines treated with vehicle, 6 µg/mL camptothecin (6 h for U937 cells or 48 h for A549 and Hs27 cells), or XB05 for 72 h at the concentrations indicated in the figure. Scale bar, 200 µm. (C) Representative images of morphological changes associated with XB05-induced cell death (cell swelling, vacuolation, multinucleation) in U937 and A549 cells treated with XB05 as indicated for 72 h. Scale bar, 200 µm.
Figure 5:
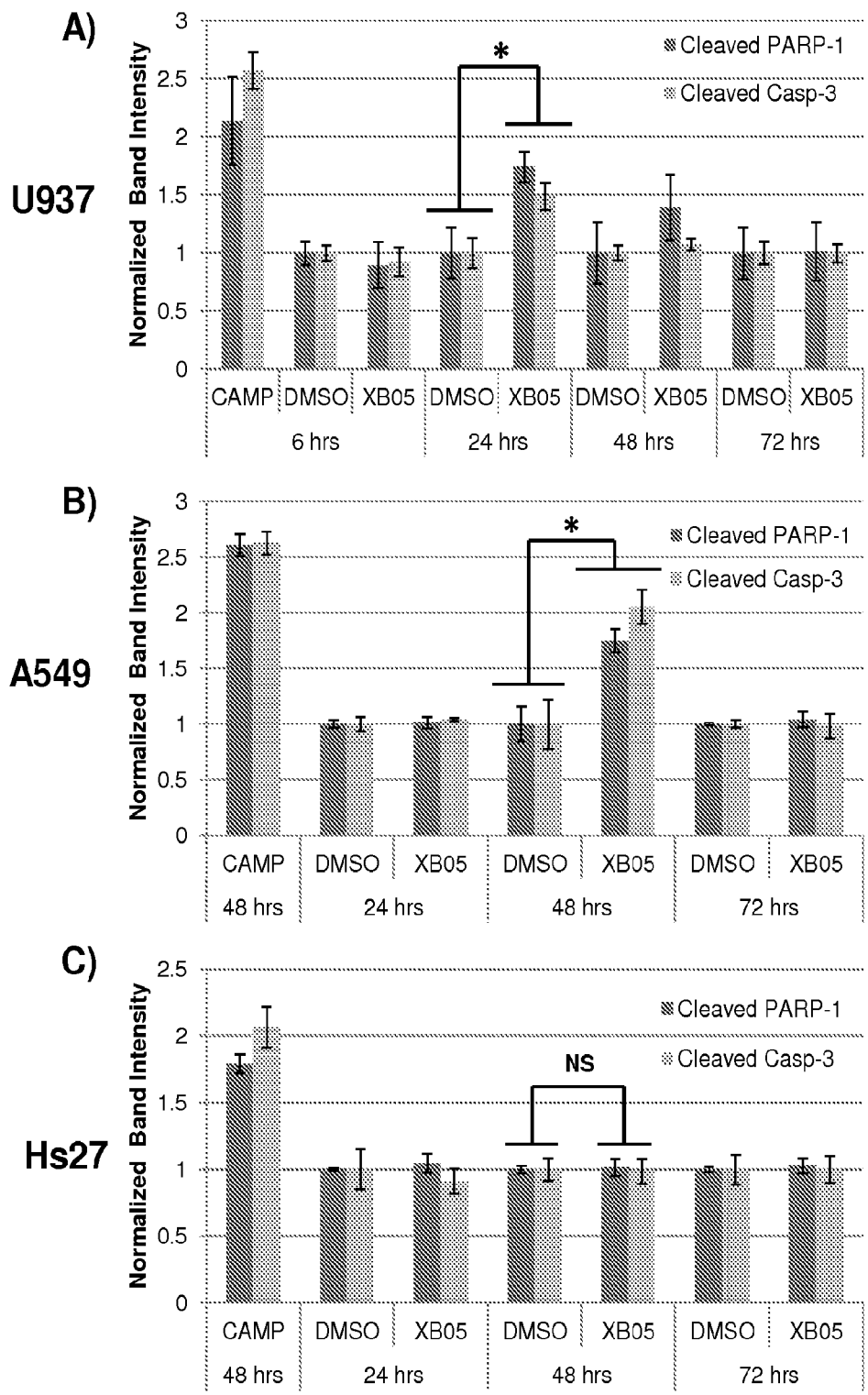
FIG. 5: Quantification of Cleaved PARP-1 and Caspase-3 Western Blot Band Intensities. The cell lines indicated (A-C) were treated with DMSO vehicle, XB05 (1 µM for U937 and Hs27, or 2 µM for A549), or 6 µg/mL camptothecin for the time points indicated. Densitometry was performed to quantify western blot band intensities (a representative blot is shown in FIG. 3C), and the values normalized to DMSO vehicle control at each time point. Bar graphs indicate the average band intensity for three independent experiments, +/−the standard error of the mean. Statistical significance for XB05 compared to vehicle is indicated (*$p \leq 0.05$)

XB05 Induces Apoptotic and Nonapoptotic Cell Death in Malignant Cell Lines. To determine whether the antiproliferative effects of XB05 are due to cytostasis or cytotoxicity, we next examined XB05-treated cells for physical, morphological, and biochemical markers of cell death. Trypan blue exclusion assays showed that XB05 induced robust cell death in U937 cells at 1 µM concentration, modest cell death in A549 cells at 2 µM, and lowest levels of cell death in the non-malignant Hs27 cells (FIG. 3A). Microscopic examination of cells confirmed these results and revealed that XB05 induced a mixture of cell morphologies (FIG. 3B and FIG. 4). For both U937 leukemia cells (which grow in suspension) and A549 lung cancer cells (adherent), treatment with XB05 led to some cells with classical apoptotic morphology and some with abnormal morphology characterized by cellular swelling, accumulation of perinuclear vesicles, and (in some cases) multinucleation (FIG. 3B and FIG. 4C). In contrast, camptothecin, which is a topoisomerase I inhibitor used here as a positive control for apoptosis induction, triggered cell death in all three cell lines predominantly by apoptosis (FIG. 3B and FIG. 4B). Next, we investigated the timing of cell death induction by western blotting for biochemical markers of apoptosis. In accord with the results described above, we observed PARP-1 and caspase-3 cleavage in all three cell lines following treatment with camptothecin, but only in the malignant cells after XB05 treatment (FIG. 3C and FIG. 5). These markers of apoptosis were apparent by 24 h after treatment with XB05 in U937 cells, but were seen later (48 h) in the less sensitive A549 cells (FIG. 3C and FIG. 5). Finally, to evaluate the relative contribution of apoptosis to XB05-induced cell death, we performed flow cytometric analyses of annexin/PI stained cancer cells that had been treated in the presence or absence of the pan-caspase inhibitor, N-benzyloxycarbonyl-Val-Ala-Asp-fluoromethylketone (Z-VAD-fmk). As expected, camptothecin treatment led to mainly apoptotic cells (seen in the annexin-positive/PI-negative quadrant in FIG. 3D), whereas XB05 treatment induced two distinct populations of cells corresponding to early apoptotic cells (annexin-positive/PI-negative) and late apoptotic or necrotic cells (annexin-positive/PI-positive) (FIG. 3D). Moreover, while the presence of Z-VAD-fmk strongly inhibited cell death in response to camptothecin, it had little effect on cell death in response to XB05, as determined by the proportion of cells staining positive for either annexin or PI (FIG. 3D). These data indicate that XB05-induced cell death can occur without apoptosis, which could be significant because the ability to evade apoptosis (via activation of various anti-apoptotic pathways) can be a hallmark of aggressive cancer cells and a major contributor to chemoresistance.

Figure 6:
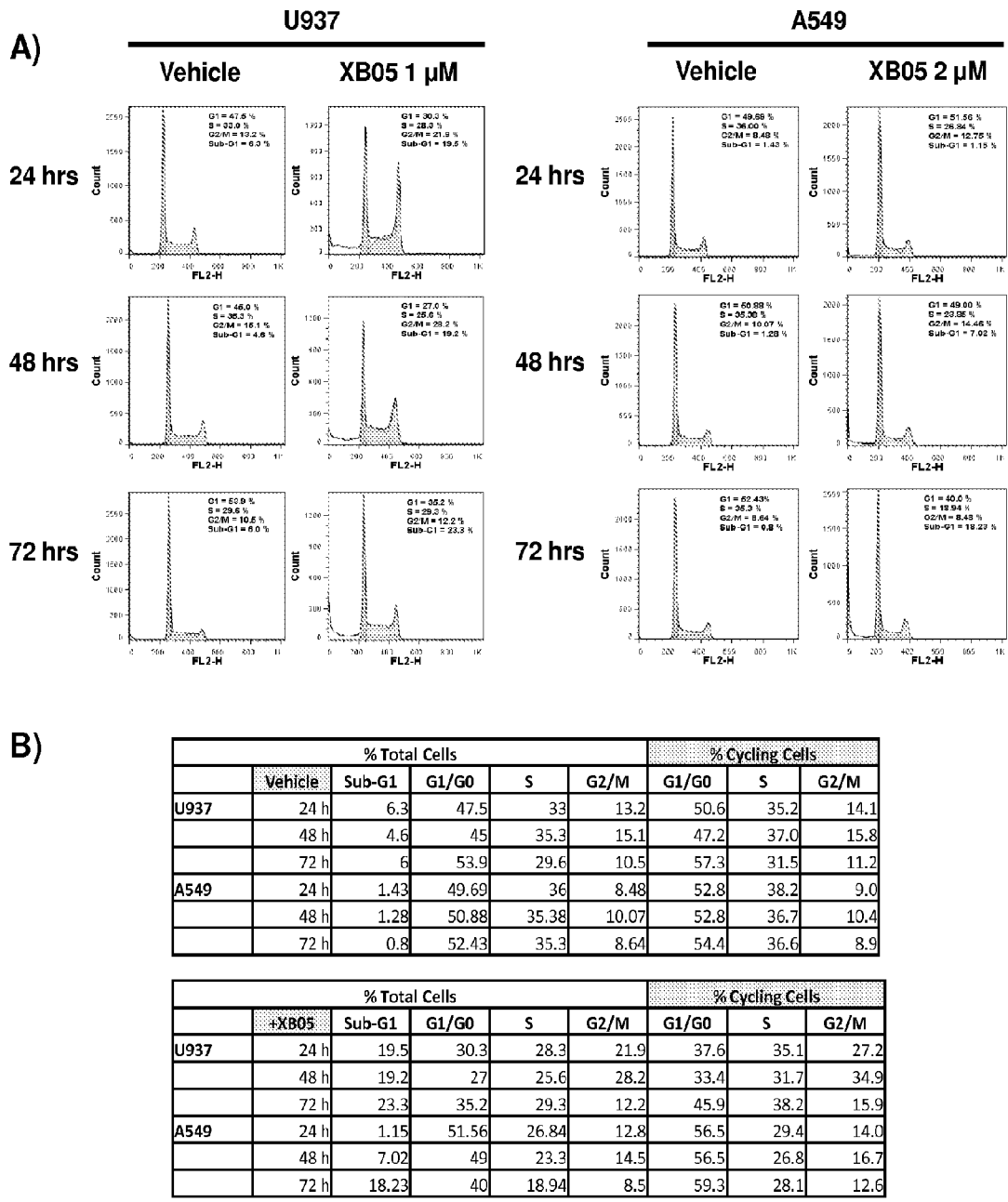
FIG. 6: DNA Content Analysis for Malignant Cells treated with XB05. (A) U937 and A549 cells were treated with XB05 at the concentrations indicated for 24, 48 and 72 h. At each time point, the cells were harvested and subjected to propidium iodide (PI) staining for DNA content analysis as described in Methods. (B) Tables showing percentage of cycling cells (non-SubG1) in various phases of the cell cycle after treatment with vehicle or XB05 as indicated in FIG. 6A.

XB05 Causes Transient G2/M Cell Cycle Arrest in U937 Cells. As determined by flow cytometric analysis of cells stained for DNA content, XB05-treated U937 cells displayed a pronounced increase in the proportion of cells in G2/M phase at 24 h, but this was reversible and the proportion in G2/M was reduced by 48 and 72 h (FIG. 6). In contrast, XB05-treated A549 cells showed only a very modest increase in the G2/M fraction, suggesting that cell death does not likely depend upon cell cycle arrest. However, these results may explain our observation of multinucleated cells because transient arrest in G2/M followed by cell cycle progression can result in mitotic catastrophe, consistent with the observed morphology (FIG. 3B, white arrows, and FIG. 4C). In agreement with the previous results, both malignant cell lines treated with XB05 exhibited a time-dependent increase in the percentage of op cells with sub-G1 DNA content (FIG. 6).

Figure 7:
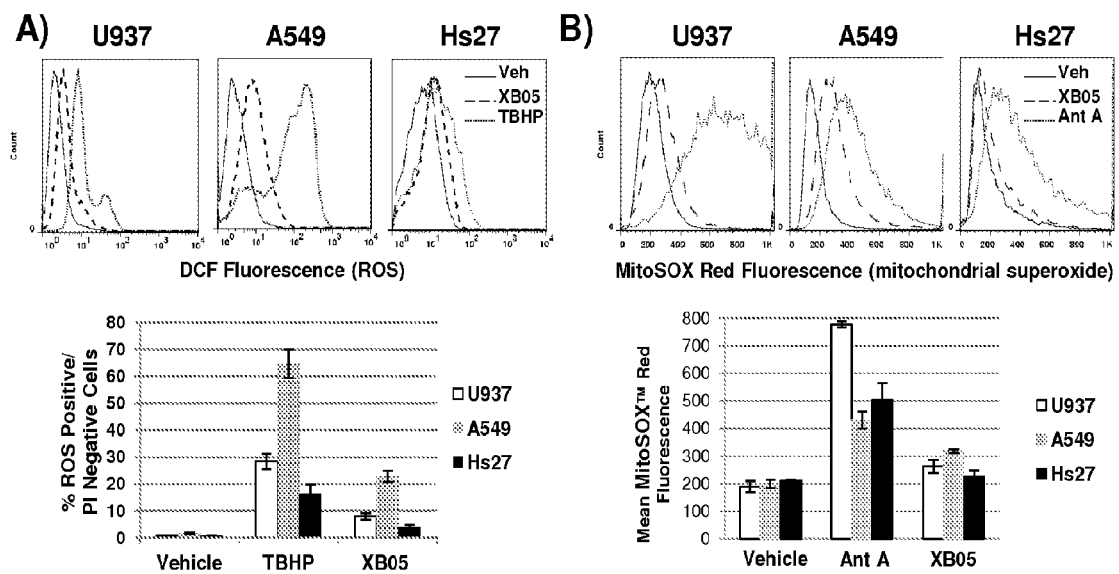
FIG. 7: XB05 Induces ROS. (A) Cells were treated with either vehicle, tert-butyl hydrogen peroxide (TBHP, 100 µM, 3 h) or XB05 (8 h with 1 µM for U937 and Hs27, or 2 µM for A549), then stained with carboxy-$H_2$DCFDA and PI for analysis by flow cytometry. Histograms illustrate representative data and bar graphs show the increase (over vehicle control) in the percentage of PI-negative (viable) cells with positive DCF fluorescence in each sample. Bars represent the mean+/−SEM from three independent experiments. Statistical comparisons showed that XB05 significantly increased ROS in all cell lines (*$p \leq 0.05$) and that both A549 and U937 had a significantly greater increase compared to Hs27 (*$p \leq 0.05$). (B) Cells were treated with XB05 as described in part A. As a positive control for superoxide production, cells were treated with Antimycin A (10 µM) for 1 h. Cells were harvested and subjected to MitoSOX™ Red staining for analysis by flow cytometry as described in Methods. Histograms illustrate representative data and bar graphs show the mean+/−SEM for three independent experiments. Statistical comparisons showed that XB05 significantly increased superoxide detection in A549 and U937 cells (*$p \leq 0.05$) but not in Hs27 non-malignant fibroblasts ($p=0.53$).

XB05 Induces Reactive Oxygen Species (ROS). Cells were treated with XB05 and analyzed for the presence of reactive oxygen species (ROS) by flow cytometry following staining with carboxy-$H_2$DCFDA, a cell-permeable, redox-sensitive probe that fluoresces after oxidation by ROS to dichlorofluorescein (DCF). As a positive control for oxidative stress, cells were treated with tert-butyl hydrogen peroxide (TBHP). The levels of ROS, measured by the percentage of viable cells (PT-negative) that stained positive for DCF, were elevated in all cell lines after 8 h of XB05 treatment, but were higher in the XB05-sensitive cell lines (A549 lung cancer and U937 leukemia) compared to the less sensitive, non-malignant Hs27 cells (FIG. 7A). To investigate a possible origin of XB05-induced ROS, we next examined if XB05 could induce an increase in mitochondrial superoxide levels. Mitochondria are a major source of endogenous ROS because single electrons which escape from the electron transport chain (ETC) can reduce molecular oxygen to superoxide anion. Superoxide can be rapidly converted to hydrogen peroxide by manganese superoxide dismutase (SOD2); thus mitochondria can be a source of both superoxide and hydrogen peroxide. To examine the effect of XB05 on mitochondrial superoxide production, we incubated XB05-treated cells with MitoSOX™ Red and analyzed the staining by flow cytometry as described in "Materials and Methods". MitoSOX™ Red is a derivative of hydroethidine (HEt), which due to its positive charge, preferentially accumulates within the mitochondrial matrix where oxidation of MitoSOX™ Red by superoxide generates the fluorescent product 2-Hydroxyethidium (2-OH-Et+). In these experiments, some cells were treated with antimycin A, a known inhibitor of Complex III in the ETC, as a positive control for increased superoxide production. Compared to the vehicle control, XB05 treatment for 8 h induced an increase in MitoSOX™ Red fluorescence in U937 and A549 malignant cells ($p<0.05$) but not in Hs27 non-malignant fibroblasts ($p=0.53$) (FIG. 7B).

Figure 8:
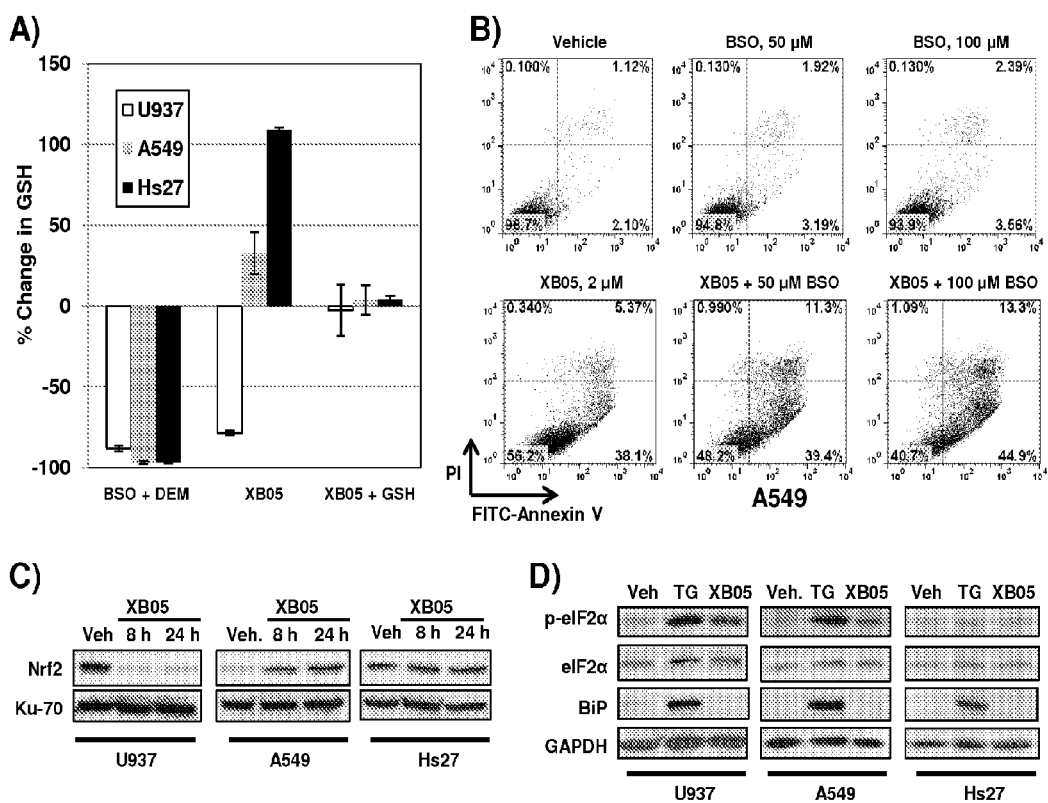
FIG. 8: XB05 Modulates Cellular Stress Responses. (A) A luminescence-based assay for reduced glutathione (GSH) content in cells treated 24 h with XB05 (1 µM for U937 and Hs27, or 2 µM for A549), in the absence or presence of 5 mM GSH. Some cells were treated with buthionine sulfoximine (BSO, 200 µM) plus diethyl maleate (DEM, 1 mM) for 3 h as a positive control for GSH depletion. Bar graph indicates mean+/−SEM from three independent experiments. Raw data are provided in FIG. 9. (B) Flow cytometric analysis of Annexin/PI staining for A549 cells treated 72 h with vehicle or 2 µM XB05 in the absence or presence of BSO as indicated. Data are representative of three independent experiments and comparable data for U937 cells are shown in FIG. 10. (C) Western blot for Nrf2 in nuclear extracts from cells treated as in part A for either 8 h or 24 h. Membranes were stripped and reprobed for Ku-70 as a loading control. Data shown are representative of three individual experiments for each cell line and quantitative data are shown in FIG. 10. (D) Western blot for phospho-eIF2α (Ser51), total eIF2-α, BiP/Grp78, and GAPDH (loading control) in whole cell extracts from cell lines treated as indicated for 24 h with concentrations of XB05 described in part A. Thapsigargin (TG, 2 µM) was used as a positive control for induction of endoplasmic reticulum (ER) stress. Data shown are representative of three individual experiments for each cell line and quantitative data are shown in FIG. 10.
Figure 10:
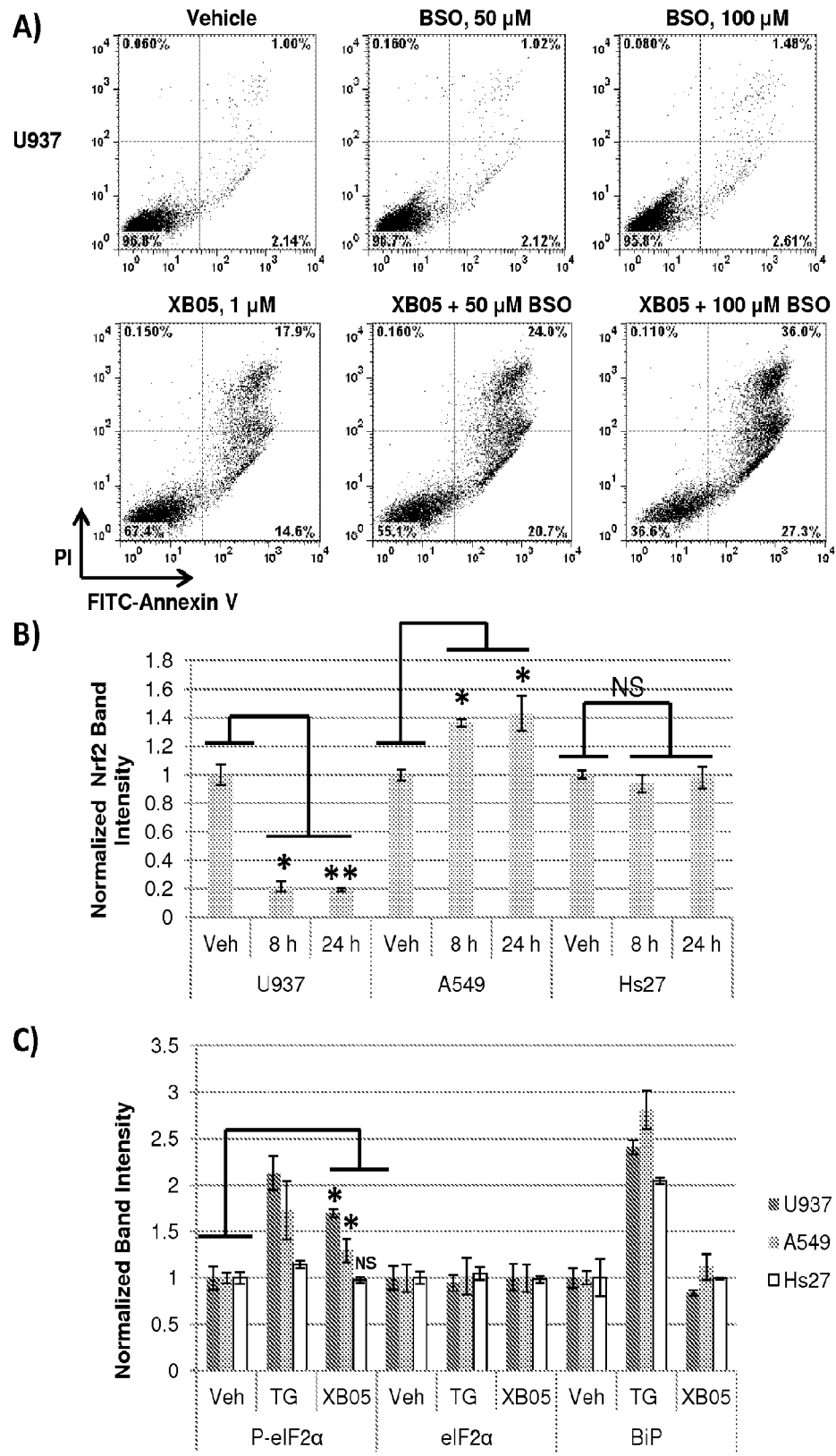
FIG. 10: (A) Flow cytometric analysis of Annexin/PI staining for U937 cells treated with vehicle or XB05 (1 µM)+/−BSO as indicated for 72 h. Data shown are representative of three independent experiments. (B) The cell lines indicated were treated with DMSO vehicle or XB05 (1 µM for U937 and Hs27, or 2 µM for A549) for the timepoints indicated. Densitometry was performed to quantify western blot band intensities for Nrf-2 (representative blot shown in FIG. 8C). (C) The cell lines indicated were treated with DMSO vehicle, XB05 (1 µM for U937 and Hs27, or 2 µM for A549) or Thapsigargin positive control (2 µM) for 24 h. Densitometry was performed to quantify western blot band intensities for phospho-eIF2α (ser51), total eIF2α and BiP (representative blot shown in FIG. 8D). All values were normalized to DMSO vehicle control. Bar graphs indicate the average band intensity for three independent experiments, +/−the standard error of the mean. Statistical significance for XB05 compared to vehicle is indicated (*$p \leq 0.05$ and **$p \leq 0.01$).

XB05 Modulates Cellular Stress Responses. Following oxidative and other stresses, cells can activate protective responses to neutralize reactive species and thereby limit damage to DNA, lipids, and proteins. These protective factors can include antioxidant molecules, such as the tripeptide, glutathione, and transcription factors, such as NF-E2-related Factor 2 (Nrf2), that mediate expression of stress response genes. Therefore, we examined the effect of XB05 on some of these pathways using a luminescence-based reporter assay to monitor levels of the reduced form of glutathione (GSH) and western blotting to detect Nrf2. The GSH-Glo™ assay is based on conversion of a luciferin derivative (luciferin-NT) to luciferin by glutathione-S-transferase in the presence of reduced glutathione, which is obtained from lysed cells in each treatment sample. Luciferin acts as a substrate for firefly luciferase to produce a luminescent signal which is proportional to the amount of GSH present. We found that treatment of the U937 cells with 1 μM XB05 resulted in a depletion of reduced GSH, which was comparable to that seen with the positive control treatment, consisting of a combination of 200 μM buthionine sulfoximine (BSO, an inhibitor of GSH synthesis) and 1 mM diethyl maleate (DEM, a GSH conjugating agent) (FIG. 8A and FIG. 9). In contrast, XB05 treatment of A549 and Hs27 cells led to approximately 1.3-fold and 2-fold increases in GSH, respectively (FIG. 8A and FIG. 9), suggesting that the decreased sensitivity of these cell lines relative to U937 could be due to their enhanced ability to induce glutathione synthesis as an adaptive response to the drug, Addition of exogenous GSH to the medium inhibited the ability of XB5 to modulate GSH levels (FIG. 8A and FIG. 9). We performed similar experiments to assess whether further depletion of GSH would increase the activity of XB05 towards malignant cells. Thus, we treated A549 and U937 cells with XB05 in the presence of sub-lethal concentrations (50 and 100 μM) of the glutathione synthesis inhibitor, BSO, for 72 h and then analyzed cell death by annexin/PI staining. We observed that combined treatment with BSO and XB05 led to enhanced cytotoxicity compared to XB05 treatment alone, as indicated by an increase in both apoptotic and late apoptotic/necrotic cells (FIG. 8B and FIG. 10A). Next, we examined XB05-treated cells for activation of Nrf2, a redox-regulated transcription factor that translocates to the nucleus in response to oxidative or electrophilic stress. Nrf2 can activate transcription of various ROS detoxifying enzymes, including γ-glutamyl-cysteine synthetase (γ-GCS), the rate-limiting enzyme for glutathione synthesis. Nuclear extracts from the three cell lines treated with XB05 for 8 or 24 h were assessed for the presence of Nrf2 and displayed differential responses (FIG. 8C and FIG. 10B). In U937 cells, there was a decrease in nuclear Nrf2 after XB05 treatment, suggesting that the high sensitivity of these cells to XB05 could be related to its inhibitory effect on the Nrf2 antioxidant response pathway. This could be significant because high Nrf2 expression appears to drive chemoresistance in acute myeloid leukemia. In A549 cells (which have constitutive activation of this pathway), we observed a slight increase in nuclear levels of Nrf2, whereas no change was apparent for Hs27 cells. The latter result indicates that the observed increase in GSH levels for XB05-treated Hs27 cells is probably Nrf2-independent. Finally, we analyzed cells for phosphorylated eukaryotic initiation factor 2α (p-eIF2α), which is another common marker for cellular stress. Phosphorylation of eIF2α can be mediated by a variety of stress-induced kinases and results in inhibition of general translation, while allowing preferential translation of transcripts that encode for stress-relieving proteins. In these experiments, we used thapsigargin, an inducer of endoplasmic reticulum (ER) stress, as a positive control. We observed strongest induction of p-eIF2α in U937 cells (highly sensitive to XB05), followed by A549 (moderately sensitive), and Hs27 cells (least sensitive) (FIG. 8D and FIG. 10C). XB05 treatment did not lead to significant upregulation of BiP/Grp78 (an ER chaperone and marker of ER stress) in any of the cell lines (FIG. 8D and FIG. 10C), suggesting that XB05 may not induce ER stress or the unfolded protein response (UPR). Interestingly, phosphorylation of eIF2α in the absence of BiP/Grp78 induction can be associated with activation of pro-apoptotic pathways rather than cytoprotective responses.

Figure 11:
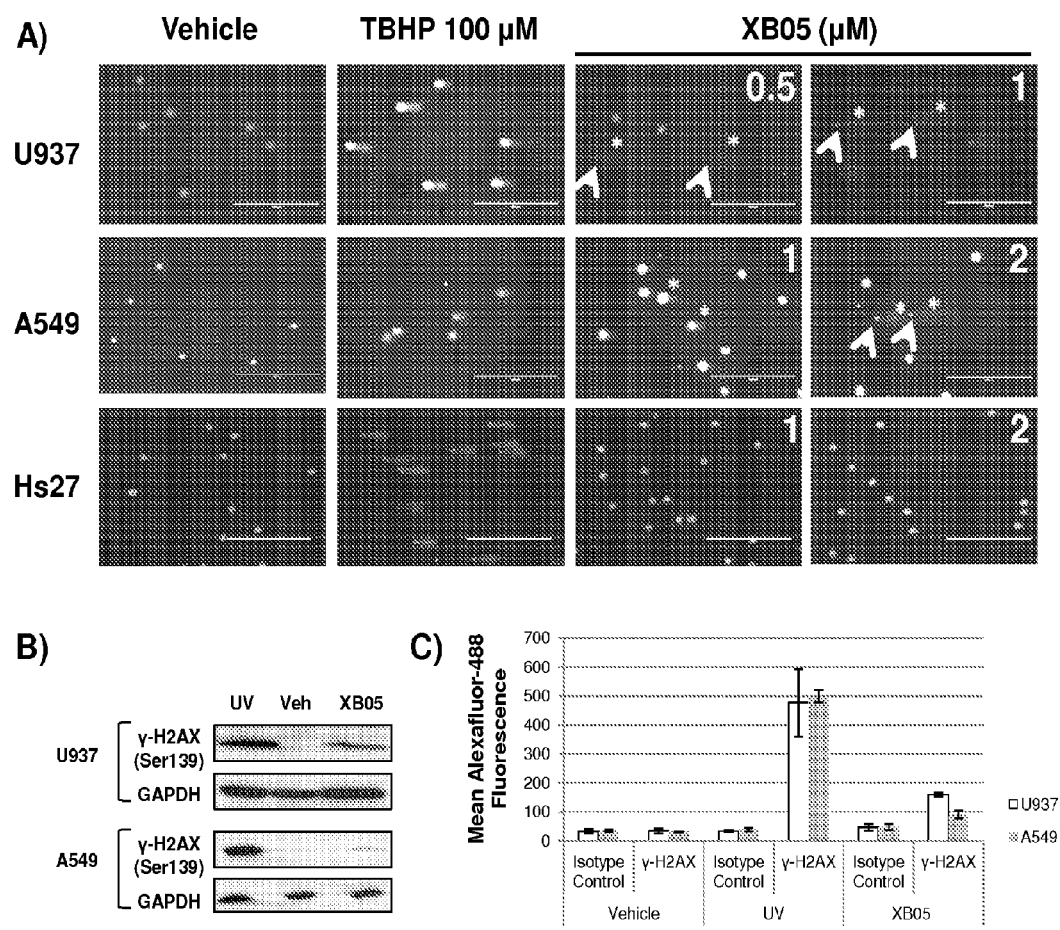
FIG. 11: XB05 Induces DNA Damage in Malignant Cells. (A) Alkaline comet assays for detection of DNA damage for cells treated as indicated for 72 h. TBHP was a positive control for oxidative DNA damage. Decreased DNA fluorescence in nucleoid comet heads (arrows) and increased smearing of DNA into comet tails (asterisks) is indicated. Scale bar, 400 µm. Data shown are representative of at least two individual experiments for each cell line. (B) Western blot analysis for γ-H2AX and GAPDH (loading control) in whole cell extracts from cells treated with vehicle, UV irradiation (800 µJ, positive control for DSBs), or XB05 (1 µM for U937, 2 µM for A549) after 24 h. Images shown are representative of three individual experiments in each cell line. (C) Flow cytometric detection of γ-H2AX in cells treated as described in part B. Bar graph represents mean+/−SEM for 3 individual experiments in each cell line. Statistical comparison indicated significant differences between vehicle and XB05-treated groups in both cell lines (*$p \leq 0.05$).

XB05 Induces DNA Damage in Malignant Cells. The cytotoxicity of excess ROS can be due largely to DNA damage, especially double strand breaks (DSB). To determine if XB05 induced DNA damage, we performed alkaline comet assays for cells treated with either XB05 or TBHP positive control. Using this single cell electrophoresis method, damaged DNA appears as a comet "tail". After treatment with THBP, comet tails could be observed in all cell lines (FIG. 11A). In contrast, treatment with XB05 led to comet tails only in the malignant cell lines, U937 and A549, with no evidence of DNA damage in the non-malignant Hs27 cells at comparable concentrations (FIG.

11A). To confirm that the DNA damage involves DSB, we conducted western blot analysis for γ-H2AX (histone H2AX phosphorylated at serine 139), which is a specific marker for DSB. UV irradiation was used as a positive control. We found that XB05 induces γ-H2AX within 24 h in both U937 and A549 cell lines (FIG. 11B). The result was confirmed by flow cytometry (FIG. 11C), with XB05-treated cells showing a 4.5-fold (U937) and 2.9-fold (A549) increase in γ-H2AX staining compared to vehicle-treated controls ($p<0.05$).

Figure 12:
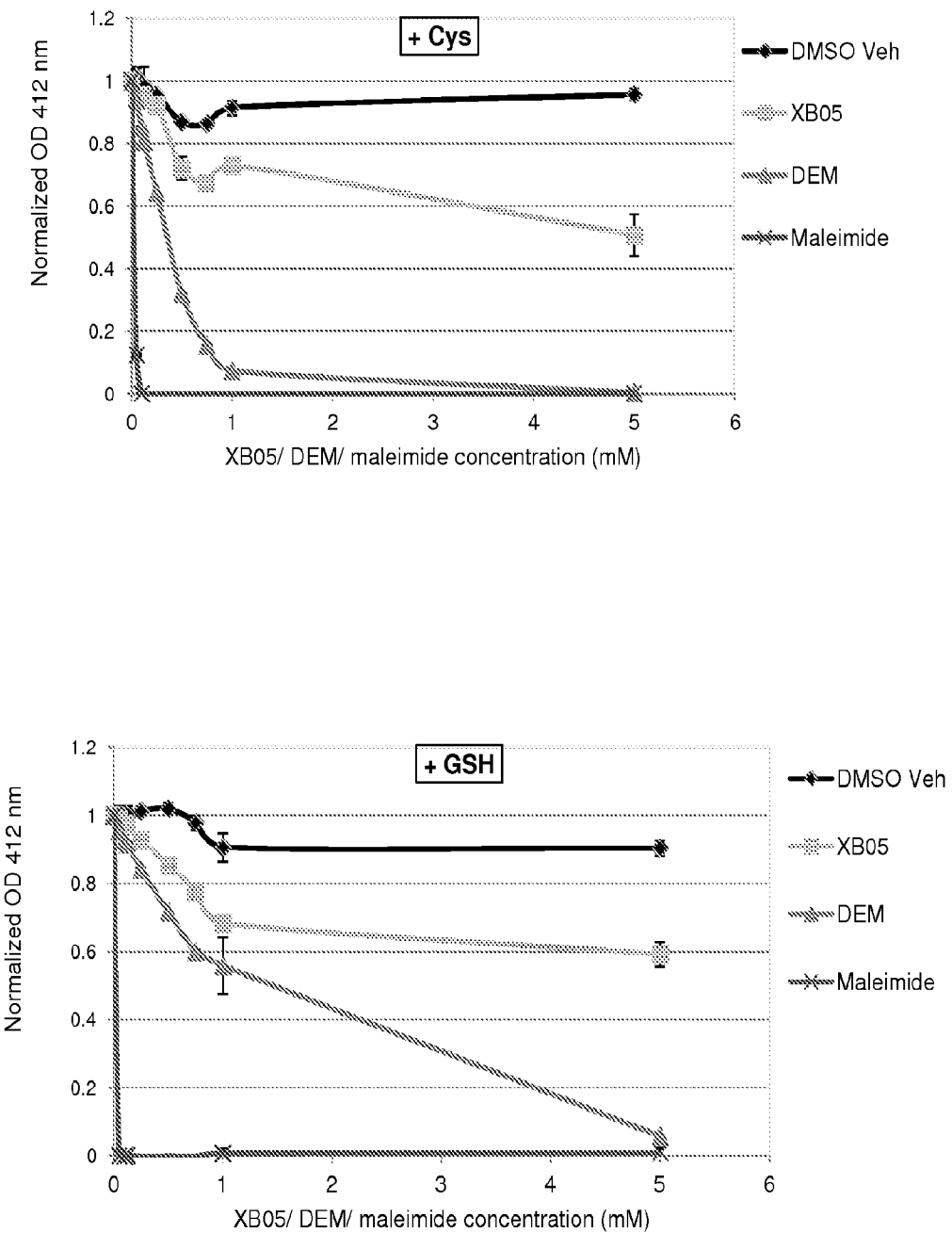
FIG. 12: XB05 is Weakly Reactive with Thiols In Vitro: 0.25 mM Cysteine (Cys, top panel) or glutathione (GSH, bottom panel) were incubated with XB05, diethyl maleate (DEM), or maleimide at the indicated concentrations, or with an equivalent amount of vehicle (DMSO), for 30 min at 37° C. 5,5'-Dithiobis-2-nitrobenzoic acid (DTNB) assays were conducted as described in Methods. Absorbance for triplicate wells was determined at 412 nm. Points represent the mean and standard deviation for triplicate wells. Data shown are representative of two independent experiments.
Figure 13:
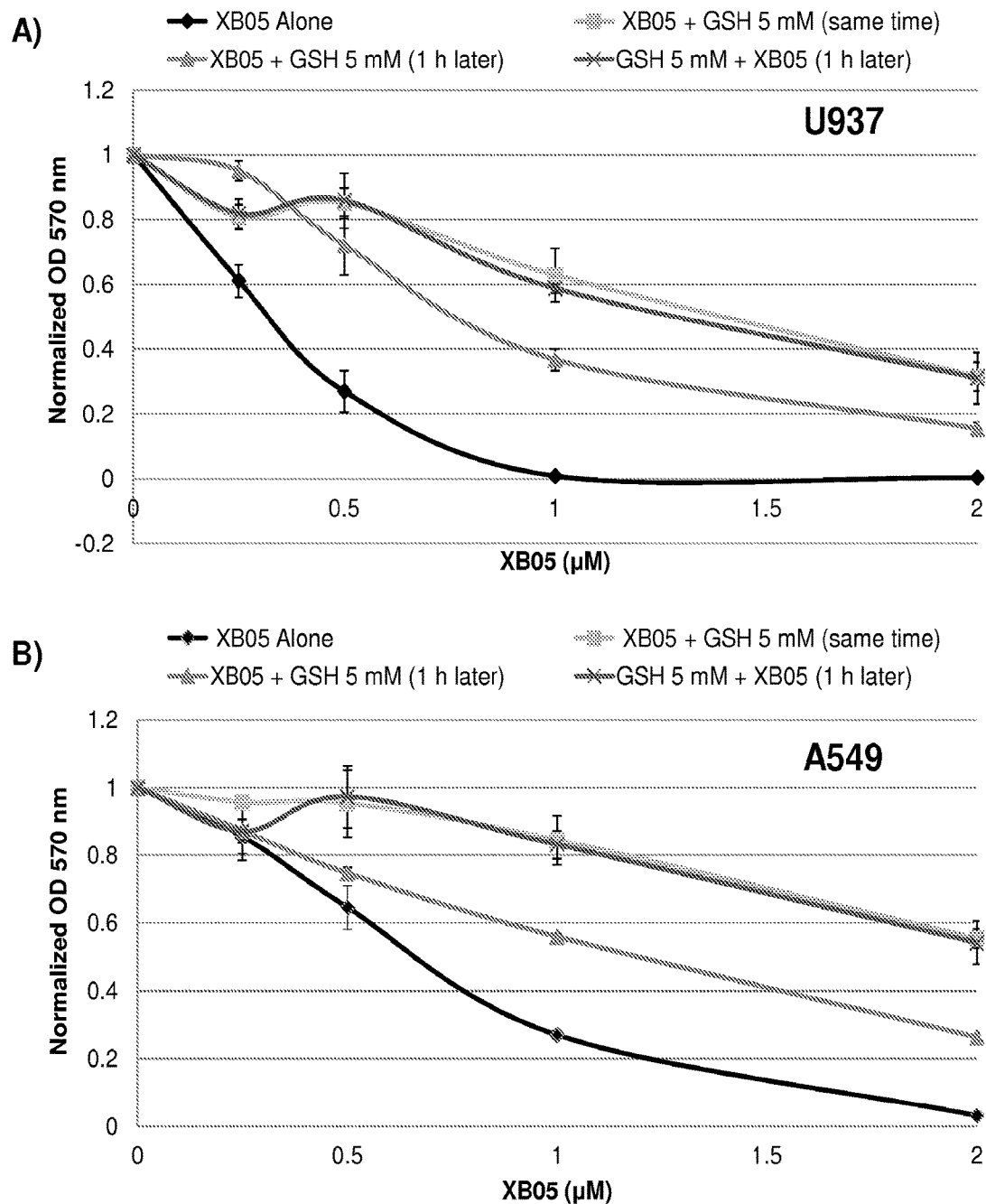
FIG. 13: Effect of Addition Sequence on the Ability of GSH to Inhibit the Antiproliferative Effects of XB05. MTT proliferation assays for (A) U937 and (B) A549 cells treated with XB05 in combination with reduced glutathione (GSH) as indicated for 72 h. Data shown is the average normalized OD value for four replicate wells in one experiment, +/−the standard deviation of the mean.

XB05 is Reactive with Cysteine and Glutathione In Vitro. Reaction of XB05 with NAC or GSH could potentially inhibit XB05 activity by sequestering the compound in the medium and prevent it from entering cells. We examined the in vitro reactivity of XB05 with relevant thiols using the 5,5'-dithiobis-2-nitrobenzoic acid (DTNB) assay. This is a colorimetric assay for free sulfhydryl determination based on the reaction of DTNB (a disulfide) with thiol groups to form 2-nitro-5-thiobenzoate (NTB), which ionizes to $NTB^{2-}$ dianion in alkaline aqueous solution. $NTB^{2-}$ has a yellow color which can be quantified by measuring absorbance of visible light at 412 nm. We incubated increasing concentrations XB05 (or an equivalent amount of vehicle as control) with the biological thiols, glutathione and cysteine (Cys), and monitored conversion of DTNB to $NTB^{2-}$, as indicated in FIG. 12. As positive controls, we also tested diethyl maleate (DEM) and maleimide, two well-known thiol-reactive electrophiles. We observed that when incubated with Cys or GSH at pH 8 for 30 min at 37° C., XB05 could lead to depletion of free thiols (presumably by reacting with Cys or GSH) only when present at very high concentrations, e.g. 5 mM XB05 led to 40-50% depletion (FIG. 12). Maleimide was more reactive and could completely deplete free Cys or GSH under the same conditions (FIG. 12). DEM was less reactive than maleimide, but still more reactive than XB05 (FIG. 12). We examined whether the protective effects of GSH in cell cultures assays depended on when it was added relative to XB05. The results of these studies indicate that adding GSH 1 h after XB05 decreases (but does not fully block) its protective activity compared to when it is added before or at the same time (FIG. 13).

Figure 14:
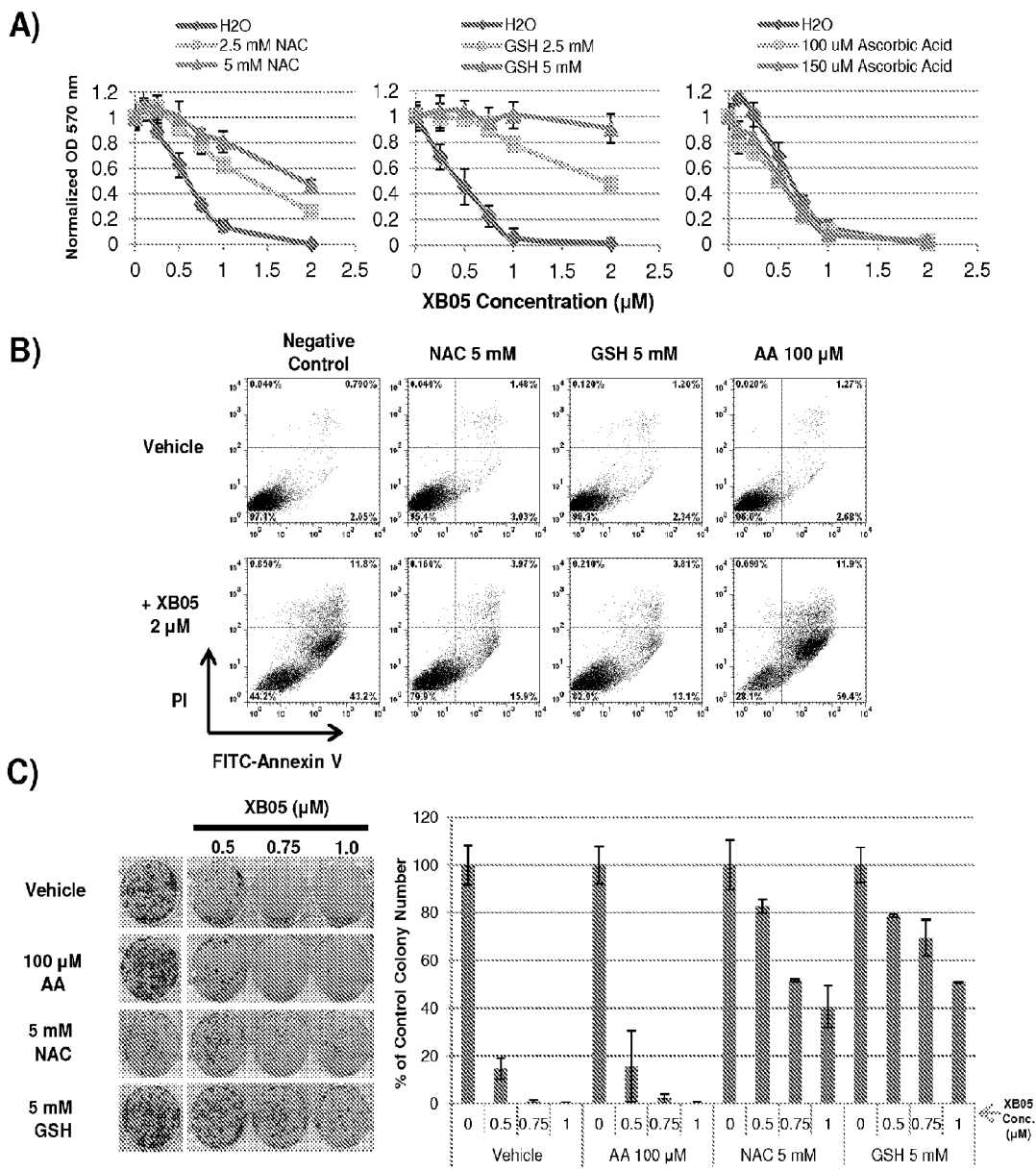
FIG. 14: Thiol-based Antioxidants Inhibit the Antiproliferative and Cytotoxic Effects of XB05 in A549 Cells. (A) MTT proliferation assays for A549 cells treated with XB05 in combination with antioxidants N-acetyl cysteine (NAC), reduced glutathione (GSH) or ascorbic acid (AA) as indicated for 72 h. (B) Flow cytometric analysis of Annexin/PI staining for A549 cells treated with vehicle or XB05+/−antioxidants for 72 h. (C) Clonogenic cell survival assays were conducted in A549 cells treated as indicated and grown in culture for 10 days (see Methods). Bar graph indicates mean values (+/−SEM) for colony growth inhibition from 3 independent experiments. MTT and flow cytometric assays were also performed in U937 cells (see FIG. 15) and gave the same results.
Figure 16:
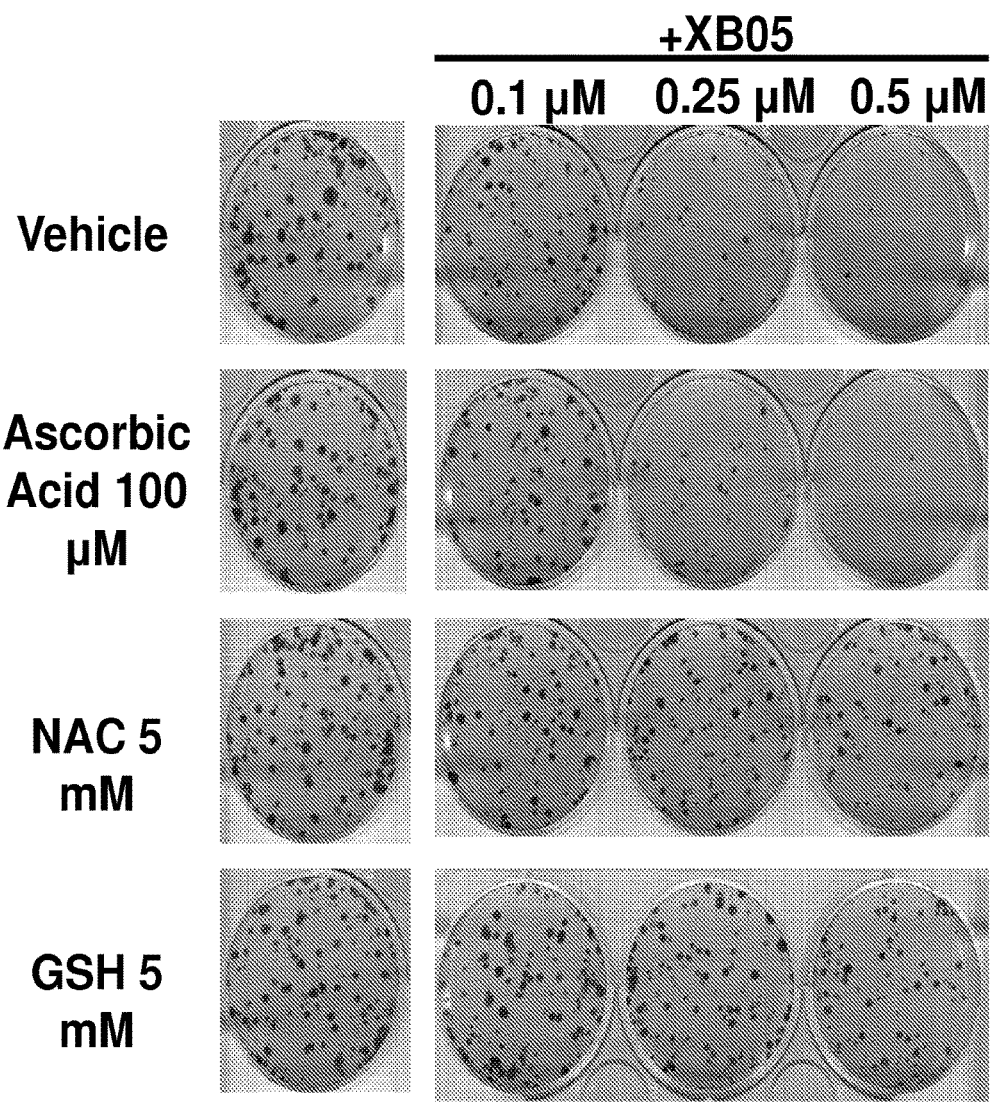
FIG. 16: Thiol-based Antioxidants Inhibit the Antiproliferative and Cytotoxic Effects of XB05 in MDA-MB-231 Cells. Clonogenic cell survival assays were conducted with MDA-MB-231 cells treated as indicated and grown in culture for 10 days (see Methods).
Figure 17:
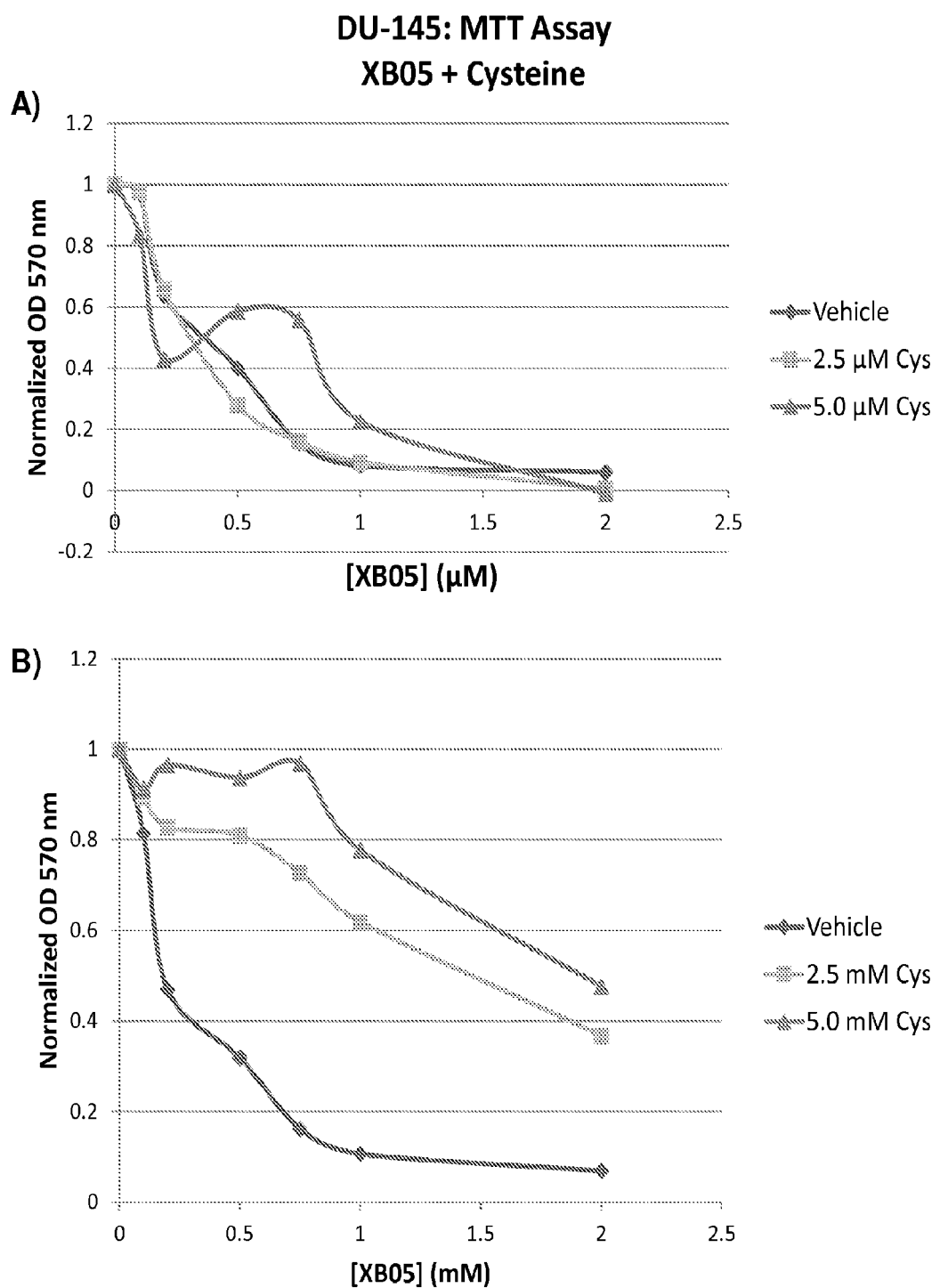
FIG. 17: Thiol-based Antioxidants Inhibit the Antiproliferative and Cytotoxic Effects of XB05 in DU-145 Cells. (A) MTT proliferation assays for DU-145 cells treated with XB05 in combination with micromolar concentrations (up to 5 µM) of cysteine for 72 h. (B) MTT proliferation assays for DU-145 cells treated with XB05 in combination with millimolar concentrations (up to 5 mM) of cysteine for 72 h. (C) MTT proliferation assays for DU-145 cells treated with XB05 in combination with micromolar concentrations (up to 5 µM) of N-acetyl cysteine (NAC) for 72 h. (D) MTT proliferation assays for DU-145 cells treated with XB05 in combination with millimolar concentrations (up to 5 mM) of N-acetyl cysteine (NAC) for 72 h. (E) MTT proliferation assays for DU-145 cells treated with XB05 in combination with micromolar concentrations (up to 5 µM) of reduced glutathione (GSH) for 72 h. (F) MTT proliferation assays for DU-145 cells treated with XB05 in combination with millimolar concentrations (up to 5 mM) of reduced glutathione (GSH) for 72 h. (G) MTT proliferation assays for DU-145 cells treated with XB05 in combination with micromolar concentrations (up to 100 µM) of L-ascorbic acid (AA) for 72 h.
Figure 17:
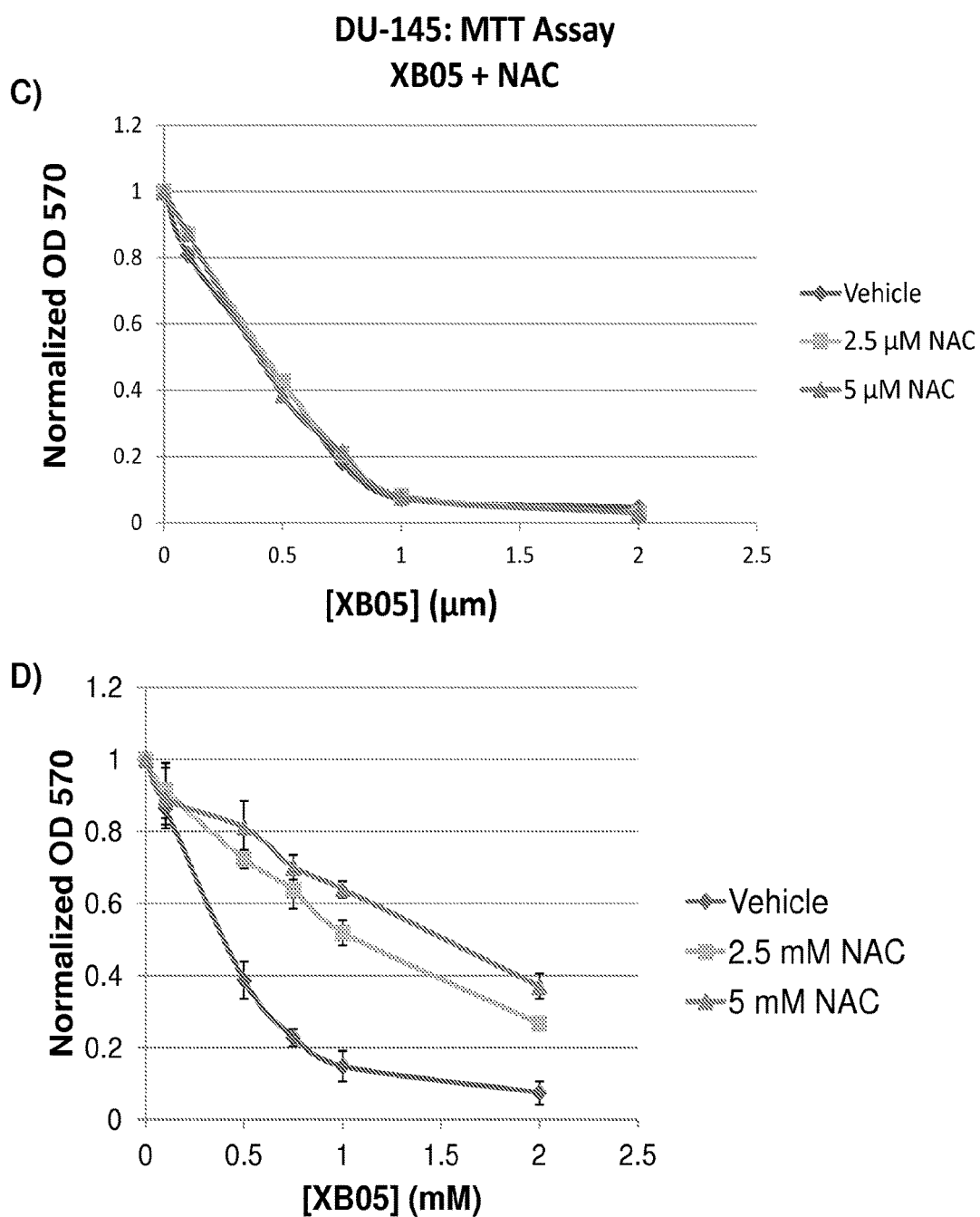
Figure 17:
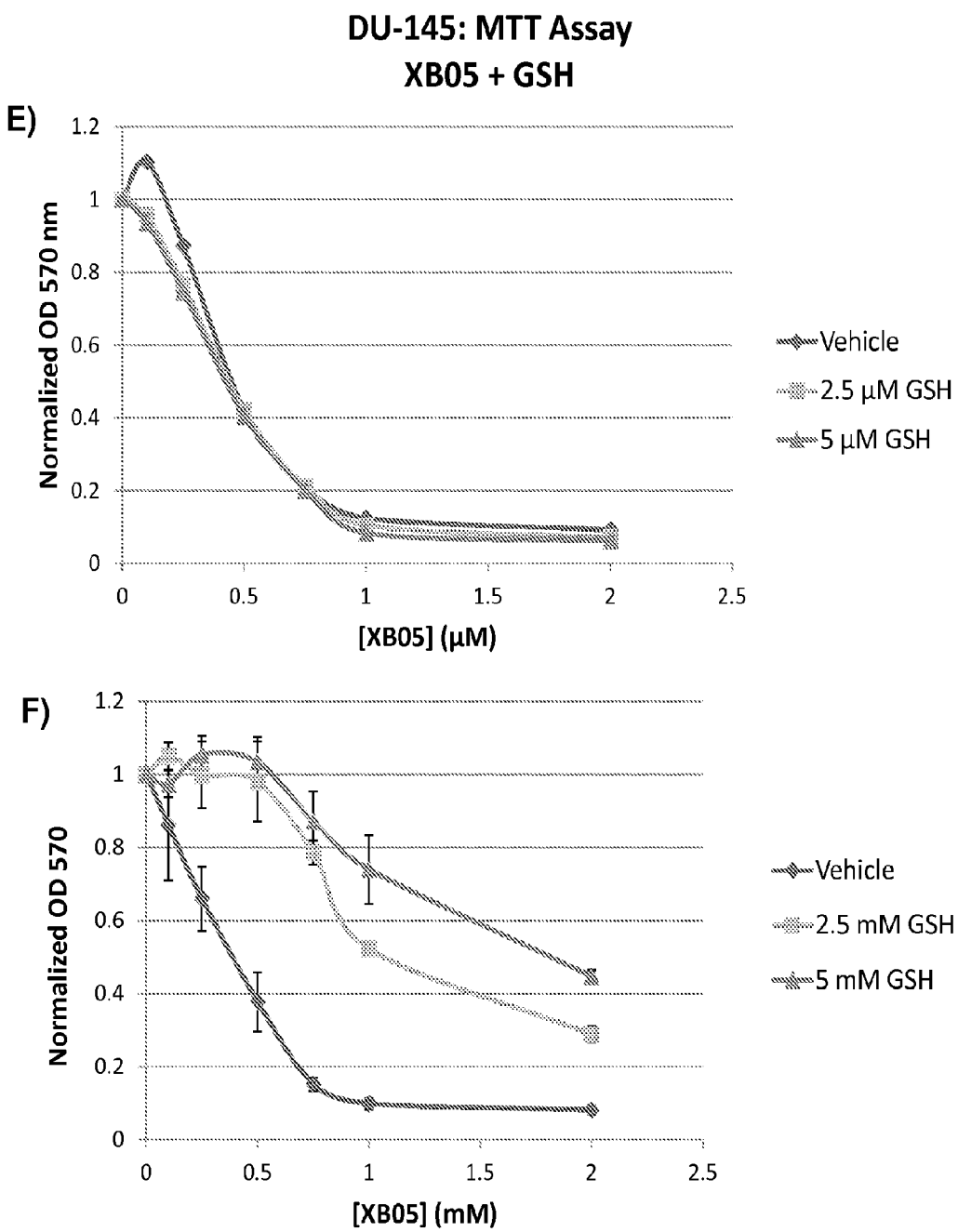
Figure 17:
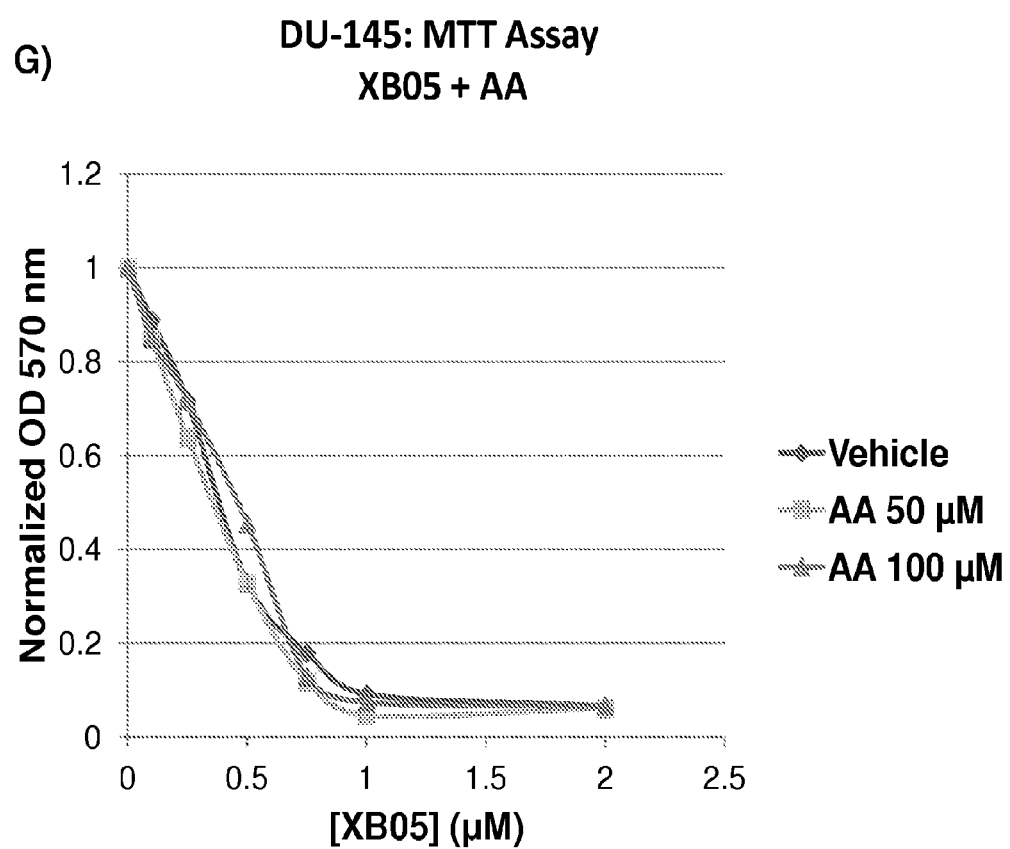

Exogenous Thiol Antioxidants Inhibit the Antiproliferative and Cytotoxic Effects of XB05. We conducted MTT proliferation assays for A549 cells using increasing concentrations of XB05 in the presence of antioxidants, including N-acetyl cysteine (NAC), reduced glutathione (GSH), or L-ascorbic acid (AA), used at concentrations reported in the literature to have antioxidant effects without cytotoxicity. We found that the thiol-based antioxidants, NAC and GSH, could diminish the antiproliferative effects of XB05, while AA had no effect (FIG. 14A). NAC and GSH also protected cells from XB05-induced apoptosis and nonapoptotic cell death (FIG. 14B), and abrogated the effect of XB05 on clonogenic survival (FIG. 14C). Again, ascorbic acid treatment had no protective effect in these assays, and even slightly enhanced the pro-apoptotic activity of XB05 (FIG. 14B). MTT proliferation assays and Flow cytometric assays using U937 cells showed that NAC and GSH (but not AA) could also protect these cells from the antiproliferative and cytotoxic effects of XB05 (FIG. 15). Clonogenic survival assays using MDA-MB-231 cells showed that NAC and GSH at 5 mM (but not AA at 100 µM) could also protect these cells from the cytotoxic effects of XB05 (FIG. 16). MTT proliferation assays for DU-145 cells in the presence micromolar (up to 5 µM) and millimolar (up to 5 mM) concentrations of antioxidants cysteine (Cys), N-acetyl cysteine (NAC), or reduced glutathione (GSH), show an enhanced antiproliferative effect in the millimolar concentration range (FIGS. 17A, 17B, 17C, 17D, 17E, and 17F); no antiproliferative effect was apparent with L-ascorbic acid (AA) up to 100 µM (FIG. 17G). Clonogenic survival assays with U937 cells using 100 µM of the non-thiol antioxidant BHA (butylated hydroxyanisole) cells had no protective effect from XB05 activity (data not shown).

EXAMPLE SET B

Example B1

XB05 Forms Covalent Bonds with Thiols

Figure 18:
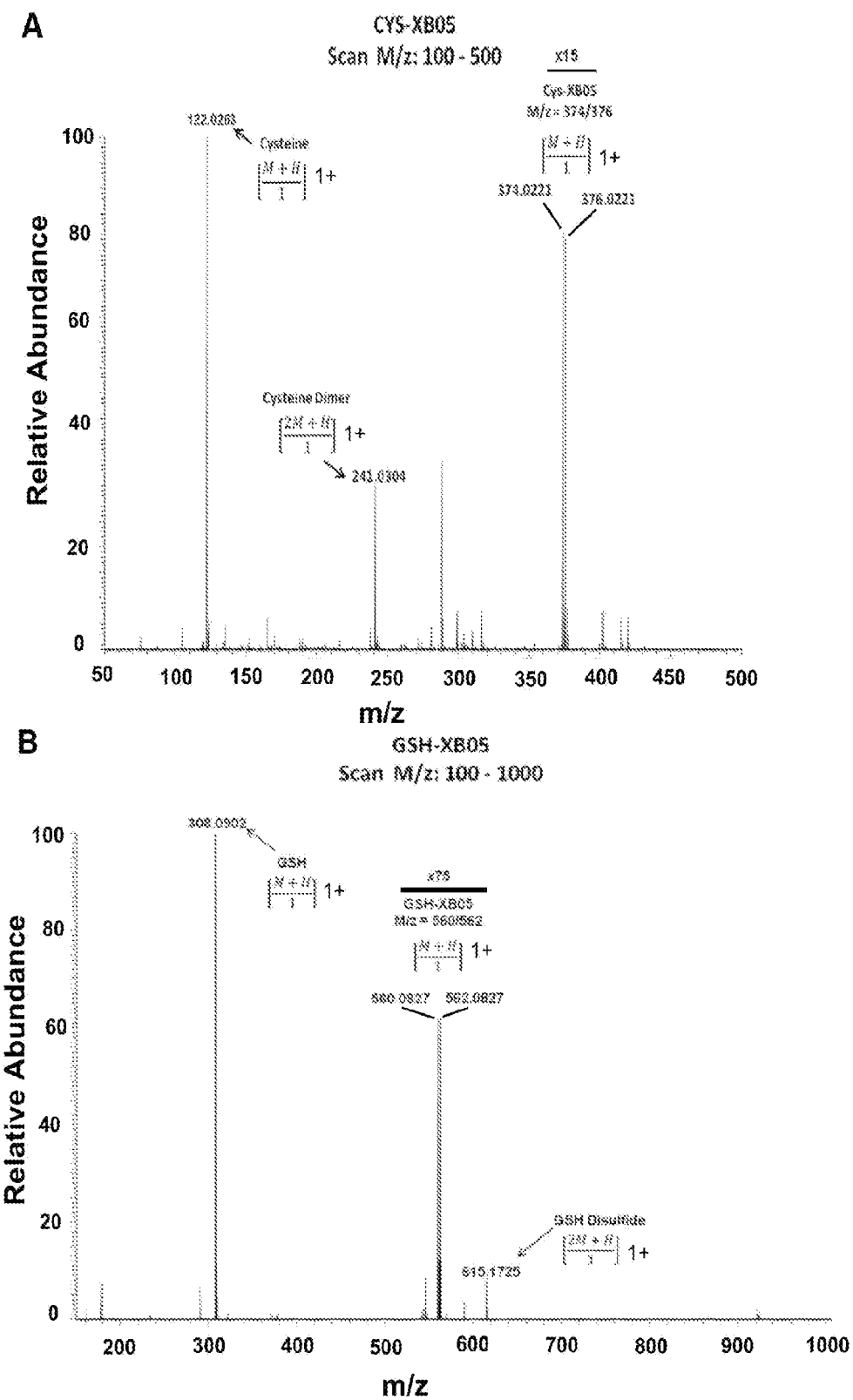
FIG. 18: XB05-Thiol Covalent Molecules. High resolution mass spectra for the reactions of XB05 with cysteine (A) and GSH (B). Experimental and theoretical isotope distributions for putative XB05 adducts formed via reactivity with the thiol groups of cysteine (C) and GSH (D). (E) Results of $^{19}F$ and $^{1}H$ Nuclear Magnetic Resonance (NMR) for reactions of XB05 with various compounds: cysteine, lysine, histidine, arginine, and reduced glutathione. (F) Preliminary structures for XB05-Cys and XB05-GSH adducts based on the observed mass to charge (m/z) ratios and comparison of experimental and theoretical isotope distributions for the proposed structures.
Figure 18:
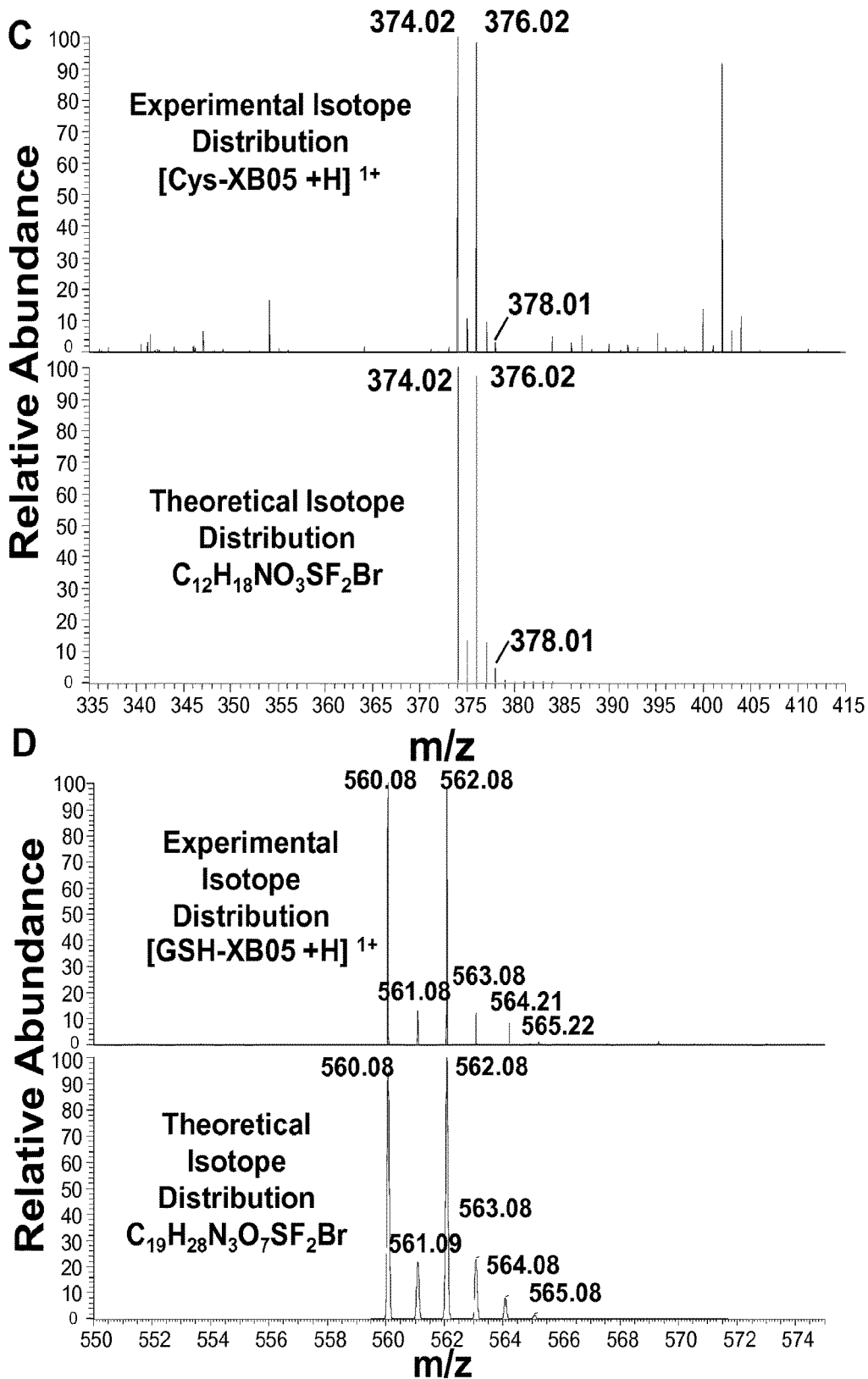

High resolution mass spectra were conducted for the reactions of XB05 with Cys or GSH. Incubation of 5 mM GSH and L-Cysteine were incubated with 1 mM XB05 in 20% methanol for 24 hours at 37° C. Samples were then subjected to high resolution electro-spray ionization mass spectrometry (ESI-MS) in positive ion mode on an LTQ Orbitrap XL (Thermoscientific Corp., West Palm Beach, Fla.) Hybrid Fourier Transform Mass Spectrometer (FIG. 18A and FIG. 18B). Both experimental and theoretical isotope distributions were compared for putative XB05 adducts which formed via reactivity with the thiol groups of Cys and GSH (FIG. 18C and FIG. 18D). Reactivity of XB05 with amino acids and reduced glutathione was monitored by $^{19}F$ and $^{1}H$ NMR. The various compounds tested for reactivity included: cysteine, lysine, histadine, arginine, and reduced glutathione. XB05 was shown to react with Cys and GSH but not with other nucleophilic amino acids (FIG. 18E). Preliminary structures for XB05-Cys and XB05-GSH adducts based on the observed mass to charge (m/z) ratios and the comparison of experimental and theoretical isotope distributions for the proposed structures are shown (FIG. 18F). Notably, a covalent bond is formed between the alkyne group of XB05 and the sulfhydryl side chain of Cys. The alcohol group of XB05 also appears to be oxidized to a carbonyl group under 20% MeOH solvent conditions.

Example B2

Antiproliferative Effects of XB05 and Other Compounds

Anti-proliferation activity was determined for 36 compounds within the scope of Formula (I) and those with the highest anti-proliferation activity are shown below. Anti-proliferation activity was determined using MTT assays with one or more cancer cell lines (i.e., one or more of A549, MCF7, DU-145, Hela, and HCT-116).

| Compound ID | Compound Structure | Anti-Proliferation Activity |
|---|---|---|
| XB-05 | 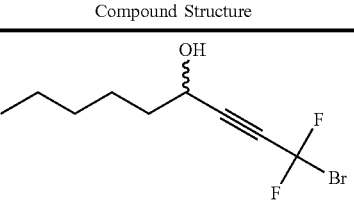 | +++ |

-continued

| Compound ID | Compound Structure | Anti-Proliferation Activity |
|---|---|---|
| XB127S | (structure: OH, alkyl chain, alkyne, CF2Br, F) | +++ |
| XB127R | (structure: OH, alkyl chain, alkyne, CF2Br, F) | +++ |
| LD-01-072 (a.k.a. TMO-112 and "XB05a" and BX12) | LD-01-072 (structure with OH, alkene, alkyne, CF2Br, F) | +++ |
| LD-4101 | (structure: acetate ester, alkyne, CF2Br, F) | +++ |
| L-01-010 (a.k.a. TMO-117 and "XB05b" and BX17) | n-C$_7$H$_{15}$, OH, alkyne, CF2Br, F | +++ |
| L-01-011 | n-C$_9$H$_{19}$, OH, alkyne, CF2Br, F | +++ |
| L-01-012 | n-C$_{11}$H$_{23}$, OH, alkyne, CF2Br, F | ++ |

Example B3

Inhibiting Effects on DMNT1 Activity

Figure 19A:
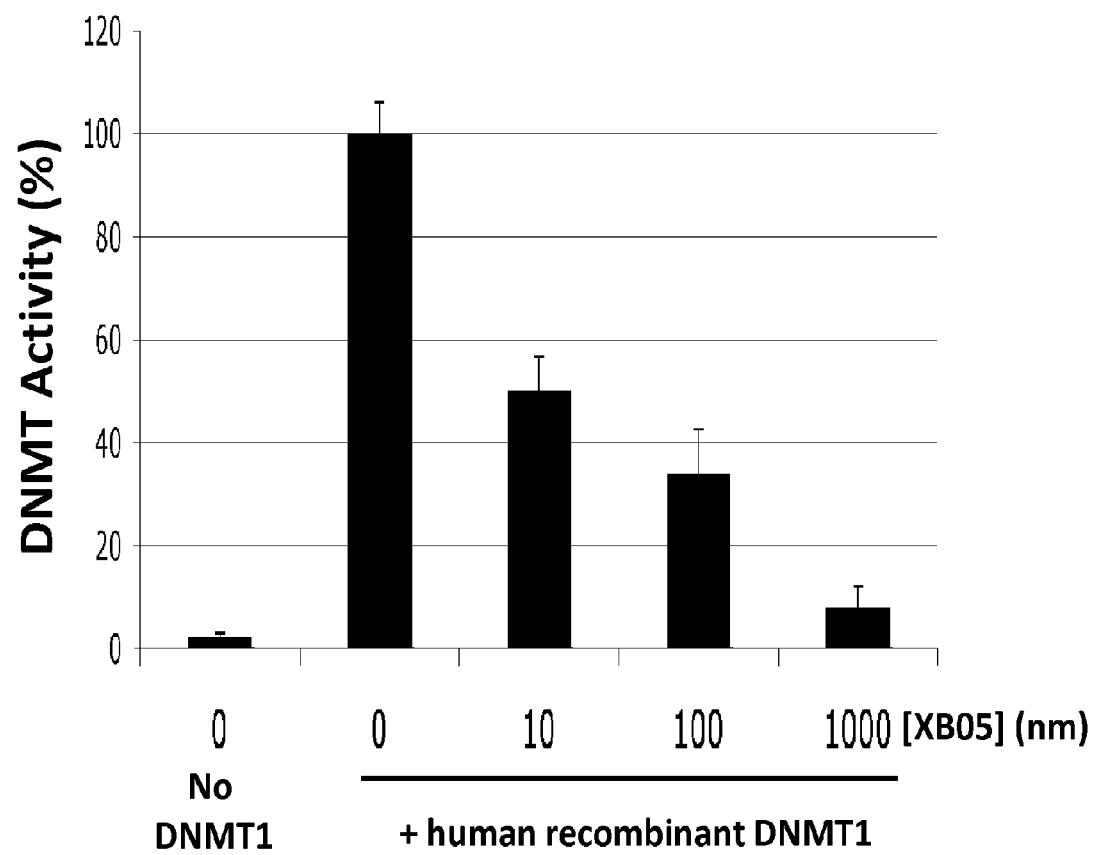
FIG. 19: Inhibitory Effects, in vitro. Inhibitory effects of XB05 (BX11) on DNMT1 activity are determined using (A) recombinant human DNMT1 or (B) nuclear extracts from cells treated with XB05 (BX11) or 5-Aza.
Figure 19B:
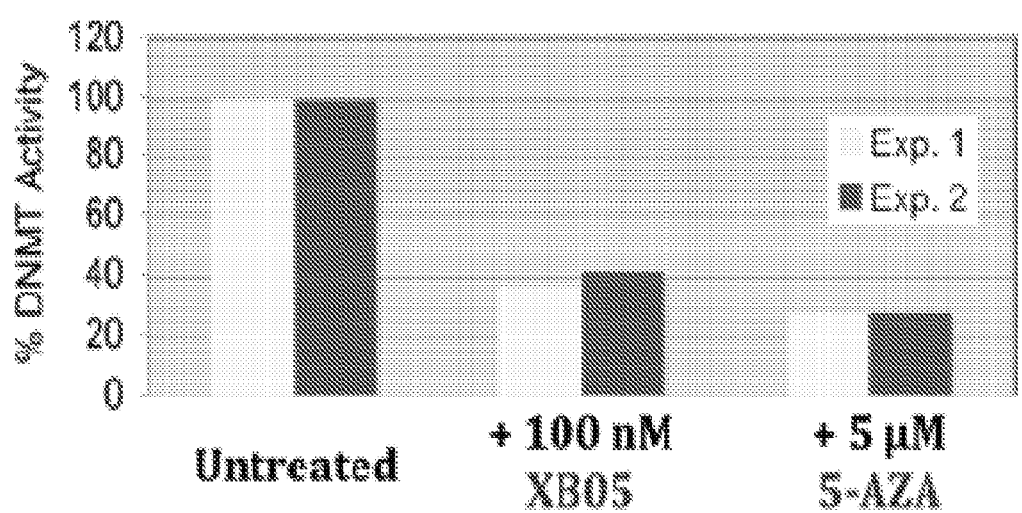

FIG. 19A and FIG. 19B show the inhibitory effects of XB05 (BX11) on DNMT1 activity. The assays use recombinant Human DNMT1 (FIG. 19A) or nuclear extracts prepared from cells treated with XB05 (BX11) or 5-Aza (5-azacytidine) (FIG. 19B).

Example B4

In Vivo Effects of XB05a (BX12)

Figure 20A:
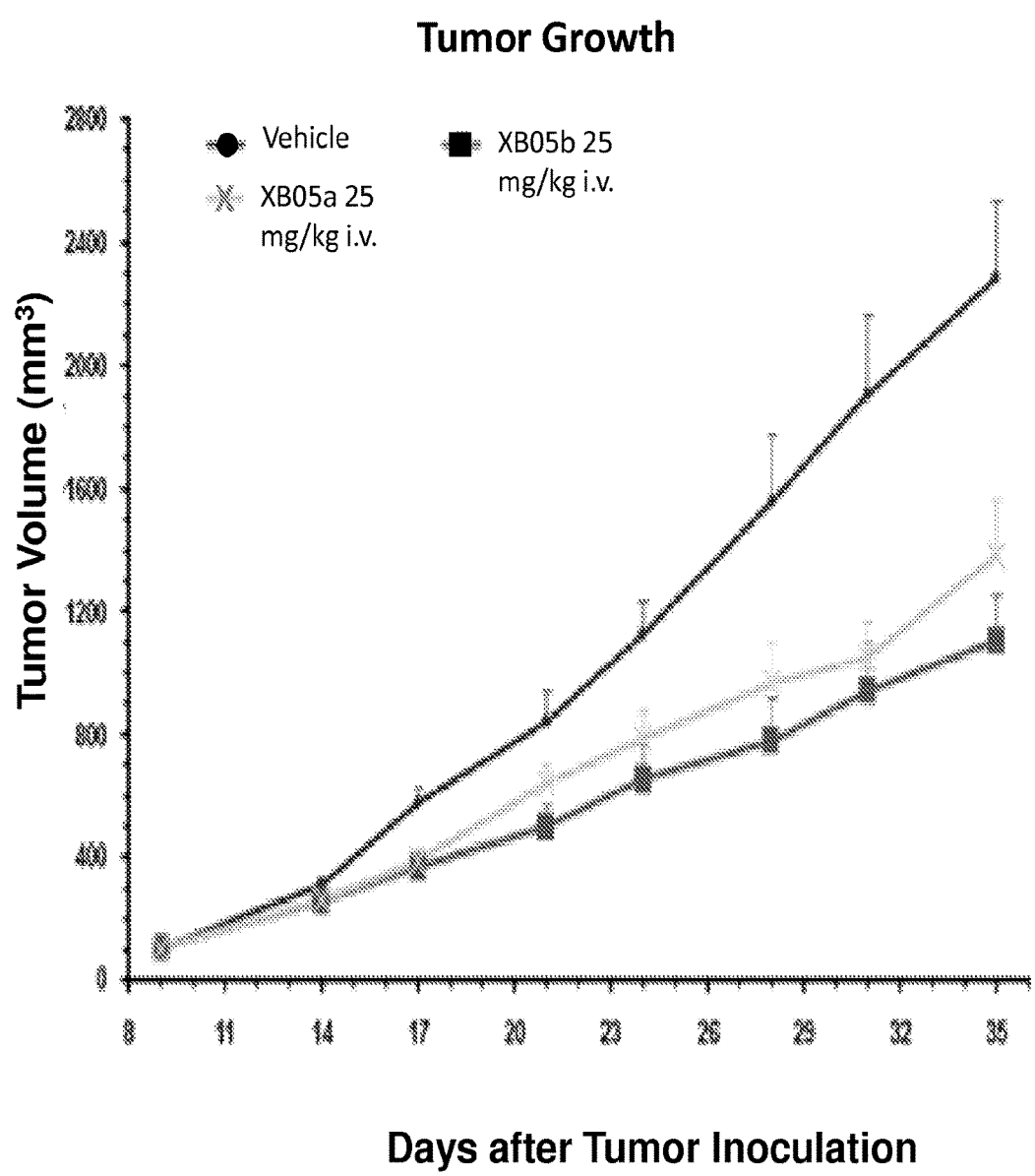
FIG. 20: Antitumor Effects in Mice. (A) The antitumor effect of XB05a and XB05b in nude mice bearing Colo-205 xenografts. Mice bearing subcutaneous colon cancer xenografts (Colo-205) were treated with vehicle or 25 mg/kg of BX12 (XB05a) or BX17 (XB05b) daily for 21 days by intravenous injection (except the last four doses of BX12 (XB05a) which were given intraperitoneally due to tail vein sensitivity). (B) Weight of the mice in the experiments described in (A).
Figure 20B:
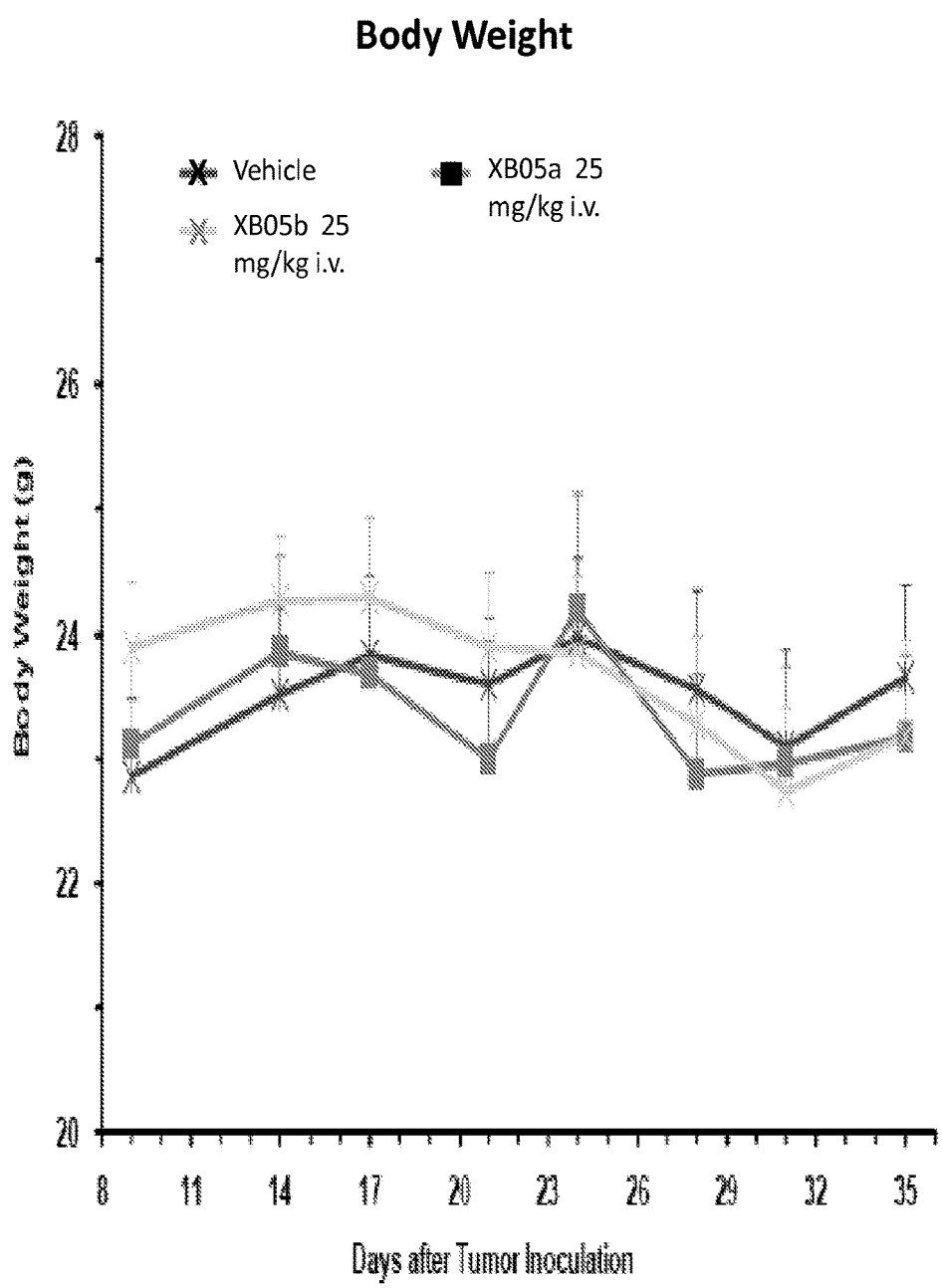

FIG. 20A shows the in vivo antitumor effects of XB05a (BX12) in nude mice bearing Colo-205 xenografts treated with 25 mg/kg/day i.v. with XB05a (BX12) or XB05b (BX17) for 21 days. FIG. 20B shows the weight of nude mice bearing a Colo-205 xenograft following treatment with a vehicle or 25 mg/kg of XB05a (BX12) or XB05b (BX17) daily for 21 days by i.v. injection.

The data show that XB05a (BX12) and XB05b (BX17) have in vivo antitumor efficacy (FIG. 20A) with no evidence of any severe non-specific toxicities, as judged by the body weight of the treated mice (FIG. 20B).

The headings used in the disclosure are not meant to suggest that all disclosure relating to the heading is found within the section that starts with that heading. Disclosure for any subject may be found throughout the specification.

It is noted that terms like "preferably," "commonly," and "typically" are not used herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

As used in the disclosure, "a" or "an" means one or more than one, unless otherwise specified. As used in the claims, when used in conjunction with the word "comprising" the words "a" or "an" means one or more than one, unless otherwise specified. As used in the disclosure or claims, "another" means at least a second or more, unless otherwise specified. As used in the disclosure, the phrases "such as", "for example", and "e.g." mean "for example, but not limited to" in that the list following the term ("such as", "for example", or "e.g.") provides some examples but the list is not necessarily a fully inclusive list. The word "comprising" means that the items following the word "comprising" may include additional unrecited elements or steps; that is, "comprising" does not exclude additional unrecited steps or elements.

Detailed descriptions of one or more embodiments are provided herein. It is to be understood, however, that the present invention may be embodied in various forms. Therefore, specific details disclosed herein (even if designated as preferred or advantageous) are not to be interpreted as limiting, but rather are to be used as an illustrative basis for the claims and as a representative basis for teaching one skilled in the art to employ the present invention in any appropriate manner. Indeed, various modifications of the invention in addition to those described herein will become apparent to those skilled in the art from the foregoing description and the accompanying figures. Such modifications are intended to fall within the scope of the appended claims.

What is claimed is:

1. A method for attenuating the activity of a DNA (cytosine-5)-methyltransferase 1 (DNMT1) inhibitor, the method comprising:

administering, to an animal who had previously been administered a DNMT1 inhibitor, a composition comprising an antioxidant, in an amount effective to attenuate the activity of the DNMT1 inhibitor
wherein the antioxidant is a thiol-based antioxidant and the DNMT1 inhibitor is a compound of Formula (I):

wherein:
R$_1$ is carboxy, (C$_1$-C$_{20}$)alkoxycarbonyl, (C$_2$-C$_{20}$)alkenyloxycarbonyl, (C$_2$-C$_{20}$)alkynyloxycarbonyl, (C$_1$-C$_{20}$)alkyl, (C$_2$-C$_{20}$)alkenyl, or (C$_2$-C$_{20}$)alkynyl, which (C$_1$-C$_{20}$)alkyl, C$_2$-C$_{20}$)alkenyl, or (C$_2$-C$_{20}$) alkynyl, is substituted with one or more groups independently selected from halo, hydroxy, mercapto, (C$_1$-C$_{20}$)alkoxy, (C$_2$-C$_{20}$)alkenyloxy, (C$_2$-C$_{20}$)alkynyloxy, aryloxy, heteroaryloxy, (C$_3$-C$_{20}$)cycloalkyloxy, heterocyclyloxy, (C$_1$-C$_{20}$)alkylthio, (C$_2$-C$_{20}$)alkenylthio, (C$_2$-C$_{20}$)alkynylthio, carboxy, (C$_1$-C$_{20}$)alkoxycarbonyl, (C$_2$-C$_{20}$) alkenyloxycarbonyl, (C$_2$-C$_{20}$)alkynyloxycarbonyl, aryl, heteroaryl, cycloalkyl, heterocyclyl, NR$_a$R$_b$, (C$_2$-C$_{20}$)alkynoyloxy, and arylcarbonyloxy;

R$_2$ is CF$_2$Br, CFHBr, CF$_2$Cl, CFHCl, CFBr$_2$, CFCl$_2$, CBr$_3$, C(R$_c$)(R$_d$)Br, C(R$_c$)(R$_d$)Cl, CF(R$_e$)Br, CF$_2$I, CFHI, C(R$_c$)(R$_d$)I, CF(R$_e$)I, or CCl$_3$;

each R$_a$ and R$_b$ is independently H, (C$_1$-C$_{20}$)alkyl, (C$_1$-C$_{20}$)alkanoyl, (C$_2$-C$_{20}$) alkenylcarbonyl, (C$_2$-C$_{20}$)alkynylcarbonyl, (C$_1$-C$_{20}$)alkoxy, (C$_2$-C$_{20}$)alkenyloxy, (C$_2$-C$_{20}$alkynyloxy, or aryl-(C$_1$-C$_{20}$) alkoxycarbonyl;

each R$_c$ and R$_d$ is independently H, (C$_1$-C$_{20}$)alkyl, (C$_1$-C$_{20}$)alkanoyl, (C$_2$-C$_{20}$)alkenylcarbonyl, (C$_2$-C$_{20}$)alkynylcarbonyl, (C$_1$-C$_{20}$)alkoxy, (C$_2$-C$_{20}$)alkenyloxy, or (C$_2$-C$_{20}$)alkynyloxy; and R$_e$ is (C$_1$-C$_{20}$)alkyl, (C$_1$-C$_{20}$)alkanoyl, (C$_2$-C$_{20}$)alkenylcarbonyl, (C$_2$-C$_{20}$)alkynylcarbonyl, (C$_1$-C$_{20}$) alkoxy, (C$_2$-C$_{20}$)alkenyloxy, or (C$_2$-C$_{20}$)alkynyloxy;

wherein each aryl, heteroaryl, heterocyclyl, aryloxy, heteroaryloxy, arylcarbonyloxy, or heteroarylcarbonyloxy of R$_1$ is optionally substituted with one or more groups independently selected from halo, hydroxy, nitro, cyano, trifluoromethyl, trifluoromethoxy, mercapto, carboxy, (C$_1$-C$_{20}$)alkyl, (C$_2$-C$_2$)alkenyl, (C$_2$-C$_{20}$)alkynyl, (C$_1$-C$_{20}$)alkoxy, (C$_2$-C$_{20}$)alkenyloxy, (C$_2$-C$_{20}$)alkynyloxy, (C$_1$-C$_{20}$) alkylthio, (C$_2$-C$_{20}$)alkenylthio, (C$_2$-C$_{20}$)alkynylthio, (C$_1$-C$_{20}$)alkoxycarbonyl, (C$_2$-C$_{20}$)alkenyloxycarbonyl, (C$_2$-C$_{20}$)alkynyloxycarbonyl, aryl, heteroaryl, aryl(C$_1$-C$_{20}$)alkyl, heteroaryl(C$_1$-C$_{20}$)alkyl, aryl(C$_2$-C$_{20}$)alkenyl, aryl(C$_2$-C$_{20}$)alkynyl, heteroaryl(C$_2$-C$_{20}$)alkenyl, heteroaryl(C$_2$-C$_{20}$)alkynyl, (C$_1$-C$_{20}$)alkanoyloxy, (C$_2$-C$_{20}$)alkenoyloxy, and (C$_2$-C$_{20}$) alkynoyloxy;
or a salt thereof.

2. A method for attenuating the activity of a DNA (cytosine-5)-methyltransferase 1 (DNMT1) inhibitor, the method comprising:
administering to an animal a composition comprising a DNMT1 inhibitor and an antioxidant,
wherein the antioxidant is a thiol-based antioxidant in an amount effective to attenuate the activity of the DNMT1 inhibitor and the DNMT1 inhibitor is a compound of Formula (I):

wherein:
R$_1$ is carboxy, (C$_1$-C$_{20}$)alkoxycarbonyl, (C$_2$-C$_{20}$)alkenyloxycarbonyl, (C$_2$-C$_{20}$)alkynyloxycarbonyl, (C$_1$-C$_{20}$)alkyl, (C$_2$-C$_{20}$)alkenyl, or (C$_2$-C$_{20}$)alkynyl, which (C$_1$-C$_{20}$)alkyl, (C$_2$-C$_{20}$)alkenyl, or (C$_2$-C$_{20}$) alkynyl, is substituted with one or more groups independently selected from halo, hydroxy, mercapto, (C$_1$-C$_{20}$)alkoxy, (C$_2$-C$_{20}$)alkenyloxy, (C$_2$-C$_{20}$)alkynyloxy, aryloxy, heteroaryloxy, (C$_3$-C$_{20}$)cycloalkyloxy, heterocyclyloxy, (C$_1$-C$_{20}$)alkylthio, (C$_2$-C$_{20}$)alkenylthio, (C$_2$-C$_{20}$)alkynylthio, carboxy, (C$_1$-C$_{20}$)alkoxycarbonyl, (C$_2$-C$_{20}$) alkenyloxycarbonyl, (C$_2$-C$_{20}$)alkynyloxycarbonyl, aryl, heteroaryl, cycloalkyl, heterocyclyl, NR$_a$R$_b$, (C$_2$-C$_{20}$)alkynoyloxy, and arylcarbonyloxy;

R$_2$ is CF$_2$Br, CFHBr, CF$_2$Cl, CFHCl, CFBr$_2$, CFCl$_2$CBr$_3$, C(R$_c$)R$_d$)Br, C(R$_c$)(R$_d$)Cl, CF(R$_e$)Br, CF$_2$I, CFHI, C(R$_c$)(R$_d$)I, CF(R$_e$)I, or CCl$_3$;

each R$_a$ and R$_b$ is independently H, (C$_1$-C$_{20}$)alkyl, (C$_1$-C$_{20}$)alkanoyl, (C$_2$-C$_{20}$) alkenylcarbonyl, (C$_2$-C$_{20}$)alkynylcarbonyl, (C$_1$-C$_{20}$)alkoxy, (C$_2$-C$_{20}$)alkenyloxy, (C$_2$-C$_{20}$alkynyloxy, or aryl-(C$_1$-C$_{20}$) alkoxycarbonyl;

each R$_c$ and R$_d$ is independently H, (C$_1$-C$_{20}$)alkyl, (C$_1$-C$_{20}$)alkanoyl, (C$_2$-C$_{20}$)alkenylcarbonyl, (C$_2$-C$_{20}$)alkynylcarbonyl, (C$_1$-C$_{20}$)alkoxy, (C$_2$-C$_{20}$)alkenyloxy, or (C$_2$-C$_{20}$)alkynyloxy; and R$_e$ is (C$_1$-C$_{20}$)alkyl, (C$_1$-C$_{20}$)alkanoyl, (C$_2$-C$_{20}$)alkenylcarbonyl, (C$_2$-C$_{20}$)alkynylcarbonyl, (C$_1$-C$_{20}$) alkoxy, (C$_2$-C$_{20}$)alkenyloxy, or (C$_2$-C$_{20}$)alkynyloxy;

wherein each aryl, heteroaryl, heterocyclyl, aryloxy, heteroaryloxy, arylcarbonyloxy, or heteroarylcarbonyloxy of R$_1$ is optionally substituted with one or more groups independently selected from halo, hydroxy, nitro, cyano, trifluoromethyl, trifluoromethoxy, mercapto, carboxy, (C$_1$-C$_{20}$)alkyl, (C$_2$-C$_{20}$)alkenyl, (C$_2$-C$_{20}$)alkynyl, (C$_1$-C$_{20}$)alkoxy, (C$_2$-C$_{20}$)alkenyloxy, (C$_2$-C$_{20}$)alkynyloxy, (C$_1$-C$_{20}$) alkylthio, (C$_2$-C$_{20}$)alkenylthio, (C$_2$-C$_{20}$)alkynylthio, (C$_1$-C$_{20}$)alkoxycarbonyl, (C$_2$-C$_{20}$)alkenyloxycarbonyl, (C$_2$-C$_{20}$)alkynyloxycarbonyl, aryl, heteroaryl, aryl(C$_1$-C$_{20}$)alkyl, heteroaryl(C$_1$-C$_{20}$)alkyl, aryl(C$_2$-C$_{20}$)alkenyl, aryl(C$_2$-C$_{20}$)alkynyl, heteroaryl(C$_2$-C$_{20}$)alkenyl, heteroaryl(C$_2$-C$_{20}$)alkynyl, (C$_1$-C$_{20}$)alkanoyloxy, (C$_2$-C$_{20}$)alkenoyloxy, and (C$_2$-C$_{20}$) alkynoyloxy;
or a salt thereof.

3. The method of claim 2, wherein the activity of the DNMT1 inhibitor comprises reactivity with a cellular thiol and the cellular thiol is a thiol on a cysteine residue.

4. The method of claim 3, wherein the cysteine residue is a residue of a DNMT1 protein.

5. The method of claim 2, wherein the thiol-based antioxidant is N-acetyl cysteine or glutathione.

6. The method of claim 1, wherein the thiol-based antioxidant is N-acety cysteine or glutathione.

7. The method of claim 1, wherein the compound of Formula (I) is a compound of Formula (II):

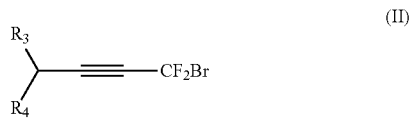

(II)

wherein: $R_3$ is hydroxy, mercapto, chloro, bromo, methylthio, ethylthio, methoxy, ethoxy, acetylamino, $(C_1-C_{10})$alkanoyloxy, arylcarbonyloxy, or aryloxy; and $R_4$ is $(C_4-C_{10})$alkyl, $(C_2-C_{10})$alkenyl, or $(C_2-C_{10})$alkynyl, which $(C_4-C_{10})$alkyl, $(C_2-C_{10})$alkenyl, or $(C_2-C_{10})$alkynyl is optionally substituted with one or more groups independently selected from halo, hydroxy, mercapto, $(C_1-C_{10})$alkoxy, $(C_1-C_{10})$alkylthio, carboxy, $(C_1-C_{10})$alkoxycarbonyl, aryl, heteroaryl, and $NR_aR_b$.

8. The method of claim 2, wherein:

$R_1$ is carboxy, $(C_1-C_{20})$alkoxycarbonyl, $(C_2-C_{20})$alkenyloxycarbonyl, $(C_2-C_{20})$alkynyloxycarbonyl, $(C_1-C_{20})$alkyl, $(C_2-C_{20})$alkenyl, or $(C_2-C_{20})$alkynyl, which $(C_1-C_{20})$alkyl, $(C_2-C_{20})$alkenyl, or $(C_2-C_{20})$alkynyl, is substituted with one or more groups independently selected from halo, hydroxy, mercapto, $(C_1-C_{20})$alkoxy, $(C_2-C_{20})$alkenyloxy, $(C_2-C_{20})$alkynyloxy, $(C_1-C_{20})$alkylthio, $(C_2-C_{20})$alkenylthio, $(C_2-C_{20})$alkynylthio, carboxy, $(C_1-C_{20})$alkoxycarbonyl, $(C_2-C_{20})$alkenyloxycarbonyl, $(C_2-C_{20})$alkynyloxycarbonyl, aryl, heteroaryl, and $NR_aR_b$;

$R_2$ is $CF_2Br$, $CFHBr$, $CF_2Cl$, $CFHCl$, $CFBr_2$, $CFCl_2$, $CBr_3$, $C(R_c)(R_d)Br$, $C(R_c)(R_d)Cl$, $CF(R_e)Br$, or $CCl_3$;

each $R_a$ and $R_b$ is independently H, $(C_1-C_{20})$alkyl, $(C_1-C_{20})$alkanoyl, $(C_2-C_{20})$alkenylcarbonyl, $(C_2-C_{20})$alkynylcarbonyl, $(C_1-C_{20})$alkoxy, $(C_2-C_{20})$alkenyloxy, or $(C_2-C_{20})$alkynyloxy;

each $R_c$ and $R_d$ is independently H, $(C_1-C_{20})$alkyl, $(C_1-C_{20})$alkanoyl, $(C_2-C_{20})$alkenylcarbonyl, $(C_2-C_{20})$alkynylcarbonyl, $(C_1-C_{20})$alkoxy, $(C_2-C_{20})$alkenyloxy, or $(C_2-C_{20})$alkynyloxy; and $R_e$ is $(C_1-C_{20})$alkyl, $(C_1-C_{20})$alkanoyl, $(C_2-C_{20})$alkenylcarbonyl, $(C_2-C_{20})$alkynylcarbonyl, $(C_1-C_{20})$alkoxy, $(C_2-C_{20})$alkenyloxy, or $(C_2-C_{20})$alkynyloxy;

wherein each aryl or heteroaryl of $R_1$ is optionally substituted with one or more groups independently selected from halo, hydroxy, nitro, cyano, trifluoromethyl, trifluoromethoxy, mercapto, carboxy, $(C_1-C_{20})$alkyl, $(C_2-C_{20})$alkenyl, $(C_2-C_{20})$alkynyl, $(C_1-C_{20})$alkoxy, $(C_2-C_{20})$alkenyloxy, $(C_2-C_{20})$alkynyloxy, $(C_1-C_{20})$alkylthio, $(C_2-C_{20})$alkenylthio, $(C_2-C_{20})$alkynylthio, $(C_1-C_{20})$alkoxycarbonyl, $(C_2-C_{20})$alkenyloxycarbonyl, $(C_2-C_{20})$alkynyloxycarbonyl, aryl, heteroaryl, aryl$(C_1-C_{20})$alkyl, heteroaryl$(C_1-C_{20})$alkyl, aryl$(C_2-C_{20})$alkenyl, aryl$(C_2-C_{20})$alkynyl, heteroaryl$(C_2-C_{20})$alkenyl, heteroaryl$(C_2-C_{20})$alkynyl, $(C_1C_{20})$alkanoyloxy, $(C_2-C_{20})$alkenoyloxy, and $(C_2-C_{20})$alkynoyloxy;

or a salt thereof.

9. The method of claim 2, wherein $R_1$ is a $(C_1-C_{20})$alkyl, $(C_2-C_{20})$alkenyl, or $(C_2-C_{20})$alkynyl, which $(C_1-C_{20})$alkyl, $(C_2-C_{20})$alkenyl, or $(C_2-C_{20})$alkynyl is substituted with hydroxy, mercapto, carboxy, or $NR_aR_b$.

10. The method of claim 2, wherein the compound of Formula (I) is a compound of Formula (II):

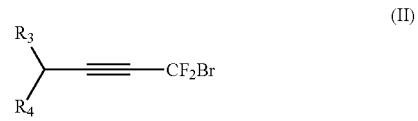

(II)

wherein: $R_3$ is hydroxy, mercapto, chloro, bromo, methylthio, ethylthio, methoxy, ethoxy, acetylamino, $(C_1-C_{10})$alkanoyloxy, arylcarbonyloxy, or aryloxy; and $R_4$ is $(C_4-C_{10})$alkyl, $(C_2-C_{10})$alkenyl, or $(C_2-C_{10})$alkynyl, which $(C_4-C_{10})$alkyl, $(C_2-C_{10})$alkenyl, or $(C_2-C_{10})$alkynyl is optionally substituted with one or more groups independently selected from halo, hydroxy, mercapto, $(C_1-C_{10})$alkoxy, $(C_1-C_{10})$alkylthio, carboxy, $(C_1-C_{10})$alkoxycarbonyl, aryl, heteroaryl, and $NR_aR_b$.

11. The method of claim 2, wherein the compound is

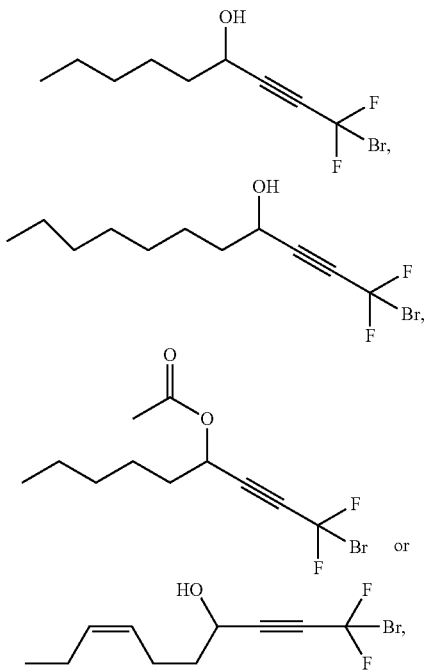

or a salt thereof.

12. The method of claim 2 wherein the animal has cancer.

13. The method of claim 12, wherein the cancer is selected from chondrosarcoma cancer, malignant peripheral nerve sheath tumor, malignant melanoma, a sarcoma, brain cancer, liver cancer, leukemia, myelodysplastic syndrome, basal cell carcinoma, thyroid cancer, squamous cell carcinoma, neuroblastoma, ovarian cancer, melanoma, renal cell carcinoma, hepatocellular carcinoma, breast cancer, colon cancer, lung cancer, pancreatic cancer, prostate cancers, chronic lymphocytic leukemia (CLL), acute lymphoblastic leukemia, rhabdomyosarcoma, Glioblastoma multiforme, meningioma, bladder cancer, gastric cancer, Glioma, oral cancer, nasopharyngeal carcinoma, kidney cancer, rectal cancer, stomach cancer, uterine cancer, and leukemias.

14. The method of claim 12, wherein the method for attenuating treats angiogenesis or metastasis in a tumor.

15. The method of claim 12, wherein the method for attenuating results in the reduction of tumor size, the reduction in the number of tumors, or both.

16. The method of claim 1, wherein the compound is

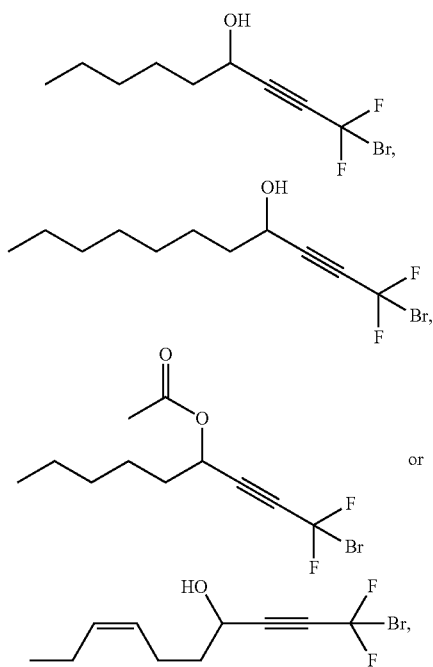

or a salt thereof.

17. A composition comprising a DNMT1 inhibitor and an antioxidant, wherein the antioxidant is a thiol-based antioxidant in an amount effective to attenuate the activity of the DNMT1 inhibitor and the DNMT1 inhibitor is a compound of Formula (I):

 (I)

wherein:

$R_1$ is carboxy, $(C_1\text{-}C_{20})$alkoxycarbonyl, $(C_2\text{-}C_{20})$alkenyloxycarbonyl, $(C_2\text{-}C_{20})$alkynyloxycarbonyl, $(C_1\text{-}C_{20})$alkyl, $(C_2\text{-}C_{20})$alkenyl, or $(C_2\text{-}C_{20})$alkynyl, which $(C_1\text{-}C_{20})$alkyl, $(C_2\text{-}C_{20})$alkenyl, or $(C_2\text{-}C_{20})$alkynyl, is substituted with one or more groups independently selected from halo, hydroxy, mercapto, $(C_1\text{-}C_{20})$alkoxy, $(C_2\text{-}C_{20})$alkenyloxy, $(C_2\text{-}C_{20})$alkynyloxy, aryloxy, heteroaryloxy, $(C_3\text{-}C_{20})$cycloalkyloxy, heterocyclyloxy, $(C_1\text{-}C_{20})$alkylthio, $(C_2\text{-}C_{20})$alkenylthio, $(C_2\text{-}C_{20})$alkynylthio, carboxy, $(C_1\text{-}C_{20})$alkoxycarbonyl, $(C_2\text{-}C_{20})$alkenyloxycarbonyl, $(C_2\text{-}C_{20})$alkynyloxycarbonyl, aryl, heteroaryl, cycloalkyl, heterocyclyl, $NR_aR_b$, $(C_2\text{-}C_{20})$alkynoyloxy, and arylcarbonyloxy;

$R_2$ is $CF_2Br$, $CFHBr$, $CF_2Cl$, $CFHCl$, $CFBr_2CFCl_2$, $CBr_3$, $C(R_c)(R_d)Br$, $C(R_c)(R_d)Cl$, $CF(R_e)Br$, $CF_2I$, $CFHI$, $C(R_c)(R_d)I$, $CF(R_e)I$, or $CCl_3$;

each $R_a$ and $R_b$ is independently H, $(C_1\text{-}C_{20})$alkyl, $(C_1\text{-}C_{20})$alkanoyl, $(C_2\text{-}C_{20})$alkenylcarbonyl, $(C_2\text{-}C_{20})$alkynylcarbonyl, $(C_1\text{-}C_{20})$alkoxy, $(C_2\text{-}C_{20})$alkenyloxy, $(C_2\text{-}C_{20})$alkynyloxy, or aryl-$(C_1\text{-}C_{20})$alkoxycarbonyl;

each $R_c$ and $R_d$ is independently H, $(C_1\text{-}C_{20})$alkyl, $(C_1\text{-}C_{20})$alkanoyl, $(C_2\text{-}C_{20})$alkenylcarbonyl, $(C_2\text{-}C_{20})$alkynylcarbonyl, $(C_1\text{-}C_{20})$alkoxy, $(C_2\text{-}C_{20})$alkenyloxy, or $(C_2\text{-}C_{20})$alkynyloxy; and $R_e$ is $(C_1\text{-}C_{20})$alkyl, $(C_1\text{-}C_{20})$alkanoyl, $(C_2\text{-}C_{20})$alkenylcarbonyl, $(C_2\text{-}C_{20})$alkynylcarbonyl, $(C_1\text{-}C_{20})$alkoxy, $(C_2\text{-}C_{20})$alkenyloxy, or $(C_2\text{-}C_{20})$alkynyloxy;

wherein each aryl, heteroaryl, heterocyclyl, aryloxy, heteroaryloxy, arylcarbonyloxy, or heteroarylcarbonyloxy of $R_1$ is optionally substituted with one or more groups independently selected from halo, hydroxy, nitro, cyano, trifluoromethyl, trifluoromethoxy, mercapto, carboxy, $(C_1\text{-}C_{20})$alkyl, $(C_2\text{-}C_2)$alkenyl, $(C_2\text{-}C_{20})$alkynyl, $(C_1\text{-}C_{20})$alkoxy, $(C_2\text{-}C_{20})$alkenyloxy, $(C_2\text{-}C_{20})$alkynyloxy, $(C_1\text{-}C_{20})$alkylthio, $(C_2\text{-}C_{20})$alkenylthio, $(C_2\text{-}C_{20})$alkynylthio, $(C_1\text{-}C_{20})$alkoxycarbonyl, $(C_2\text{-}C_{20})$alkenyloxycarbonyl, $(C_2\text{-}C_{20})$alkynyloxycarbonyl, aryl, heteroaryl, aryl$(C_1\text{-}C_{20})$alkyl, heteroaryl$(C_1\text{-}C_{20})$alkyl, aryl$(C_2\text{-}C_{20})$alkenyl, aryl$(C_2\text{-}C_{20})$alkynyl, heteroaryl$(C_2\text{-}C_{20})$alkenyl, heteroaryl$(C_2\text{-}C_{20})$alkynyl, $(C_1\text{-}C_{20})$alkanoyloxy, $(C_2\text{-}C_{20})$alkenoyloxy, and $(C_2\text{-}C_{20})$alkynoyloxy;

or a salt thereof.

18. A method for treating an animal, the method comprising:

administering to the animal the composition of claim 17.

19. A method for treating at least one cell, the method comprising:

administering to at least one cell the composition of claim 17.

* * * * *